US011142500B2

(12) United States Patent
Jasti et al.

(10) Patent No.: US 11,142,500 B2
(45) Date of Patent: Oct. 12, 2021

(54) NANOHOOP COMPOUND EMBODIMENTS COMPRISING META-SUBSTITUTION AND MOLECULAR SYSTEMS COMPRISING THE SAME

(71) Applicant: University of Oregon, Eugene, OR (US)

(72) Inventors: Ramesh Jasti, Eugene, OR (US); Jeff Van Raden, Eugene, OR (US)

(73) Assignee: University of Oregon, Eugene, OR (US)

( * ) Notice: Subject to any disclaimer, the term of this patent is extended or adjusted under 35 U.S.C. 154(b) by 196 days.

(21) Appl. No.: 16/505,252

(22) Filed: Jul. 8, 2019

(65) Prior Publication Data
US 2020/0010419 A1    Jan. 9, 2020

Related U.S. Application Data

(60) Provisional application No. 62/695,659, filed on Jul. 9, 2018.

(51) Int. Cl.
| | |
|---|---|
| *C07D 213/16* | (2006.01) |
| *G01N 21/64* | (2006.01) |
| *C08G 83/00* | (2006.01) |
| *C07F 5/02* | (2006.01) |
| *C07C 13/273* | (2006.01) |
| *C07C 43/205* | (2006.01) |
| *C07D 471/08* | (2006.01) |
| *C07D 471/18* | (2006.01) |
| *C07D 471/22* | (2006.01) |
| *C07C 43/225* | (2006.01) |
| *C07C 15/14* | (2006.01) |
| *C07C 1/20* | (2006.01) |

(52) U.S. Cl.
CPC .......... *C07D 213/16* (2013.01); *C07C 13/273* (2013.01); *C07C 43/205* (2013.01); *C07D 471/08* (2013.01); *C07D 471/18* (2013.01); *C07D 471/22* (2013.01); *C07F 5/02* (2013.01); *C08G 83/007* (2013.01); *G01N 21/6428* (2013.01); *C07C 1/20* (2013.01); *C07C 15/14* (2013.01); *C07C 43/225* (2013.01); *G01N 2021/6439* (2013.01); *Y10T 436/11* (2015.01)

(58) Field of Classification Search
CPC .................................................. C07D 213/16
See application file for complete search history.

(56) References Cited

U.S. PATENT DOCUMENTS

| | | | |
|---|---|---|---|
| 8,461,403 B2 | 6/2013 | Jasti et al. | |
| 8,895,768 B2 | 11/2014 | Yamago | |
| 8,987,538 B2 * | 3/2015 | Jasti | C07F 5/025 585/26 |
| 9,090,473 B2 | 7/2015 | Jasti et al. | |
| 9,162,939 B2 * | 10/2015 | Jasti | C07F 5/025 |
| 9,481,618 B2 | 11/2016 | Itami et al. | |
| 9,527,737 B2 | 12/2016 | Itami et al. | |
| 10,654,780 B2 * | 5/2020 | Jasti | B01J 20/28007 |
| 10,934,290 B2 * | 3/2021 | Jasti | H01L 51/0067 |
| 2011/0166390 A1 | 7/2011 | Jasti et al. | |
| 2012/0220790 A1 | 8/2012 | Yamago | |
| 2016/0372684 A1 | 12/2016 | Jasti et al. | |
| 2018/0290952 A1 | 10/2018 | Jasti et al. | |
| 2019/0025315 A1 | 1/2019 | Jasti et al. | |

OTHER PUBLICATIONS

Darzi et al., "Selective syntheses of [7]-[12]Cycloparaphenylenes using orthogonal Suzuki-Miyaura cross-coupling reactions," *Journal of Organic Chemistry*, vol. 77, pp. 6624-6628, Jul. 17, 2012.
Nishihara et al., "Excited states in cycloparaphenylenes: dependence of optical properties on ring length," *Journal of Physical Chemistry Letters*, vol. 3, pp. 3125-3128, Oct. 12, 2012.
Non-Final Office Action issued for U.S. Appl. No. 16/041,676 dated Feb. 6, 2020.
Ozasa et al., "Studies of polyphenyls and polyphenylenes. II. The synthesis and physical properties of polyphenyls containing para linkage," *Bull. Chem. Soc. Jpn.*, 53(9): 2610-2617, 1980.
Salvatella, "The alkyl group is a-1 + R substituent," *Educacion Quimica*, vol. 28, pp. 232, 237, Jul. 17, 2017.
Xue et al., "Cyclo-meta-phenylene revisited: nickel-mediated synthesis, molecular structures, and device applications," *Journal of Organic Chemistry*, vol. 79, pp. 9735-9739, pp. 9735-9739, Sep. 29, 2014.
Ball et al., "Stepping into the Light: Conjugated Macrocycles with Donor-Acceptor Motifs," *ACS Cent. Sci.*, 1, 416-417, Oct. 27, 2015.
Darzi et al., "Synthesis, Properties, and Design Principles of Donor-Acceptor Nanohoops," *ACS Central Science*, vol. 1, pp. 335-342, Sep. 3, 2015.
Darzi et al., "The dynamic, size-dependent properties of [5]-[12]cycloparaphenylenes," *Chem. Soc. Rev.*, vol. 44, pp. 6401-6410, Apr. 27, 2015.
Darzi, Research Presentation/Slides, Sep. 24, 2014.
Havinga et al., "A new class of small band gap organic polymer conductors," *Polymer Bulletin*, 29(119): 119-126, Aug. 1992.
Hirst "Synthesis of Nitrogen-Substituted Cycloparaphenylenes," Dissertation, May 2014.
Hirst "Synthesis of Nitrogen-Substituted Cycloparaphenylenes," Thesis Defense Presentation, May 13, 2014.
Ishii et al., "Synthesis and dimerization of chloro[10]cyclopharaphenylene: A directly connected cycloparaphenylene dimer," *Organic Letters*, 16(8): 2174-2176, Apr. 1, 2014.
Iwamoto et al., "Selective and Random Syntheses of [n]Cycloparaphenylenes (n = 8-13) and Size Dependence of Their Electronic Properties," *Journal of the American Chemical Society*, 133(21): 8354-8361, May 4, 2011.

(Continued)

*Primary Examiner* — Golam M Shameem
(74) *Attorney, Agent, or Firm* — Klarquist Sparkman, LLP

(57) ABSTRACT

Disclosed herein are embodiments of nanohoop compounds, methods of making, and methods of using the same. The nanohoop compounds disclosed herein have discrete ring system(s) that comprise a unique meta-substituted motif that affords a strained cavity in which myriad reaction chemistries can take place. The unique structures and properties of the nanohoop compounds disclosed herein also lend to their use in a variety of biological applications, and as interlocked structures in molecular machines.

14 Claims, 20 Drawing Sheets

(56) References Cited

OTHER PUBLICATIONS

Iwamoto et al., "Size-Selective Encapsulation of $C_{60}$ by [10]Cycloparaphenylene: Formation of the Shortest Fullerene-Peapod," *Agnew. Chem. Int. Ed.*, vol. 50, pp. 8342-8344, Jul. 18, 2011.

Jasti et al., "Synthesis, Characterization, and Theory of [9]-, [12]-, and [18]Cycloparaphenylene: Carbon Nanohoop Structures," *J. Am. Chem. Soc.*, vol. 130, pp. 17646-17647, Dec. 4, 2008.

Kikuchi et al., "Definitive evidence for the contribution of biradical character in a closed-shell molecule, derivative of 1,4-Bis-(4,5-diphenylimidazol-2-ylidene)cyclohexa-2,5,-diene," *JACS Communications*, 126(21): 6526-6527, May 11, 2004.

Kubota et al., "η6-cycloparaphenylene transition metal complexes: synthesis, structure, photophysical properties, and application to the selective monofunctionalization of cycloparaphenylenes," *JACS*, vol. 137, pp. 1356-1361, Jan. 12, 2015.

Kuwabara et al., "Curved oligophenylenes as donors in shape-persistent donor-acceptor macrocycles with solvatofluorochromic properties," *Angew. Chem. Int. Ed.*, 54(33): 9646-9649, Aug. 10, 2015.

Matsui et al., "Synthesis and properties of cycloparaphenylene-2,5-pyridylidene: a nitrogen-containing carbon nanoring," *Organic Letters*, 14(7): 1888-1891, Mar. 23, 2012.

Mutoh et al., "Entropy-controlled biradical-quinoid isomerization of a π-conjugated delocalized biradical," *Phys. Chem. Chem. Phys.*, 17(2): 1151-1155, Nov. 17, 2014.

Oki et al., "One-pot synthesis of a rice-ball-shaped cyclophane with syn-diethanoanthracene-fused dipyrrole and hexafluorobenzene," *Chem. Lett.*, vol. 46, pp. 243-244, Nov. 26, 2016.

Rio et al., "Cyclotetrahalo-p-phenylenes: simulations of halogen substituted cycloparaphenylenes and their interaction with $C_{60}$," *Phys. Chem. Chem. Phys.*, 18(33): 23257-23263, Jul. 22, 2016.

Takase et al., "Donor-acceptor segregated paracyclophanes composed of naphthobipyrrole and stacked fluoroarenes," *Organic Letters*, 15(13): 3202-3205, Jun. 21, 2013.

Xia et al., "Gram-scale synthesis and crystal structures of [8]- and [10]CPP, and the solid-state structure of $C_{60}$@[10]CPP," *Chemical Science*, vol. 3, pp. 3018-3021, Jul. 11, 2012.

Xia et al., "Synthesis, Characterization and Computational Studies of Cycloparaphenylene Dimers," *J. Am. Chem. Soc.*, 134(48): 19709-19715, Nov. 6, 2012.

Zhang et al., "Giant Cyclo[n]thiophenes with Extended π Conjugation," *Angewandte Chemie Int. Ed.*, 48(36): 6632-6635, Jun. 27, 2009.

\* cited by examiner

NANOHOOP COMPOUND EMBODIMENTS COMPRISING META-SUBSTITUTION AND MOLECULAR SYSTEMS COMPRISING THE SAME

CROSS REFERENCE TO RELATED APPLICATION

This application claims the benefit of U.S. Provisional Application No. 62/695,659 filed on Jul. 9, 2018, which is incorporated herein by reference in its entirety.

ACKNOWLEDGMENT OF GOVERNMENT SUPPORT

This invention was made with government support under Contract No. CHE-1255219 awarded by the National Science Foundation. The government has certain rights in the invention.

FIELD

The present disclosure concerns substituted nanohoop compounds comprising a discrete ring system having at least one aromatic group comprising meta-substitution, as well as methods of making and using the same.

BACKGROUND

Recent studies in the field of synthetic molecular machines (e.g., molecular rotors, molecular muscles, molecular switches, molecular motors, molecular shuttles, etc.) have progressed, with recent examples performing highly complex molecular-level tasks akin to those in the biological realm. Success of the synthetic molecular machines can, in part, be attributed to the continued development of the fundamental building blocks, such as interlocked molecules that constitute molecular machines. Exemplary interlocked molecules can include, but are not limited to, rotaxanes, catenanes, and the like. Machine-like functionality that is derived from these fundamental building blocks can be controlled, in part, by molecular composition of the interlocked components.

There exists a need in the art for new ring systems that can serve as macrocycles for interlocked molecules and further that can be used in various other applications/processes, such as in guest-host chemistry, polymerization chemistry, catalysis, and the like.

SUMMARY

Disclosed herein are embodiments of nanohoop compounds having structures satisfying formulas described herein. The nanohoop compound embodiments have at least one discrete ring system comprising at least one aromatic ring having a meta-substitution pattern wherein bonds of the at least one aromatic ring that bind the aromatic ring to other rings in the nanohoop compound and/or other rings of the discrete ring system are positioned meta relative to one another.

Also disclosed herein are nanohoop compounds further comprising an interlocked compound constrained within a cavity defined by the nanohoop compound. Such compounds can be used as sensors and/or molecular machines. In some embodiments, such compounds are nanohoop rotaxane compounds.

Disclosed herein are also embodiments of a method embodiments for making nanohoop compound embodiments disclosed herein, as well as methods for making interlocked compounds comprising such nanohoop compounds. Also disclosed are methods of using nanohoop compound embodiments and interlocked compounds comprising a nanohoop compound and an interlocked compound constrained within the cavity of the nanohoop compound.

The foregoing and other objects and features of the present disclosure will become more apparent from the following detailed description, which proceeds with reference to the accompanying figures.

DETAILED DESCRIPTION

I. EXPLANATION OF TERMS

Figure 1:
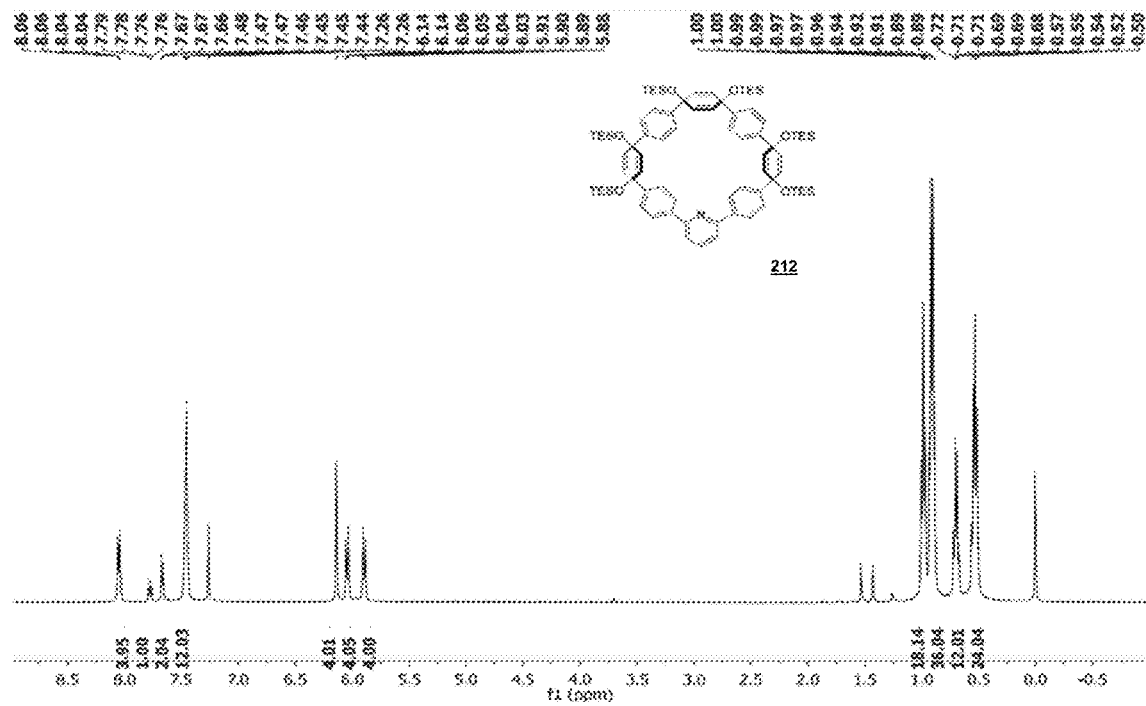
FIG. 1 is a $^1$H nuclear magnetic resonance (NMR) spectrum of nanohoop precursor embodiment 212.

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting, unless otherwise indicated. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/methods. When directly and explicitly distinguishing embodiments from discussed prior art, the embodiment numbers are not approximates unless the word "about" is recited. Furthermore, not all alternatives recited herein are equivalents.

To facilitate review of the various embodiments of the disclosure, the following explanations of specific terms are provided. Certain functional group terms include a "-" symbol at the beginning of the functional group formula; this symbol is not a part of the functional group, but instead denotes how the functional group connects to the formulas described herein. For example, a functional group with a formula "—OC(O)R$^b$" is attached to an atom of the functionalized compound by the oxygen atom of the functional group that is next to the "-" symbol.

Acyl Halide: —C(O)X, wherein X is a halogen, such as Br, F, I, or Cl.

Acyloxy: —OC(O)R$^b$, wherein R$^b$ is selected from hydrogen, alkyl, alkenyl, alkynyl, aryl, heteroalkyl, heteroalkenyl, heteroalkynyl, or heteroaryl.

Aldehyde: —C(O)H.

Aliphatic: A hydrocarbon group having at least one carbon atom to 50 carbon atoms (C$_1$-C$_{50}$), such as one to 25 carbon atoms (C$_1$-C$_{25}$), or one to ten carbon atoms (C$_1$-C$_{10}$), and which includes alkanes (or alkyl), alkenes (or alkenyl), alkynes (or alkynyl), including cyclic versions thereof, and further including straight- and branched-chain arrangements, and all stereo and position isomers as well. Aliphatic does not include aromatic compounds.

Alkenyl: An unsaturated monovalent hydrocarbon having at least two carbon atoms to 50 carbon atoms (C$_2$-C$_{50}$), such as two to 25 carbon atoms (C$_2$-C$_{25}$), or two to ten carbon atoms (C$_2$-C$_{10}$), and at least one carbon-carbon double bond, wherein the unsaturated monovalent hydrocarbon can be derived from removing one hydrogen atom from one carbon atom of a parent alkene. An alkenyl group can be branched, straight-chain, cyclic (e.g., cycloalkenyl), cis, or trans (e.g., E or Z).

Alkoxy: —O-alkyl, —O-alkenyl, or —O-alkynyl, with exemplary embodiments including, but not limited to, methoxy, ethoxy, n-propoxy, isopropoxy, n-butoxy, t-butoxy, sec-butoxy, n-pentoxy.

Alkyl: A saturated monovalent hydrocarbon having at least one carbon atom to 50 carbon atoms (C$_1$-C$_{50}$), such as one to 25 carbon atoms (C$_1$-C$_{25}$), or one to ten carbon atoms ($C_1$-$C_{10}$), wherein the saturated monovalent hydrocarbon can be derived from removing one hydrogen atom from one carbon atom of a parent compound (e.g., alkane). An alkyl group can be branched, straight-chain, or cyclic (e.g., cycloalkyl).

Alkynyl: An unsaturated monovalent hydrocarbon having at least two carbon atoms to 50 carbon atoms ($C_2$-$C_{50}$), such as two to 25 carbon atoms ($C_2$-$C_{25}$), or two to ten carbon atoms ($C_2$-$C_1$), and at least one carbon-carbon triple bond, wherein the unsaturated monovalent hydrocarbon can be derived from removing one hydrogen atom from one carbon atom of a parent alkyne. An alkynyl group can be branched, straight-chain, or cyclic (e.g., cycloalkynyl).

Amide: —C(O)NR$^b$R$^c$ wherein each of R$^b$ and R$^c$ independently is selected from hydrogen, aliphatic, heteroaliphatic, aryl, heteroaryl, or any combination thereof.

Amine: —NR$^b$R$^c$, wherein each of R$^b$ and R$^c$ independently is selected from hydrogen, alkyl, alkenyl, alkynyl, aryl, heteroalkyl, heteroalkenyl, heteroalkynyl, heteroaryl, and any combination thereof.

Aromatic: A cyclic, conjugated group or moiety of, unless specified otherwise, from 5 to 15 ring atoms having a single ring (e.g., phenyl) or multiple condensed rings in which at least one ring is aromatic (e.g., naphthyl, indolyl, or pyrazolopyridinyl); that is, at least one ring, and optionally multiple condensed rings, have a continuous, delocalized π-electron system.

Typically, the number of out of plane π-electrons corresponds to the Hückel rule (4n+2). The point of attachment to the parent structure typically is through an aromatic portion of the condensed ring system. For example,

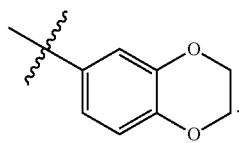

However, in certain examples, context or express disclosure may indicate that the point of attachment is through a non-aromatic portion of the condensed ring system. For example,

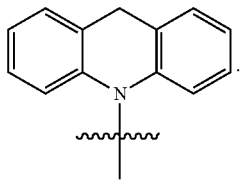

An aromatic group or moiety may comprise only carbon atoms in the ring, such as in an aryl group or moiety, or it may comprise one or more ring carbon atoms and one or more ring heteroatoms comprising a lone pair of electrons (e.g. S, O, N, P, or Si), such as in a heteroaryl group or moiety. Aromatic groups may be substituted with one or more groups other than hydrogen, such as aliphatic, heteroaliphatic, haloaliphatic, haloheteroaliphatic, aromatic, or an organic functional group.

Aryl: An aromatic carbocyclic group comprising at least five carbon atoms to 15 carbon atoms ($C_5$-$C_{15}$), such as five to ten carbon atoms ($C_5C_{10}$), having a single ring or multiple condensed rings, which condensed rings can or may not be aromatic provided that the point of attachment to a remaining position of the compounds disclosed herein is through an atom of the aromatic carbocyclic group.

Carboxyl: —C(O)OR$^b$, wherein R$^b$ is alkyl, alkenyl, alkynyl, aryl, heteroalkyl, heteroalkenyl, heteroalkynyl, heteroaryl, hydrogen, and any combination thereof.

Click Chemistry: A chemical synthetic method for making compounds using reagents that can be joined together using efficient reagent conditions and that can be performed in benign solvents or solvents that can be removed or extracts using facile methods, such as evaporation, extraction, or distillation. In some embodiments, click chemistry encompasses [3+2] cycloadditions, thiol-ene reactions, Diels-Alder reactions, inverse electron demand Diels-Alder reactions, [4+1] cycloadditions, nucleophilic substitution of small, strained rings (e.g., epoxide, azirdine, or the like), dihydroxylations, or any combinations thereof.

Clickable Functional Group: A functional group that can be used in click chemistry to form a product. In some embodiments, a clickable functional group can be selected from, but is not limited to, an azide or an alkyne.

Coordinating Functional Group: A functional group attached to an atom of a discrete ring system that facilitates and helps to direct reaction chemistries within a cavity of a nanohoop in which the discrete ring system is included. The cavity is defined by rings of the nanohoop skeleton as illustrated in the exemplary nanohoop compound embodiment illustrated below. Exemplary coordinating functional groups can include electron-donating and/or electron-accepting groups, with particular examples including carboxylic acids (or anions thereof), alkynes, and azides.

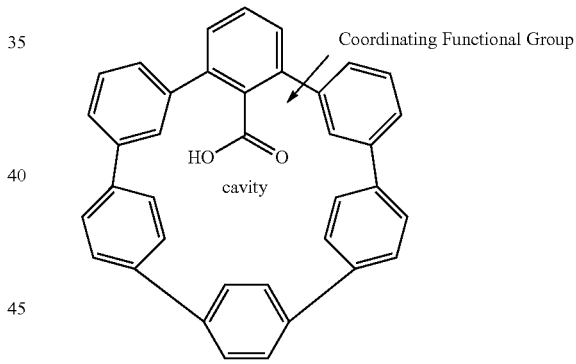

Discrete Ring System: A ring system comprising at least one aromatic ring having a meta-substitution pattern wherein bonds of the at least one aromatic ring that bind the aromatic ring to other rings in the nanohoop compound and/or other rings of the discrete ring system are positioned meta relative to one another. Formulas and structures of exemplary discrete ring system embodiments are provided herein.

Electron-Accepting Group (EAG): A functional group capable of accepting electron density from the ring to which it is directly attached, such as by inductive electron withdrawal.

Electron-Donating Group (EDG): A functional group capable of donating at least a portion of its electron density into the ring to which it is directly attached, such as by resonance.

Ester: —C(O)OR$^b$, wherein R$^b$ is selected from alkyl, alkenyl, alkynyl, aryl, heteroalkyl, heteroalkenyl, heteroalkynyl, heteroaryl, and any combination thereof.

Halogen: An atom selected from fluoro, chloro, bromo, or iodo.

Heteroaliphatic: An aliphatic group comprising at least one heteroatom to 20 heteroatoms, such as one to 15 heteroatoms, or one to 5 heteroatoms, which can be selected from, but not limited to oxygen, nitrogen, sulfur, selenium, phosphorous, and oxidized forms thereof within the group.

Heteroalkyl/Heteroalkenyl/Heteroalkynyl: An alkyl, alkenyl, or alkynyl group (which can be branched, straight-chain, or cyclic) comprising at least one heteroatom to 20 heteroatoms, such as one to 15 heteroatoms, or one to 5 heteroatoms, which can be selected from, but not limited to oxygen, nitrogen, sulfur, selenium, phosphorous, and oxidized forms thereof within the group.

Heteroaryl: An aryl group comprising at least one heteroatom to six heteroatoms, such as one to four heteroatoms, which can be selected from, but not limited to oxygen, nitrogen, sulfur, selenium, phosphorous, and oxidized forms thereof within the ring. Such heteroaryl groups can have a single ring or multiple condensed rings, wherein the condensed rings may or may not be aromatic and/or contain a heteroatom, provided that the point of attachment is through an atom of the aromatic heteroaryl group.

Interlocked Molecules: Molecular structures that are formed from two or more separate molecular components, such as a nanohoop compound and a separate molecule, that are associated such that a portion of the separate molecule is spatially confined within a cavity of the nanohoop compound. For example, the associated molecular components need not be connected together through chemical bonds (e.g., covalent bonds) but they can be associated such that they cannot be separated without breaking one or more chemical bonds (e.g., covalent bonds) of at least one of the separate molecular components. Exemplary interlocked molecules can include, but are not limited to, catenanes, rotaxanes, and the like, wherein at least one of the molecular components is a nanohoop compound as described herein.

Ketone: —C(O)$R^b$, wherein $R^b$ is selected from aliphatic, heteroaliphatic, aryl, heteroaryl, and any combination thereof.

Molecular machines: An assembly of molecular components that are designed to perform machine-like movements in response to specific external stimuli. In some embodiments, molecular machines are synthetic structures that can convert chemical energy into mechanical motion and forces. In some embodiments, molecular components that form the molecular machines are interlocked molecules as described herein. Exemplary molecular machines can include, but are not limited to, molecular motors, molecular propellers, molecular switches, and the like.

Nanohoop Compound: A compound organized to form a hoop-like structure, the compound comprising one or more discrete ring systems as defined herein. In some embodiments, nanohoop compounds comprise one or more discrete ring systems that satisfy Formula II (and/or Formulas IIA-IIC) disclosed herein and wherein at least one ring of the discrete ring system comprises meta-positioned bonds to other rings of the nanohoop compound and/or other rings of the discrete ring system, such as is illustrated in the exemplary structure below (where X is a heteroatom or a carbon atom comprising a coordinating functional group) and wherein the compound further comprises para-linked aromatic groups connected to the one or more discrete ring systems.

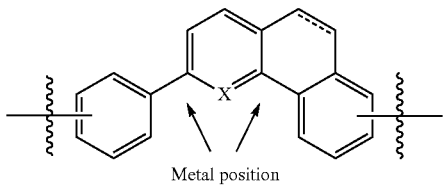

Metal position

Quaternary Amine: —N+$R^b R^c R^d$, wherein each of $R^b$, $R^c$, and $R^d$ independently are selected from hydrogen, aliphatic, heteroaliphatic, aryl, heteroaryl, and any combination thereof.

Sulfonyl/Sulfonate: —$SO_2 R^b$, wherein $R^b$ is selected from hydrogen, aliphatic, heteroaliphatic, aryl, heteroaryl, and any combination thereof.

A person of ordinary skill in the art would recognize that the definitions provided above are not intended to include impermissible substitution patterns (e.g., methyl substituted with 5 different groups, and the like). Such impermissible substitution patterns are easily recognized by a person of ordinary skill in the art. In formulas and specific compounds disclosed herein, a hydrogen atom is present and completes any formal valency requirements (but may not necessarily be illustrated) wherever a functional group or other atom is not illustrated. For example, a phenyl ring that is drawn as

comprises a hydrogen atom attached to each carbon atom of the phenyl ring other than the "a" carbon, even though such hydrogen atoms are not illustrated.

Any functional group disclosed herein and/or defined above can be substituted or unsubstituted, unless otherwise indicated herein.

Abbreviations

CNT: Carbon nanotube(s)

[X]CPP: Cycloparaphenylene (wherein X represents an integer corresponding to the number of aryl rings present in the cycloparaphenylene).

DCM: Dichloromethane

NMR: Nuclear magnetic resonance

II. INTRODUCTION

Materials and molecules with extended π-conjugation, such as graphene, carbon nanotubes (or CNTs), fullerene, and the like, have been a primary research focus in numerous disciplines ranging from physics to biology. These materials and molecules have a range of properties, such as electrical conductivity, chirality, fluorescence, tunable redox chemistry, smooth pi-rich surfaces, and the like, which can play a significant role in the design of advanced molecular machines. For example, the smooth π-rich surface of CNTs is known for enabling frictionless or a substantially low friction movement between interacting components. This property has been used in a radially-oriented, fully conjugated macrocyclic CNT fragment to generate a high-spinning molecular bearing, which is a basic component of numerous macroscopic machines. However, synthetic methods to obtain interlocked structures are currently underdeveloped and there are limited examples of macrocyclic compounds that can be used in such structures.

The present disclosure describes nanohoop compound embodiments that have structures and properties that facilitate their use in interlocked structures and further that facilitate use of the nanohoop compounds in a variety of other chemistries. In particular embodiments, the nanohoop compounds of the present disclosure comprise one or more discrete ring systems, wherein at least one discrete ring system comprises an aromatic ring having a unique meta-substituted motif that affords a strained cavity in the nanohoop compound in which myriad reaction chemistries can take place. In some embodiments, nanohoop compound embodiments can further comprise a heteroatom and/or coordinating functional group within the discrete ring system that can facilitate reactions occurring in the cavity.

III. NANOHOOP COMPOUND EMBODIMENT AND METHODS

Disclosed herein are embodiments of a compound that adopts a unique nanostructure, such as a hoop-shaped structure. The compound embodiments disclosed herein exhibit a radially oriented π-system, and comprise one or more discrete ring systems present in the nanohoop. The discrete ring system is connected to the other rings of the nanohoop compound in a manner such that the discrete ring system is orientated substantially perpendicular to the radius of the nanohoop as defined by the other rings making up the nanohoop. The discrete ring system therefore includes ring atoms that do not sit in the same plane as the ring atoms of other rings making up the nanohoop. In some embodiments, the one or more discrete ring systems included in the nanohoop comprise at least one aromatic ring that is connected to other rings within the nanohoop and/or other rings within the discrete ring system (such as in systems comprising two or more fused or bound ring structures) via meta linkages wherein points of attachment of the aromatic ring are positioned meta relative to one another (that is, at least one atom is positioned between the atoms to which the two points of attachment are bound), whereas other rings in the nanohoop are connected via para linkages. A representative configuration is illustrated below. This illustration is merely provided as an example to show meta and para linkages and is not intended to be limiting with respect to the components of the nanohoop compounds described herein.

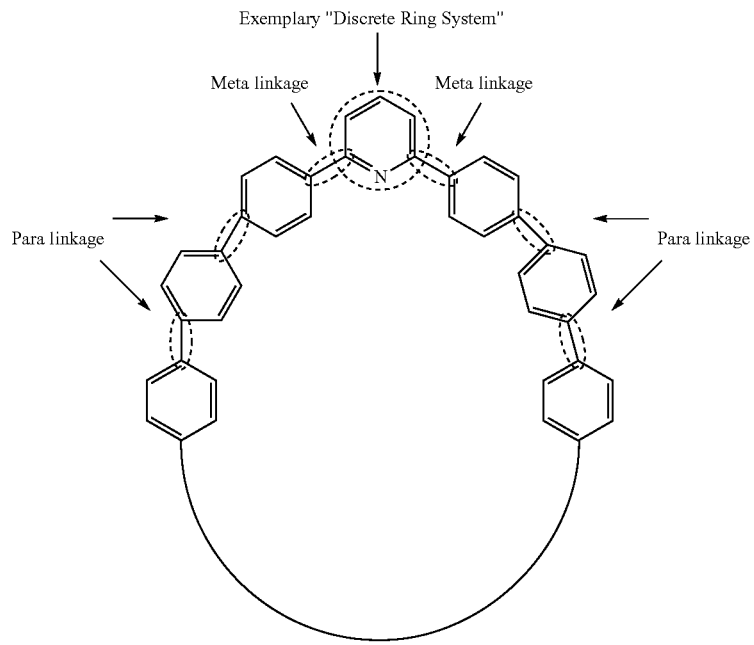

In yet some additional embodiments, the discrete ring system can comprise a plurality of rings that are fused together and wherein at least one of the fused rings is connected to the other rings and an aryl group of the nanohoop via meta-substituted bonds. In yet some additional embodiments, the discrete ring system can comprise a plurality of rings wherein each ring comprises a heteroatom, such as nitrogen or phosphorus. The unique hoop-like structures of the disclosed compound embodiments provide a unique electronic environment that can be utilized in a variety of chemical applications, such as those described herein.

In some embodiments, the nanohoop compounds can have structures satisfying Formula I, illustrated below.

Formula I

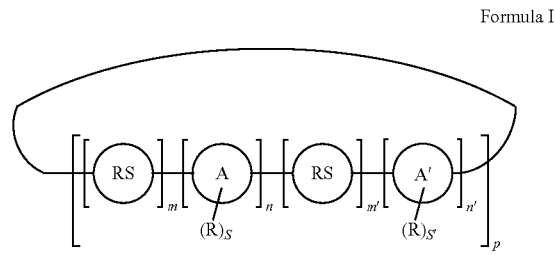

With reference to Formula I, the "hoop-shaped" nature of the compounds is represented by the solid curved line, which in turn represents a bond formed between a carbon atom of at least one discrete ring system (represented as "RS" in Formula I) and a carbon atom of an A or A' ring. The RS group is connected to the A or A' rings of the nanohoop in a manner such that one or more atoms of the RS group are oriented substantially perpendicular to the atoms of the A and/or A' rings. In some embodiments, the RS group is linked to A and/or A' rings via a meta linkage.

Also with reference to Formula I:

each A and/or each A' ring independently represents an aromatic ring that is separate (that is, distinct) from the RS group. In some embodiments, at least one A and/or A' group is bound to the RS group and another ring of the nanohoop via a para-linkage;

each R independently can be selected from hydrogen, an electron-donating group, an electron-accepting group, or any combinations thereof;

m can be an integer selected from 1 to 4, such as 1, 2, 3, or 4;

m' can be an integer selected from 0 to 4, such as 0, 1, 2, 3, or 4;

each s and s' can independently be an integer selected from 0 to 4, such as 0, 1, 2, 3, or 4;

each n and n' can independently be an integer selected from 0 to 24, such as 0 to 12, or 0 to 10, or 0 to 8 (e.g., 0, 1, 2, 3, 4, 5, 6, 7, 8, 9, 10, 11, 12, 13, 14, 15, 16, 17, 18, 19, 20, 21, 22, 23, or 24); and p can be integer selected from 1 to 20, such as, 1 to 15, or 1 to 10, or 1 to 5 (e.g., 1, 2, 3, 4, 5, 6, 7, 8, 9, 10, 11, 12, 13, 14, 15, 16, 17, 18, 19, or 20). In some embodiments, p is an integer selected from 1 to 8, such as 1, 2, 3, 4, 5, 6, 7, or 8.

In some embodiments, when more than one RS group is present, one RS group may be separated from another RS group by either an A ring or an A' ring. In some embodiments, when more than one RS group is present and n is 0, both RS groups may be coupled together within the nanohoop structure.

In some embodiments, when each of n' and m' is 0, then p is at least 6, and provided that when p is 1, then at least one of n, n' and m' is 5 or n, n', or m' independently are integers that when taken together add up to 5.

In some embodiments, each A ring or A' ring can independently be selected from aryl, aryl comprising an electron-accepting group and/or an electron-donating group, heteroaryl, or heteroaryl comprising an electron-accepting group and/or an electron-donating group.

Representative examples of A rings and A' rings include, but are not limited to, (i) phenyl; (ii) phenyl substituted with one or more electron-donating substituents described herein; (iii) a heteroaryl ring system having a structure satisfying a formula:

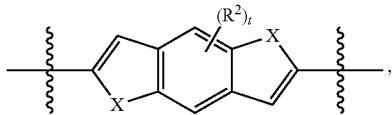

wherein X is selected from O, S, and $NR^b$ (wherein $R^b$ is selected from hydrogen, aliphatic, heteroaliphatic, aryl, heteroaryl, and any combination thereof), $R^2$ is selected from an electron-donating group disclosed herein, and t is 0, 1, or 2; (iv) phenyl substituted with one or more electron-accepting substituents described herein; or (v) pyridinyl substituted with an aliphatic or aryl group; or a ring system having a structure satisfying a formula:

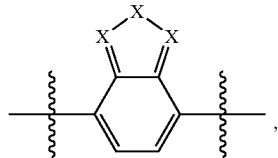

wherein each X independently is selected from O, S, N, or $NR^b$ wherein $R^b$ is selected from hydrogen, aliphatic, heteroaliphatic, aryl, heteroaryl, and any combination thereof).

In some embodiments, each A ring or A' ring independently can be selected from phenyl; benzo[1,2-b:4,5-b']dithiophenyl; benzo[1,2-b:4,5-b']dithiophenyl substituted with one or more electron-donating substituents described herein; benzo[1,2-b:4,5-b']difuranyl; benzo[1,2-b:4,5-b']difuranyl substituted with one or more electron-donating substituents described herein; 4,4-dimethyl-4H-cyclopenta[2,1-b:3,4-b']dithiophene; 4,4-dimethyl-4H-cyclopenta[2,1-b:3,4-b']dithiophene substituted with one or more electron-donating substituents described herein; 1,5-dihydropyrrolo[2,3-f]indolyl; 1,5-dihydropyrrolo[2,3-f]indolyl substituted with one or more electron-donating substituents described herein; benzo[c][1,2,5]thiadiazolyl; benzo[c][1,2,5]oxadiazolyl; or 2H-benzo[d][1,2,3]triazolyl.

With reference to the groups discussed above, and with reference to the R groups of Formula I, electron-donating groups can be selected from functional groups capable of donating at least a portion of its electron density into the ring to which it is directly attached, such as by resonance. Exemplary electron-donating groups can be selected from, but not limited to, one or more of the following: alkoxy, thioether, amide, amine, hydroxyl, thiol, acyloxy, aliphatic (e.g., alkyl, alkenyl, alkynyl), aryl, or combinations thereof. With reference to the groups discussed above, and with reference to the R groups of Formula I, electron-accepting groups can be selected from functional groups capable of accepting electron density from the ring to which it is directly attached, such as by inductive electron withdrawal. Exemplary electron-accepting groups can be selected from, but not limited to, one or more of the following: aldehyde, azide, ketone, ester, carboxylic acid, acyl, acyl halide, cyano, sulfonate, nitro, nitroso, quaternary amine, pyridinyl (or pyridinyl wherein the nitrogen atom is functionalized with an aliphatic or aryl group), alkyl halide, or combinations thereof.

Also, with reference to Formula I, the RS group can have a structure satisfying a Formula II:

Formula II

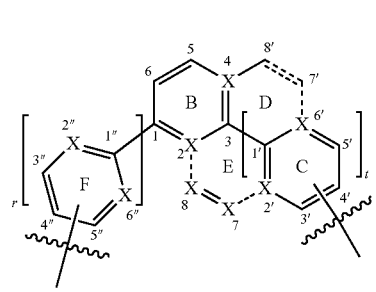

wherein each X can independently be selected from C, $C(R^1)$, N, P, C-CFG (wherein CFG represents a coordinating functional group), where $R^1$ is selected from an electron-accepting group, an electron-donating group, or any combinations thereof; and each of r and t independently can be 0 or 1. With reference to Formula II, integers are provided for reference to specific atoms within the discrete ring system. In some embodiments, the CFG is a carboxylic acid or an electron-accepting group or an electron-donating group, such as an azide or an alkyne (which also can function as a clickable functional group). In some embodiments, the RS group can have a structure satisfying one or more of the following formulas:

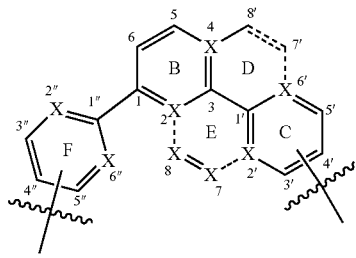

Formula IIA

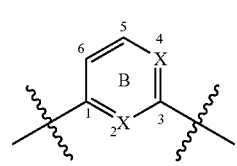

Formula IIB

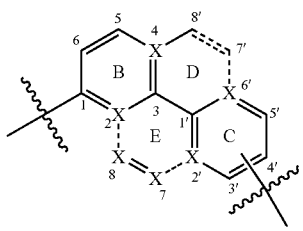

Formula IIC

In some embodiments, ring B is a heteroaryl ring wherein at least one X is a heteroatom (e.g., wherein X is N and ring B is a pyridinyl), or ring B is an aryl ring wherein at least one X is C-CFG. In some embodiments, ring B, together with ring C, can provide an two-ring aromatic ring system, such as a heterobiaryl ring system (e.g., bipyridinyl or biphosphinine); or ring B, together with rings C and D, can provide a three-ring fused aromatic ring system, such as a heteroaryl ring system (e.g., heterophenanthrene, such as 1,10-phenanthroline or phosphinino[3,2-h]phosphinoline); or ring B, together with rings C, D, and E, can provide a four-ring fused aromatic ring system, such a heteroaryl system (e.g., heteropyrene); or ring B, together with rings C and F, can provide a three-ring aromatic ring system, such as a heteroaryl system (e.g., 2, 2',2"-tripyridinyl or 2,2':6',2"-terphosphinine).

In certain embodiments, r and t are 0 and ring B is bonded to a para-positioned carbon atom of rings A or A' at C-1 and C-3. In some embodiments, the X at position 2 illustrated in Formula II is nitrogen or phosphorus and typically is nitrogen.

In certain embodiments, ring B is bound to ring C (and r is 0) to provide a hetero-biaryl RS group and in such embodiments, rings B and C are bound together at C-3 of ring B and C-1' of ring C and the RS group is further bonded to a para-positioned carbon atom of rings A or A' through C-1 of ring B and C-3' of ring C. In such embodiments, ring B typically is a pyridinyl ring. In certain embodiments, ring B is bound to rings C and D (and r is 0) to provide a three-ring fused RS group, such as a hetero-phenanthrene system. In such embodiments, ring D is bound to rings B and C at C-3 of ring B and C-1' of ring C and the fused RS group is further bonded to a para-positioned carbon atom of rings A or A' via C-1 of ring B and C-3' of ring C. In some disclosed embodiments, the X group of ring B at position 2 is a nitrogen atom, and the X group of ring C at the 2' position is a nitrogen atom.

In certain embodiments, ring B is bound with rings C, D and E (and r is 0) to provide a four-ring fused RS group, such as a heteropyrene system. In such embodiments, rings D and E are bound to rings B and C at C-3 of ring B and C-1' of ring C; ring D is bound to rings B and C at C-4 and C-6', respectively; and ring E is bound to rings B and C at C-2 and C-2', respectively. In some embodiments, the four-ring fused RS group can further be bound to ring F, wherein ring F comprises at least one X group that is nitrogen or phosphorus. In yet some additional embodiments, the four-ring fused RS group is bonded to a para-positioned carbon atom of rings A or A' via C-1 of ring B and C-3' of ring C.

In certain embodiments, ring B is bound with rings C and F to provide a three-ring aromatic RS group and in such embodiments, ring B may be bound together with ring C at C-3 of ring B and C-1' of ring C, and with ring F at C-1 of ring B and C-1" of ring F. In such embodiment, the RS group may be further bonded to a para-positioned carbon atom of rings A or A' at C-5" of ring F and C-3' of ring C, respectively. In another embodiment, the RS ring system may be further bonded to a para-positioned carbon atom of rings A or A' at C-4" of ring F and C-4' of ring C, respectively. In such embodiment, X may be positioned on any open position of rings B, C and F, respectively, such that X is located within the cavity of the nanohoop structure. In particular disclosed embodiment, X may be positioned at 6"-position of ring F, 2-position of ring B, and 2'-position of ring C, respectively. In another particular disclosed embodiment, X is positioned at 5"-position of ring F, 2-position of ring B, and 3'-position of ring C, respectively.

In particular disclosed embodiments, the nanohoop compounds can have structures satisfying any one of Formulas IIIA-IIIF below.

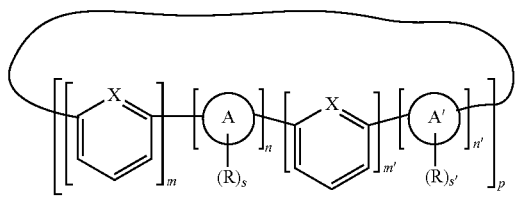

Formula IIIA

-continued
Formula IIIB
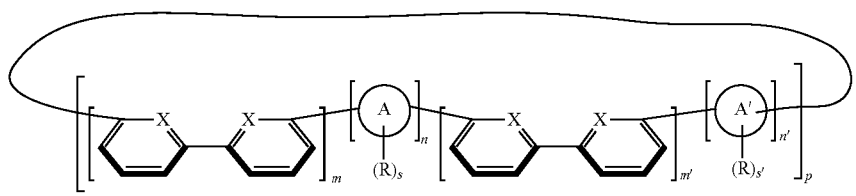
Formula IIIC
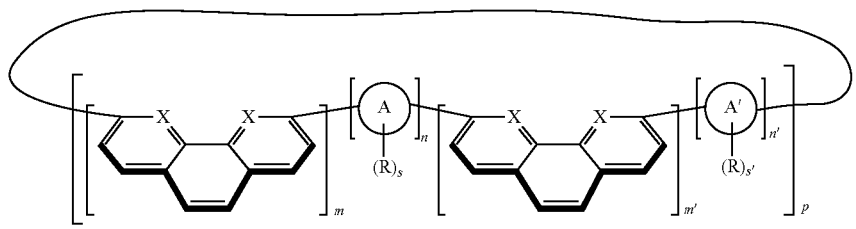
Formula IIID
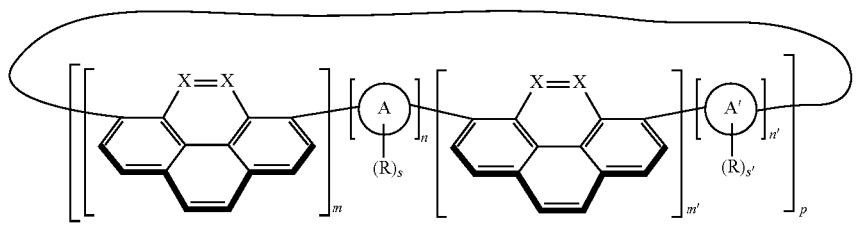
Formula IIIE
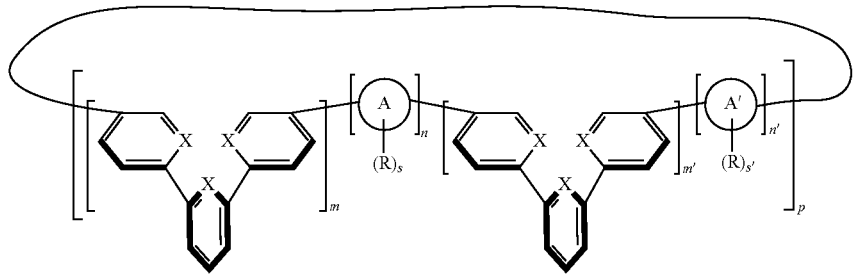
Formula IIIF
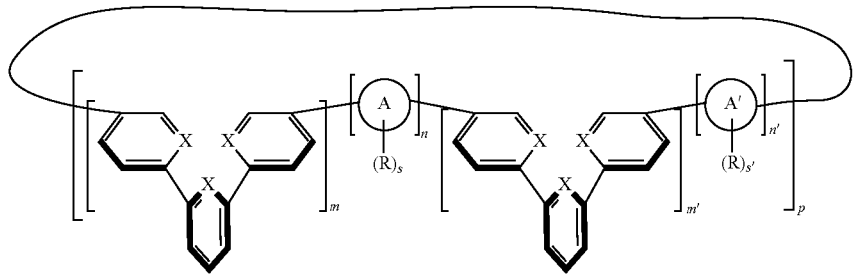

In some embodiments, the nanohoop compounds can be characterized as polydentate, such as monodentate, bidentate, tridentate, and the like, depending on the number of heteroatoms, such as nitrogen, phosphorus, and the like, that are present in the RS group of the nanohoop compounds. Exemplary nanohoop compounds can have structures satisfying Formulas IVA-IVC.

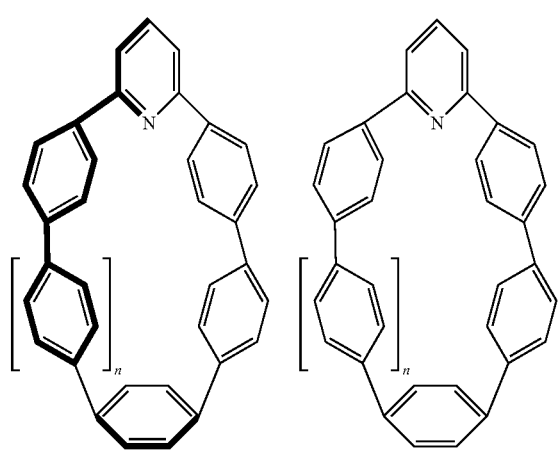

Monodentate, n = 1, 3-5

Formula IVA

Formula IVB

Bidentate, n = 1, 3-5

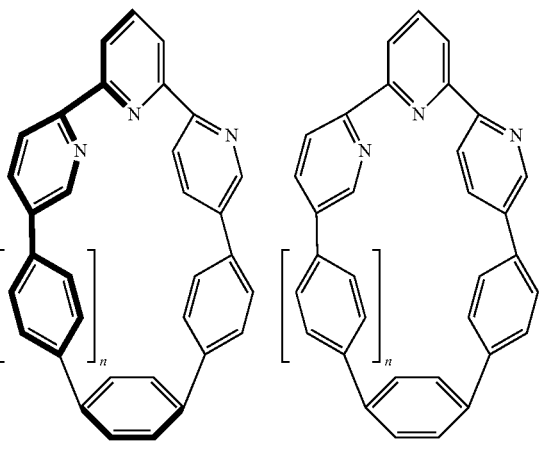

Formula IVC

Tridentate, n = 1, 3-5

Representative species of nanohoop compounds are provided below.

-continued
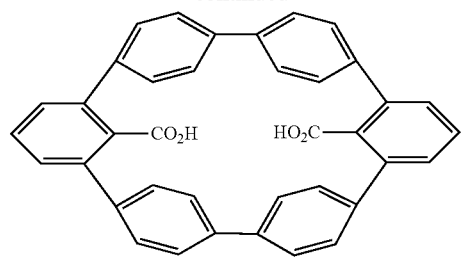
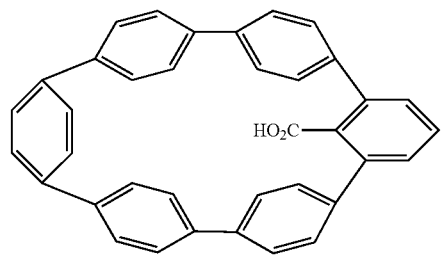
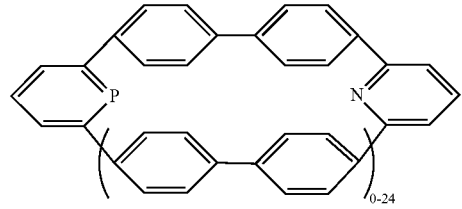
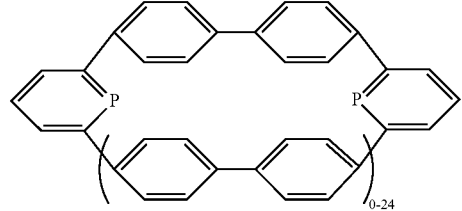
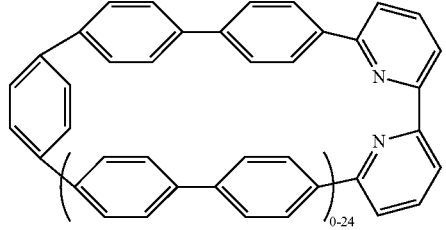
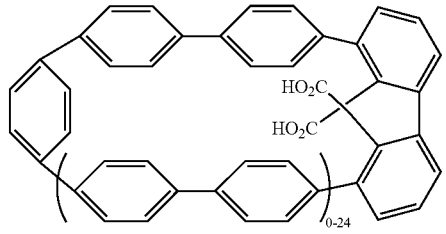
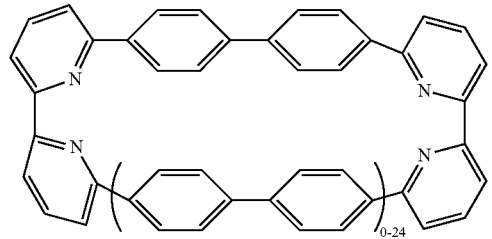
-continued
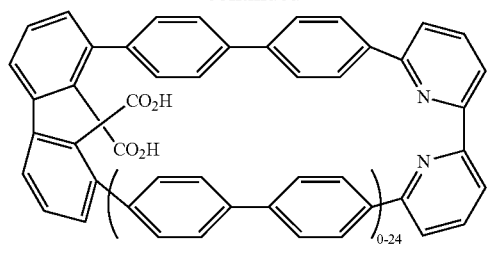
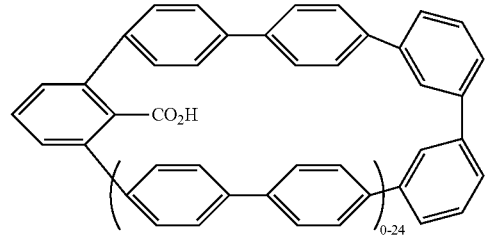
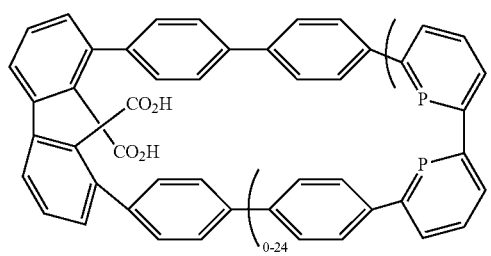
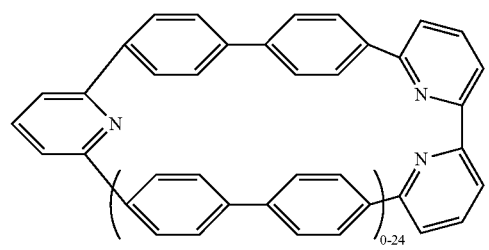
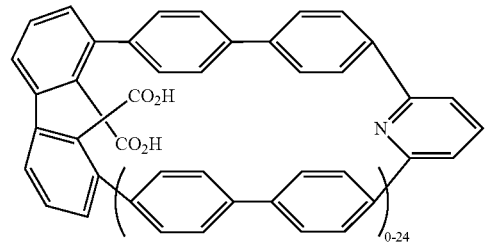
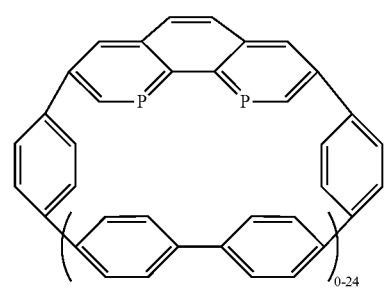

21
-continued
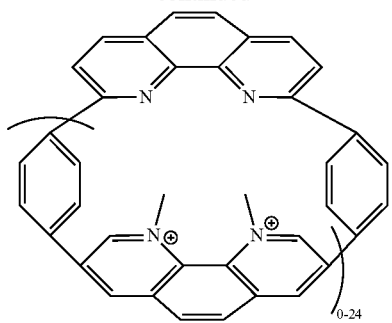
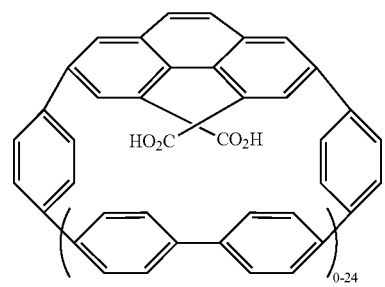
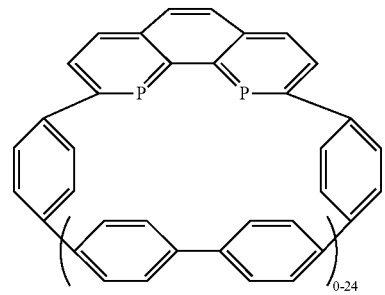
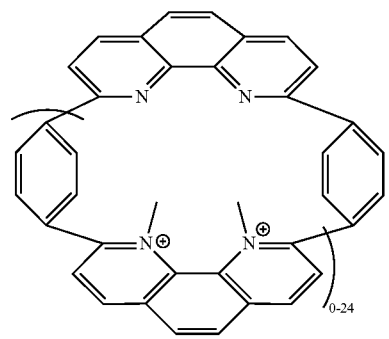
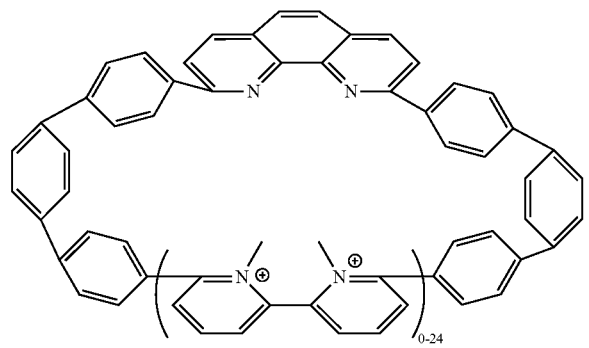
22
-continued
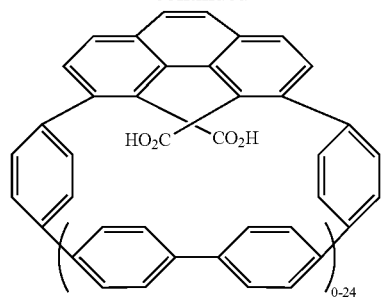
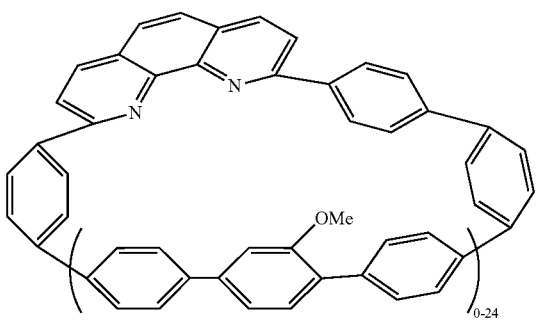
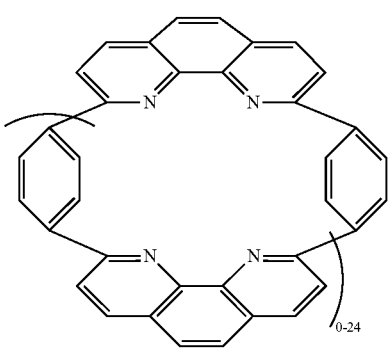
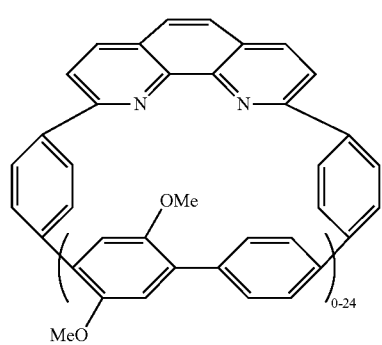
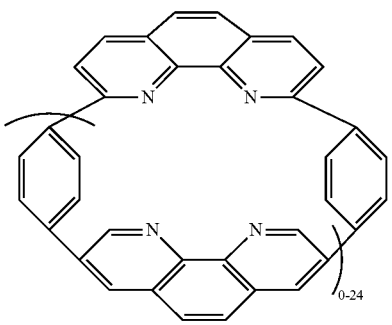

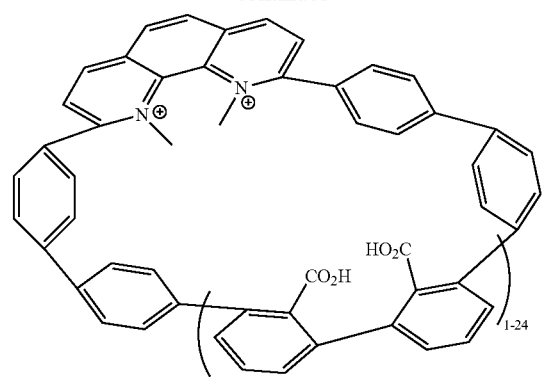
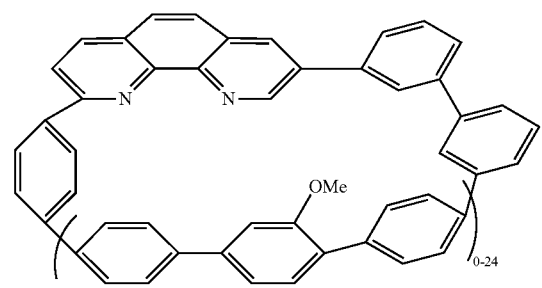
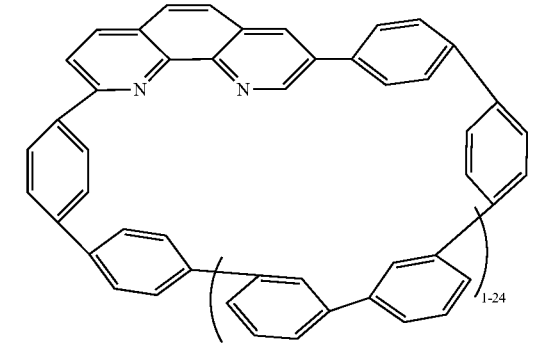
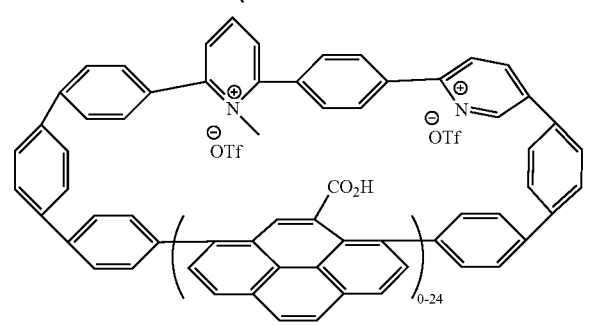
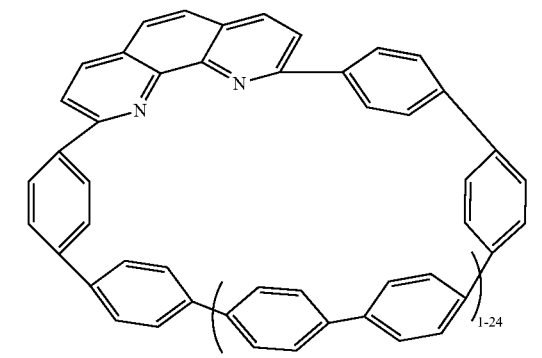
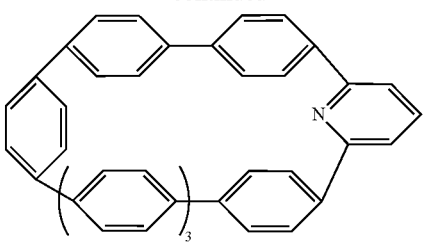
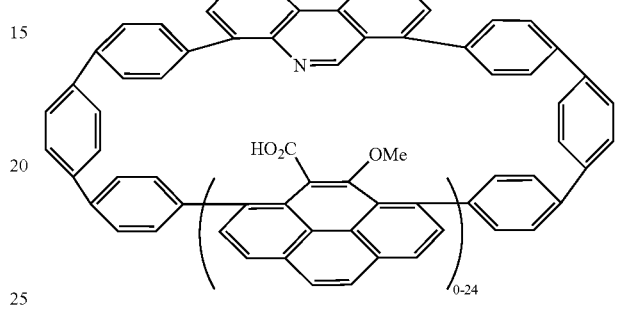
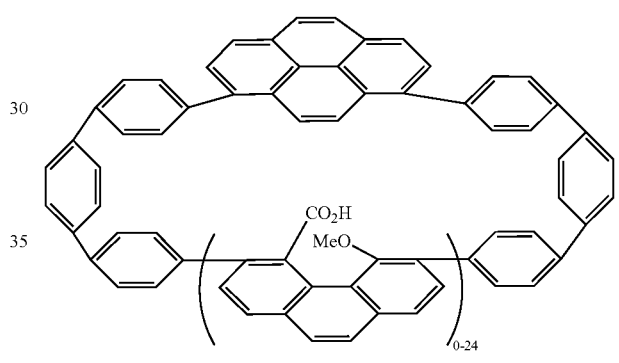
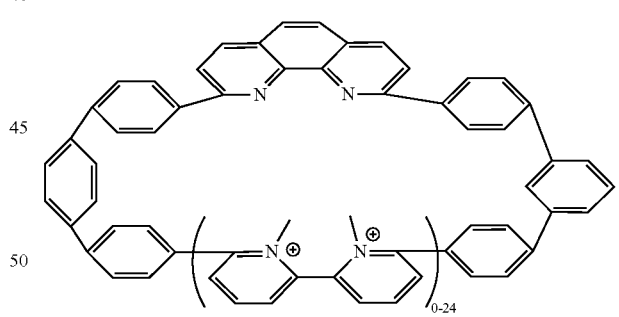
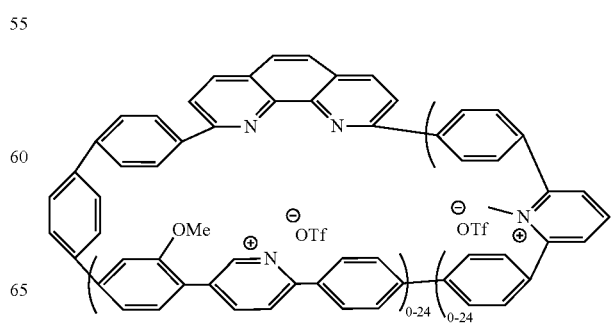

-continued
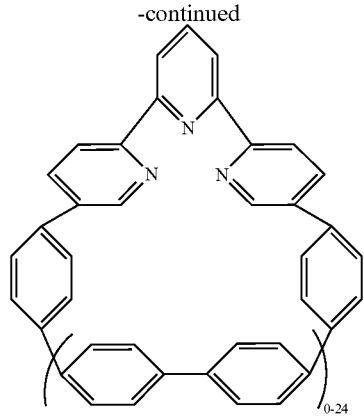
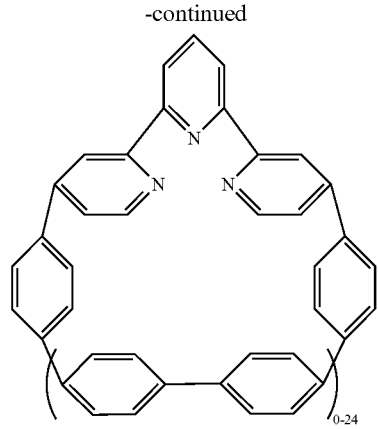
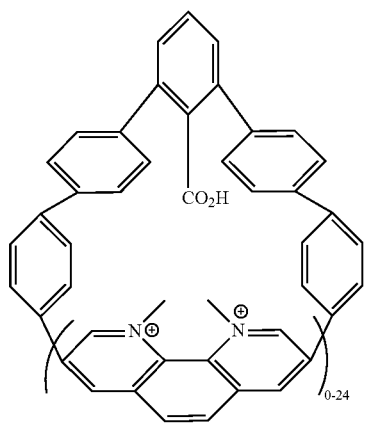
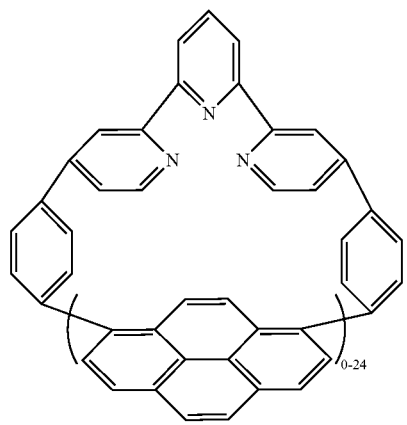
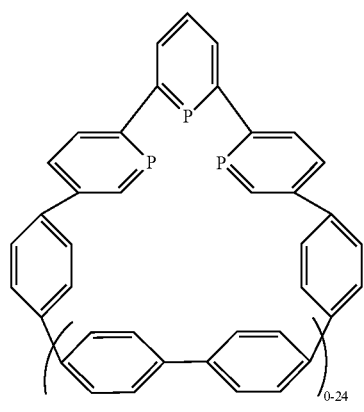
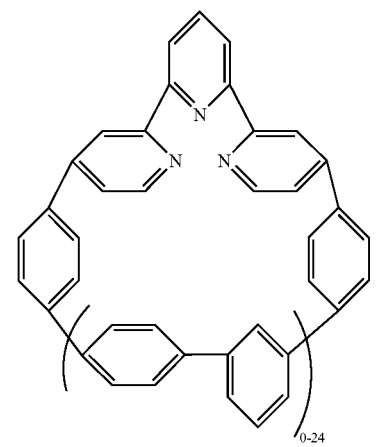
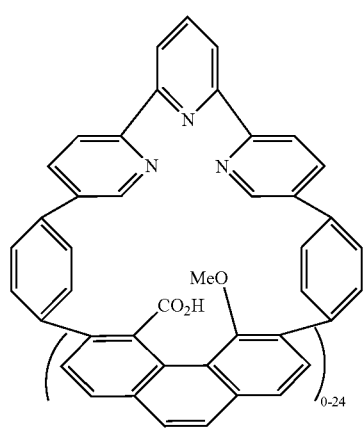
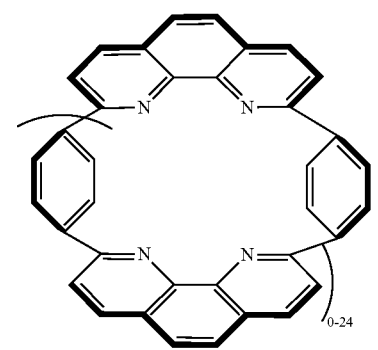

27
-continued
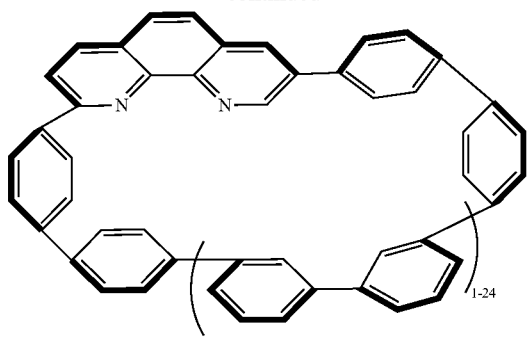
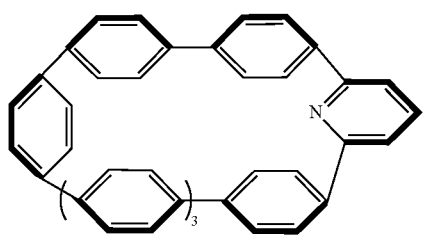
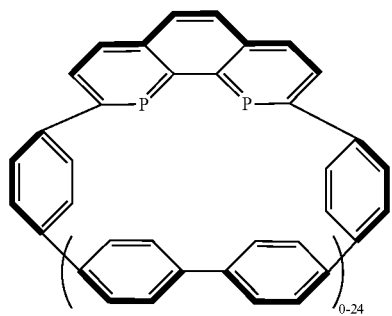
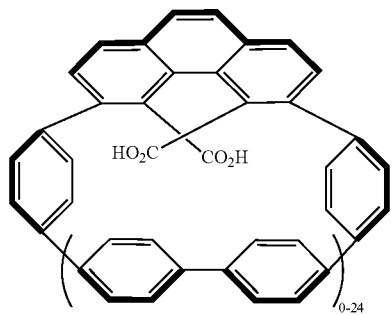
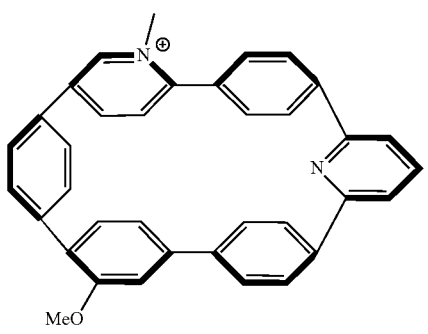
28
-continued
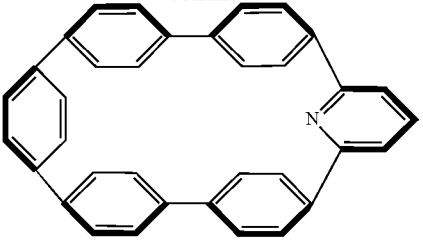
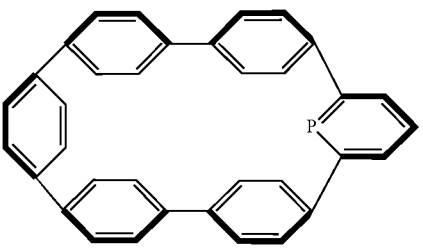
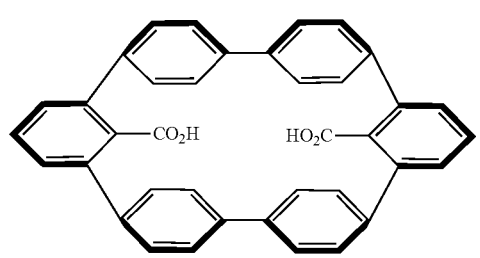
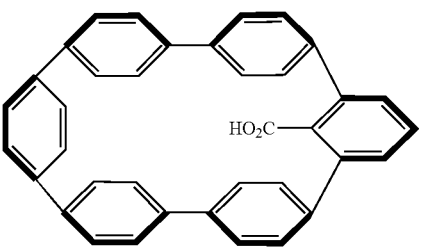
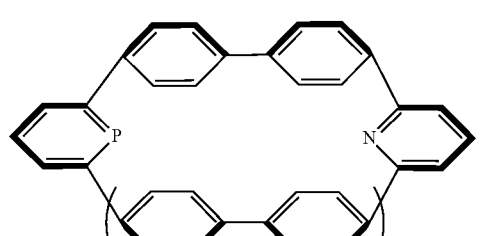
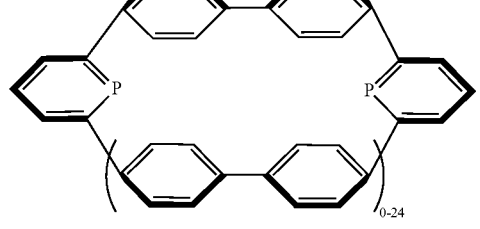

29
-continued
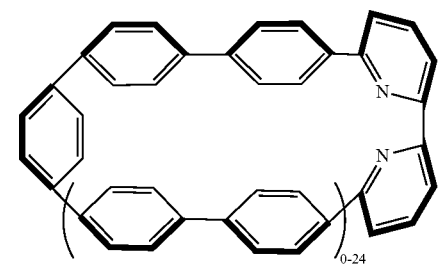
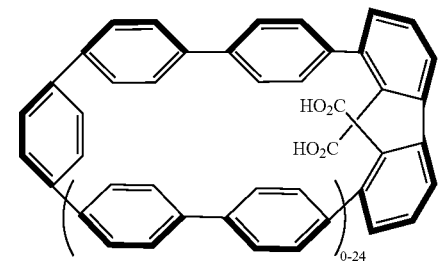
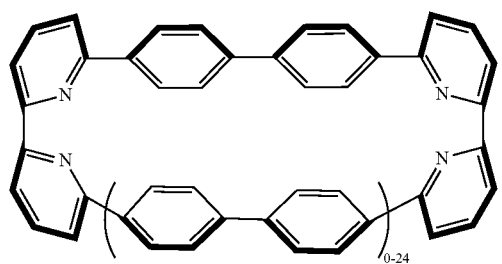
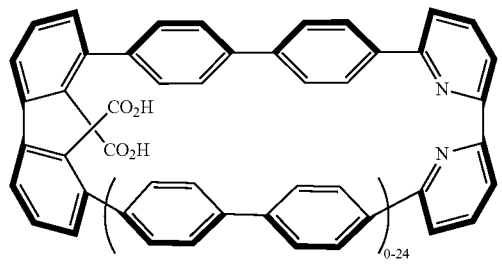
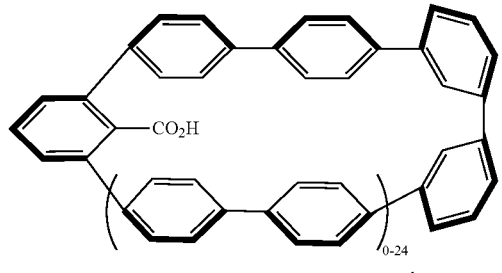
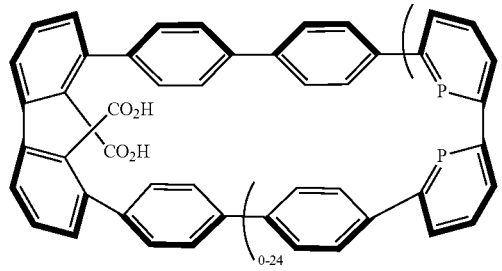
30
-continued
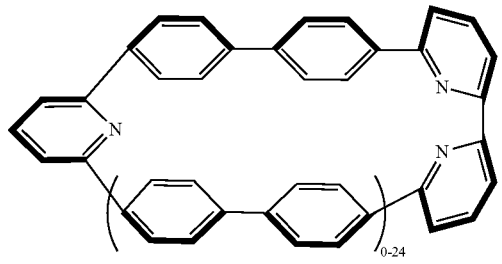
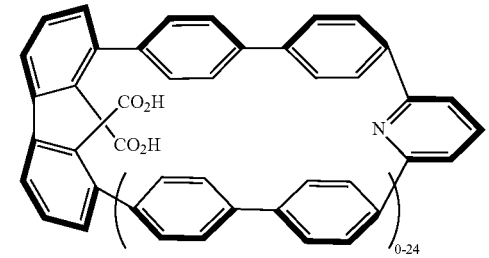
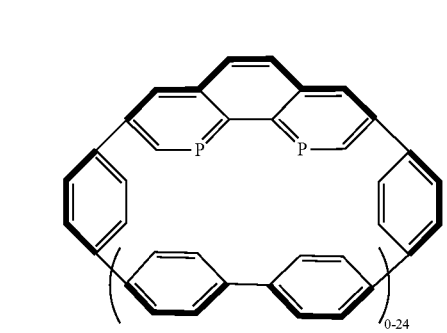
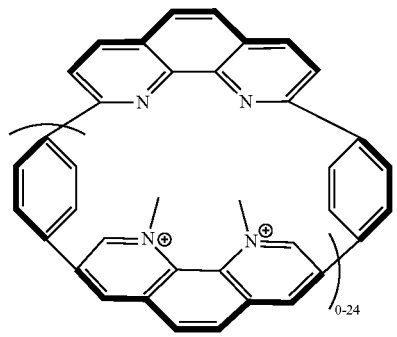
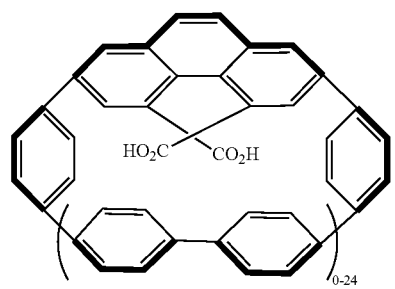

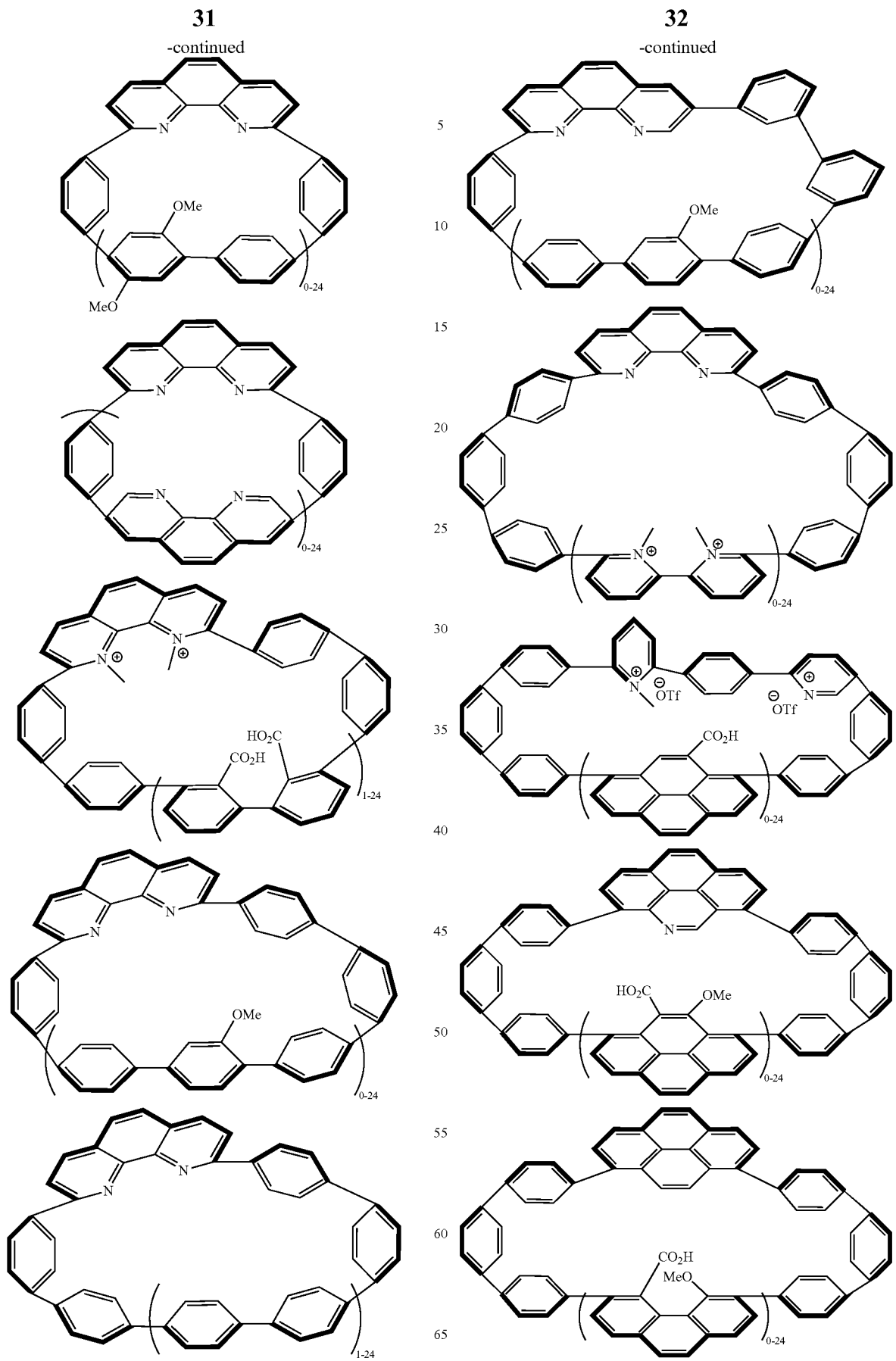

33
-continued
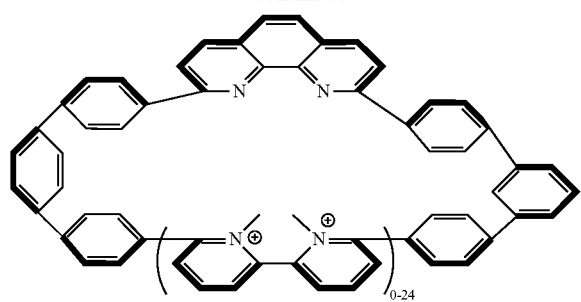
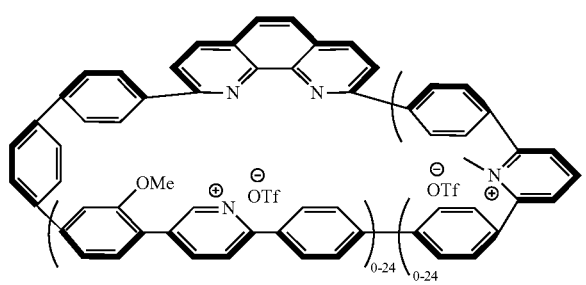
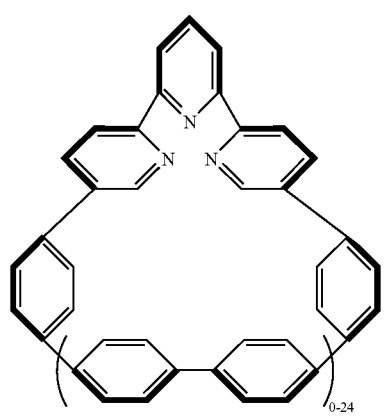
34
-continued
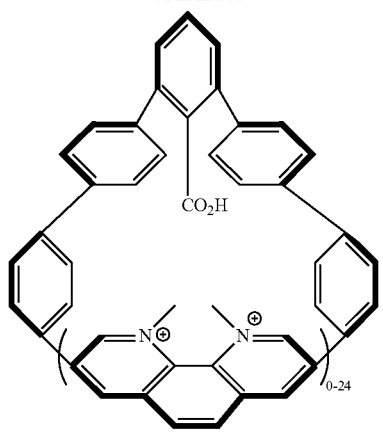
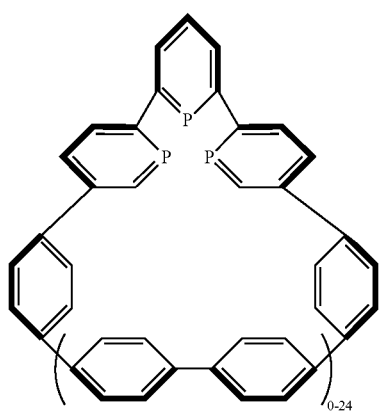
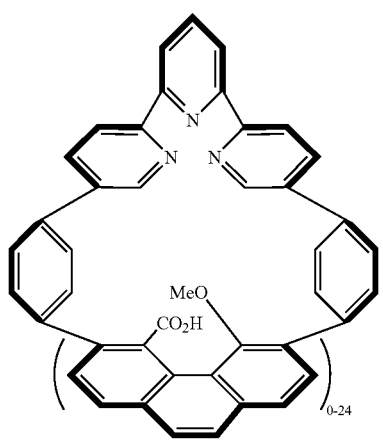

-continued

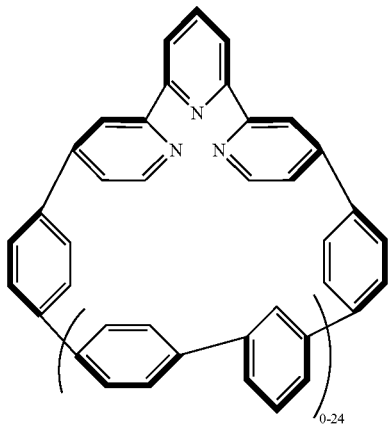

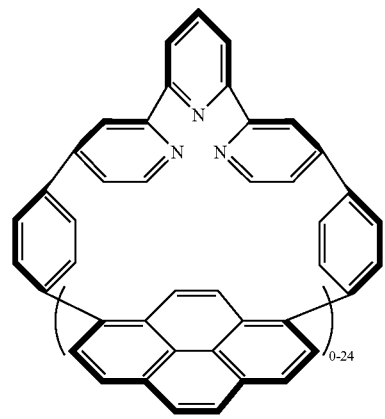

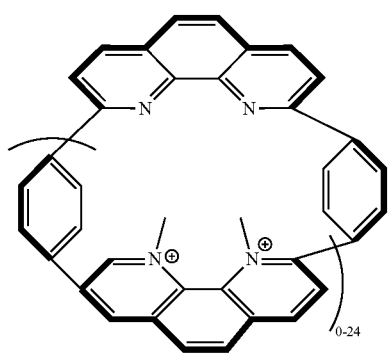

-continued

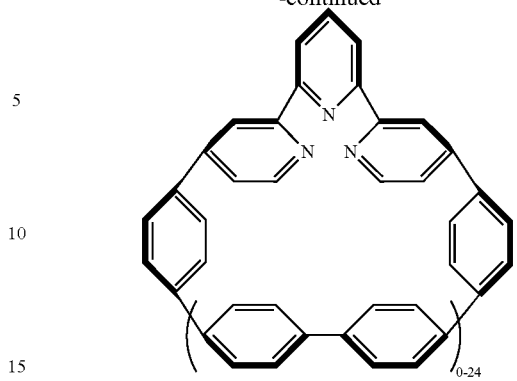

Methods of making nanohoop compounds are disclosed herein. Representative methods of making nanohoop compounds disclosed herein are illustrated below in the following schemes and also are discussed in the Examples section of the present disclosure.

In some embodiments, and as illustrated in Scheme 1, the synthesis of disclosed nanohoop compounds utilizes an intermediate macrocyclic "curved" fragment 106 comprising two cyclohexadiene moieties as "masked" aromatic (e.g., benzene) rings. These "masked" aromatic rings impart curvature and can subsequently be reduced to aromatic rings. Intermediate 104 can be obtained from a halogenated precursor compound 100 through a halogen-metal based coupling reaction in which halogenated precursor compound 100 is exposed to a base (e.g., lithium-containing base) and halogenated coupling partner 102. Intermediate 104, thus obtained, can subsequently be protected to obtain intermediate 106. In some embodiments, intermediate 104 can also be used as a starting material to produce cross-coupling intermediate 108 by forming a boronate ester from intermediate 104. As further illustrated in Scheme 1, additional A and A' rings can optionally be added to cross-coupling intermediate 108 using suitable cross-coupling reactions to produce boronate ester 110. Cross-coupling intermediate 108 and/or boronate ester 110 can then be cross-coupled with RS precursor 112 using suitable cross-coupling conditions, such as transition metal-mediated cross-couplings (e.g., Suzuki-Miyaura cross-coupling conditions) to obtain nanohoop intermediate 114. Nanohoop intermediate 114 can then be subjected to suitable aromatization conditions, such as tin-based aromatization conditions, and subsequent deprotection condition to obtain nanohoop compound 116. The curved geometry of these intermediates can provide sufficient strain energy for forming the desired nanohoop compound. In some embodiments, strain energy of the desired highly-strained nanohoop compound can be within a range from 25 kcal/mol to 120 kcal/mol. In one example, strain energy of the desired nanohoop compound can be 100 kcal/mol or more.

Scheme 1
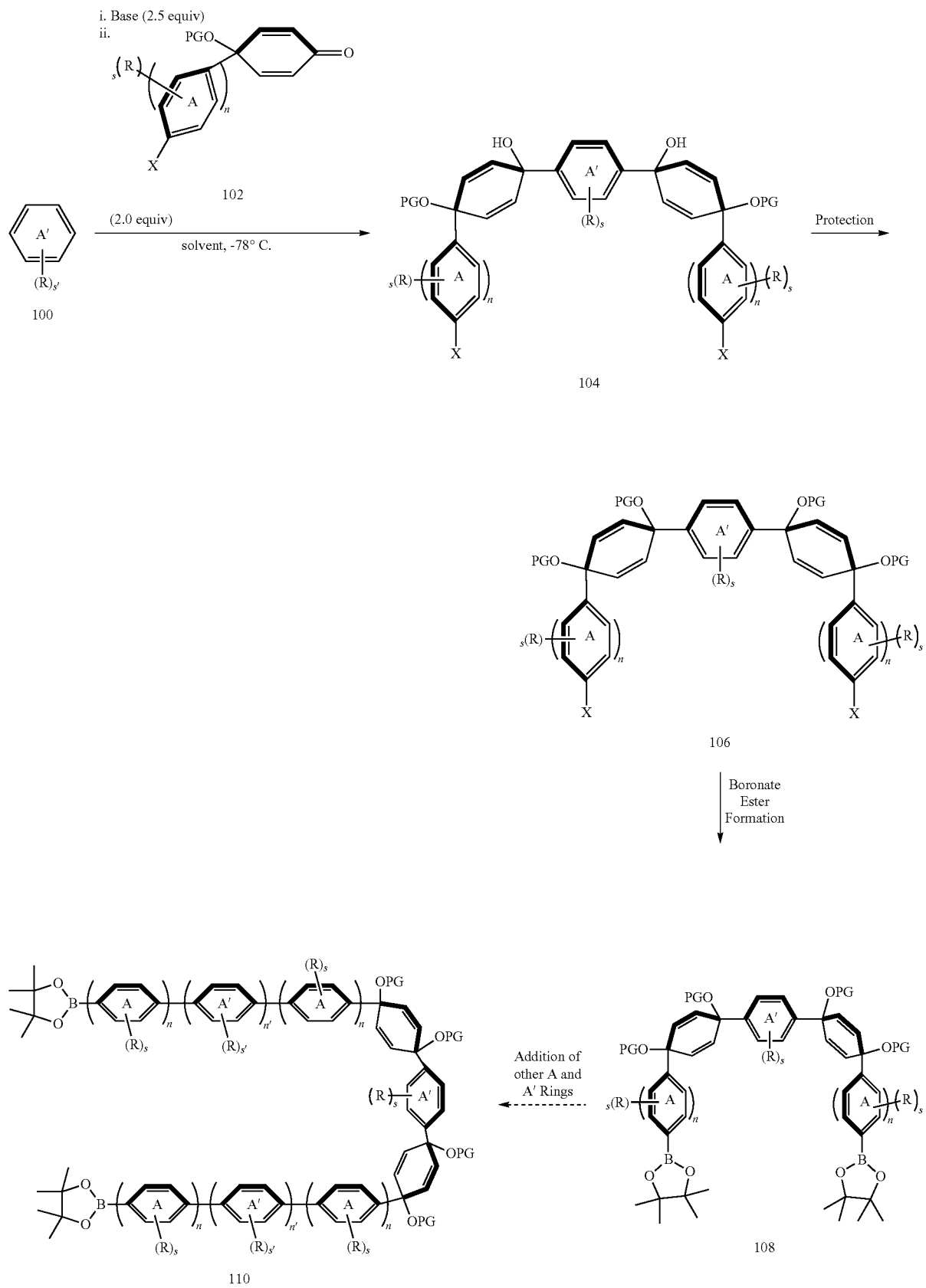

-continued
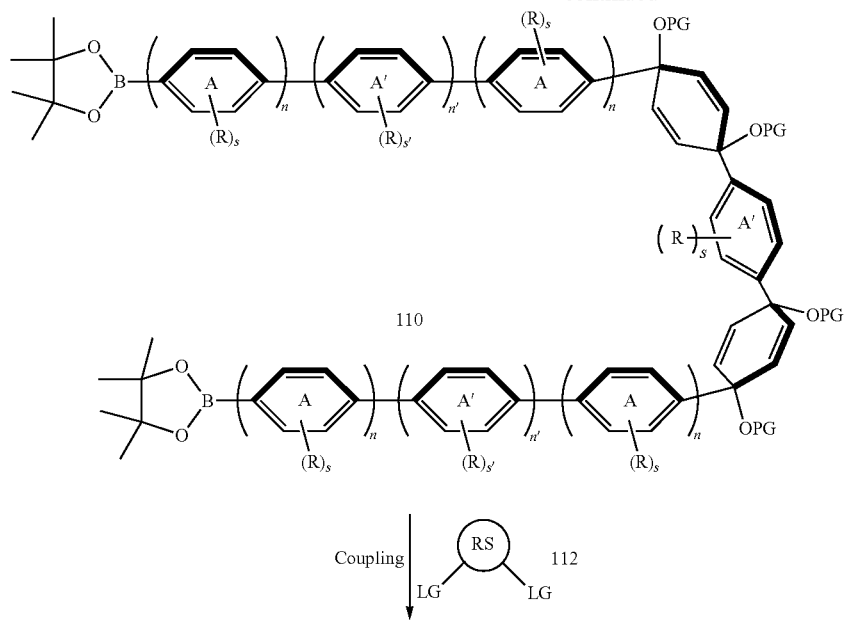
110
Coupling ↓ 112
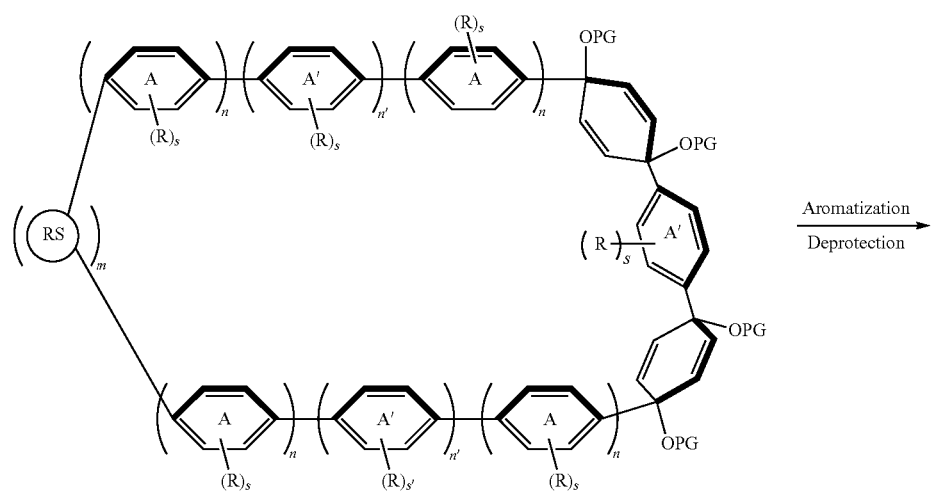
114
Aromatization
Deprotection -continued

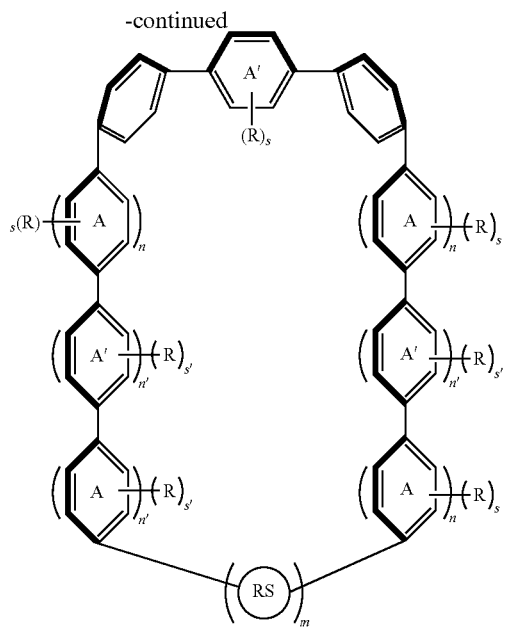

116

With reference to Scheme 1, each PG independently can be a protecting group selected from silyl protecting group (e.g., TES, TMS, TBS, TBDPS, TIPS, and the like), and each LG independently can be a leaving group selected from a halogen (e.g., fluoro, chloro, bromo, or iodo), a triflate, or other such leaving groups. The other variables in Scheme 1 above are as defined for the formulas described herein. The A and A' rings are drawn as phenyl rings solely by way of providing an exemplary NA' ring structure. A person of ordinary skill in the art, with the benefit of the present disclosure, will understand how to make other embodiments where A and/or A' are other aromatic ring systems.

An exemplary embodiment of the above-described method depicted in Scheme 1 is provided below in Scheme 2.

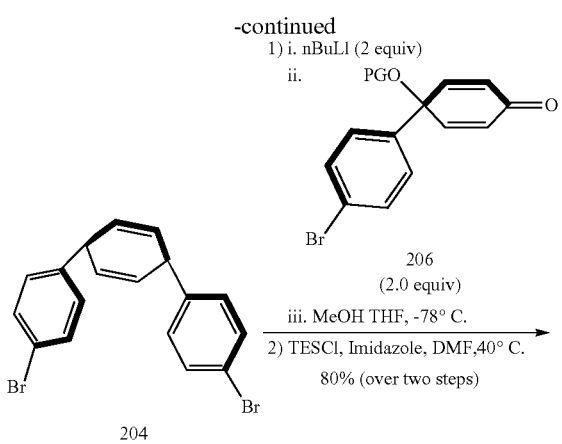

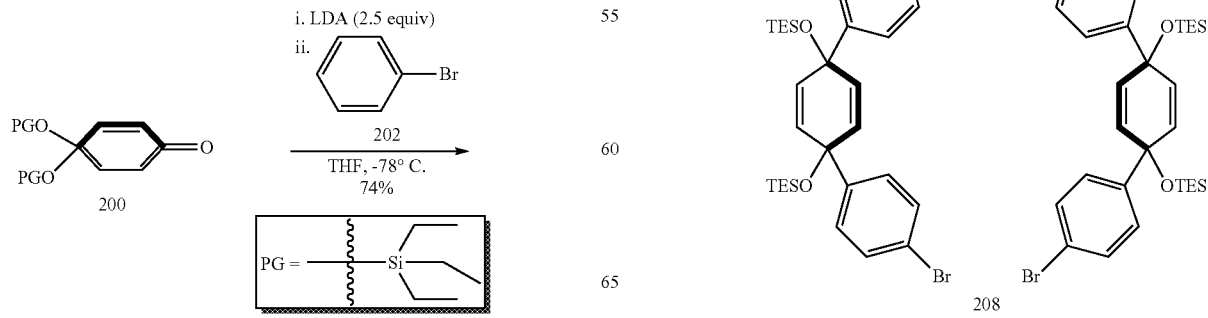

-continued

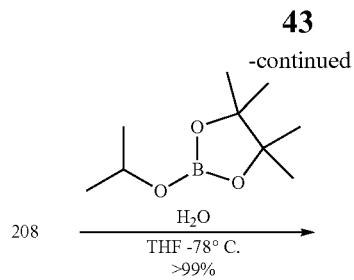

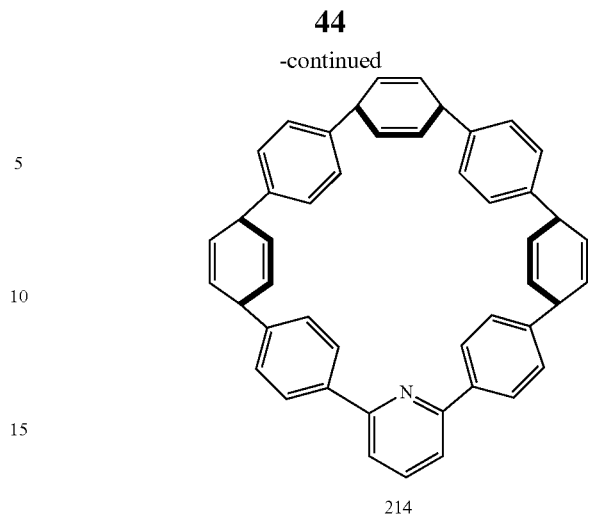

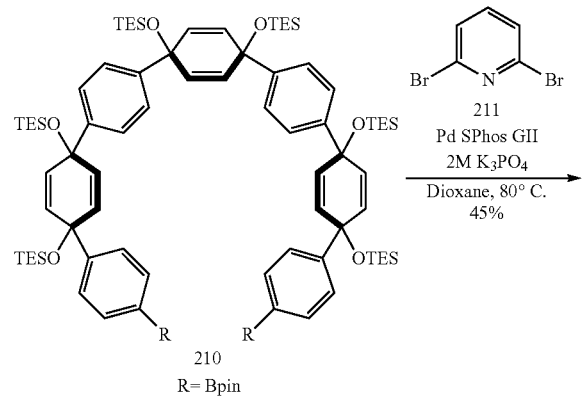

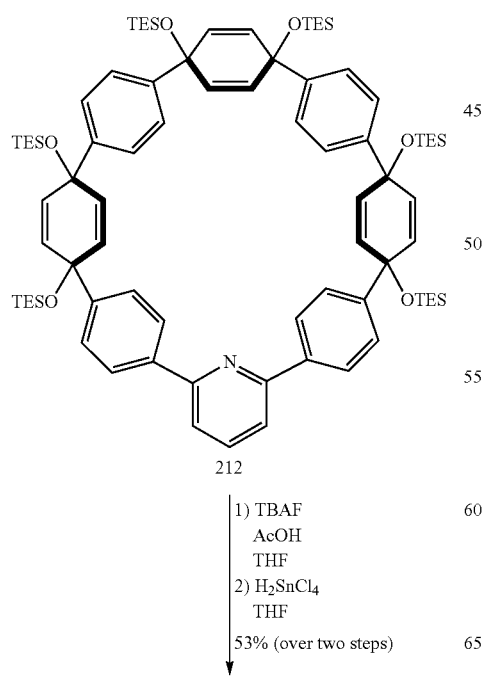

As illustrated in Scheme 2, when bromo benzene 202 (commercially available) is treated with quinol derivative 200 in the presence of lithium diisopropylamine (LDA), dibromide 204 is formed. Dibromide 204 is treated again with two equivalents of aryl quinol 206 to provide intermediate 208. Intermediate 208 can subsequently be converted to corresponding Suzuki-Miyaura cross-coupling partner 210 having two cyclohexadiene moieties that act as "masked" benzene rings. Suzuki-Miyaura cross-coupling partner 210 is coupled with RS precursor 211 to obtain macrocycle 212. Aromatization of the resulting free alcohol-containing macrocycle (obtained using a deprotection step) provides nanohoop compound embodiment 214, wherein the carbon atoms of the illustrated pyridine ring are oriented substantially perpendicular to the radius of the nanohoop.

Another exemplary embodiment of the above-described method is provided below in Scheme 3.

Scheme 3

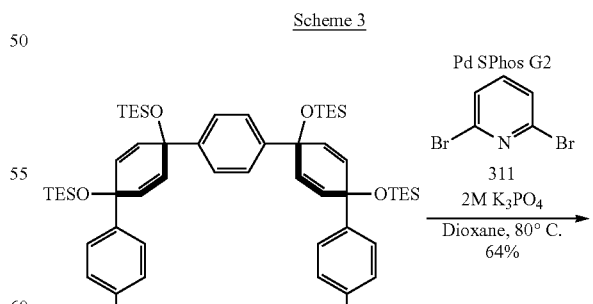

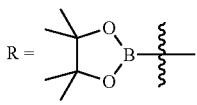

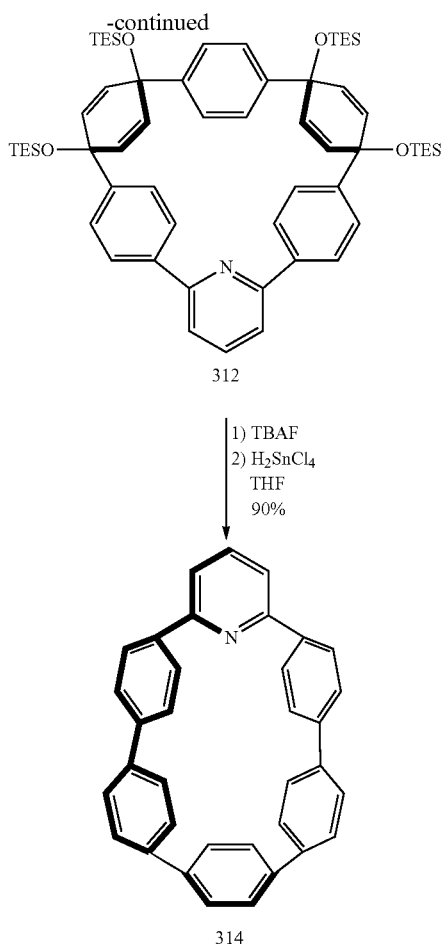

312

1) TBAF
2) H₂SnCl₄
   THF
   90%

314

As described above, the disclosed nanohoop compounds have unique structural features that facilitate their use in different applications, such as polymerization chemistry, host-guest chemistry, molecular shuttling, and/or sensing applications. In particular disclosed embodiments, the nanohoop compounds disclosed herein comprise a discrete ring system that causes the nanohoop compounds to adopt orientations that lend to their use in such applications. Solely by way of example, nanohoop compounds disclosed herein comprise at least one discrete ring system wherein at least one ring of the discrete ring system comprises atoms that are oriented substantially perpendicular to the radius of the nanohoop compound. In some embodiments, the discrete ring system is connected via meta linkages to other para-linked rings of the nanohoop structure, thereby forming a cavity within the nanohoop structure. In such embodiments, the meta-linked discrete ring system connected to the para-linked aryl rings in the nanohoop structure can distort packing of the nanohoop structure such that the major axis of the cavity between a meta-linked discrete ring system and a distal para-linked aryl ring is significantly larger than the minor axis of the cavity between two distal para-linked aryl rings. In some embodiments, the distance between the meta-linkage of the discrete ring system and a distal para-linked aryl ring in the nanohoop structure can be within a range from 5 Å to 25 Å, and the distance between two para-linked aryl rings can be within a range from 5 Å to 25 Å, depending on the number of the para-linked aryl rings present in the nanohoop structure. Additionally, in some embodiments, the size of the cavity of the nanohoop can be tuned by changing the number of para-linked aryl rings and/or the number of meta-linked discrete ring system, depending on the desired application of the nanohoop compound.

Exemplary applications of the nanohoop compound disclosed herein are described below.

In a representative embodiment, the nanohoop compounds of the present disclosure can act as ligands in metal complexes. In some embodiments, the nanohoop compounds combine with metal complexes having various molecular geometries, such as a tetrahedral geometry, a square planar geometry, or the like, to thereby form a metalated-nanohoop compound. In an exemplary embodiment, the nanohoop compound can be combined with any suitable metal complex, and the reaction can be monitored to a color change that is consistent with the formation of the metalated-nanohoop compound. Exemplary metal complexes can include, but are not limited to, [Pd(MeCN)₂](Cl₂), [Cu(MeCN)₄](PF₆), and the like. In an exemplary embodiment, nanohoop compound embodiment 214 can be reacted with palladium-complex to form a palladium-containing nanohoop compound 216, as illustrated in Scheme 4.

Scheme 4

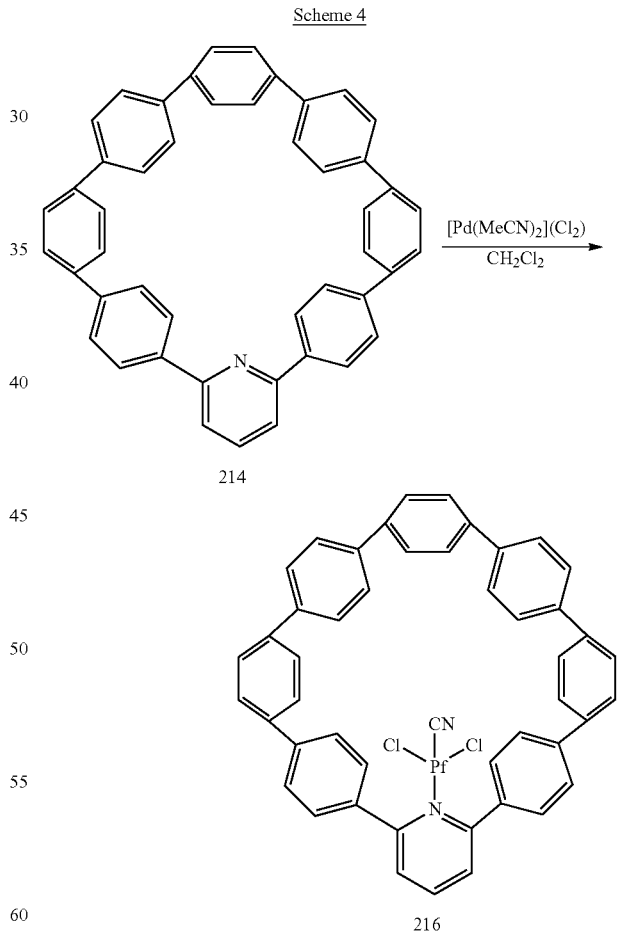

In some embodiments, the metalated-nanohoop compounds of the present disclosure can be used to make interlocked structures, like rotaxanes and catenanes. For example, the tunable redox properties of the nanohoop can stabilize the metal center disposed therein and influence the redox chemistry of the active metal center. Reduction and oxidation potentials of the nanohoop compounds can be tuned by the size of the hoop, as well as the presence of electron-accepting groups, or electron-donating aromatic rings in the hoop structure. Moreover, the nanohoop compounds are easier to reduce and oxidize, presumably due to narrower HOMO-LUMO gap, than their acyclic, unstrained counterparts. Further, in certain other embodiments, nanohoop compound embodiments comprising a metal can act as ligands where the metal can induce a degree of preorganization necessary for interlocking, and also can mediate covalent bond formation within the nanohoop structure. Thus, the metal disposed within the nanohoop compound can function as both a template and a catalyst for forming a covalent bond in a manner analogous to a conventional "active-template" reaction, thereby providing nanohoop-containing interlocked molecules. Exemplary nanohoop-containing interlocked molecules can include, but are not limited to, nanohoop-containing rotaxane, nanohoop-containing catenanes, or the like. The nanohoop-containing interlocked molecules can, in turn, be used as molecular machines. Exemplary nanohoop-containing molecular machines can include, but are not limited to, molecular rotors, molecular muscles, molecular switches, molecular motors, molecular shuttles, or the like.

In embodiments of nanohoop-containing rotaxane compounds, the method of making such compounds can comprise combining a metal catalyst with the nanohoop compound and an alkyne-containing compound and either a halogenated alkyne compound or an azide containing compound to provide the nanohoop rotaxane compound comprising an interlocked alkyne-containing compound or an interlocked triazole-containing compound constrained within a cavity of the nanohoop compound. The alkyne containing compound can have a structure satisfying a formula

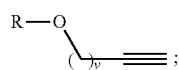

the halogenated alkyne compound can have a structure satisfying a formula

and the azide-containing compound has a structure satisfying a formula

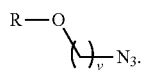

With reference to each of these formulas, each v independently is an integer selected from 1 to 10 and each R independently can be —$(CH_2)_w Ph(R')_z$, wherein each R' independently is trityl, nitro, silyl (e.g., —$Si(iPr)_3$), ester (e.g., —$CO_2Me$), carboxylic acid (e.g., —$CO_2H$), or aliphatic (e.g., t-butyl); each w independently is an integer selected from 0 to 10; each z independently is an integer selected from 1 to 5. In some embodiments, the metal catalyst is $Pd(MeCN)_2(Cl)_2$ or $Cu(MeCN)_4PF_6$.

In an exemplary embodiment, nanohoop compound embodiment 214 can be subjected to in-situ "active-template" reaction conditions by reacting with an alkyne (e.g., trityl-functionalized alkyne 218) and an azide (e.g., trityl-functionalized azide 220) in the presence metal-containing catalysts, such as copper-containing catalysts, to provide triazole-containing rotaxane 222, as illustrated in Scheme 5.

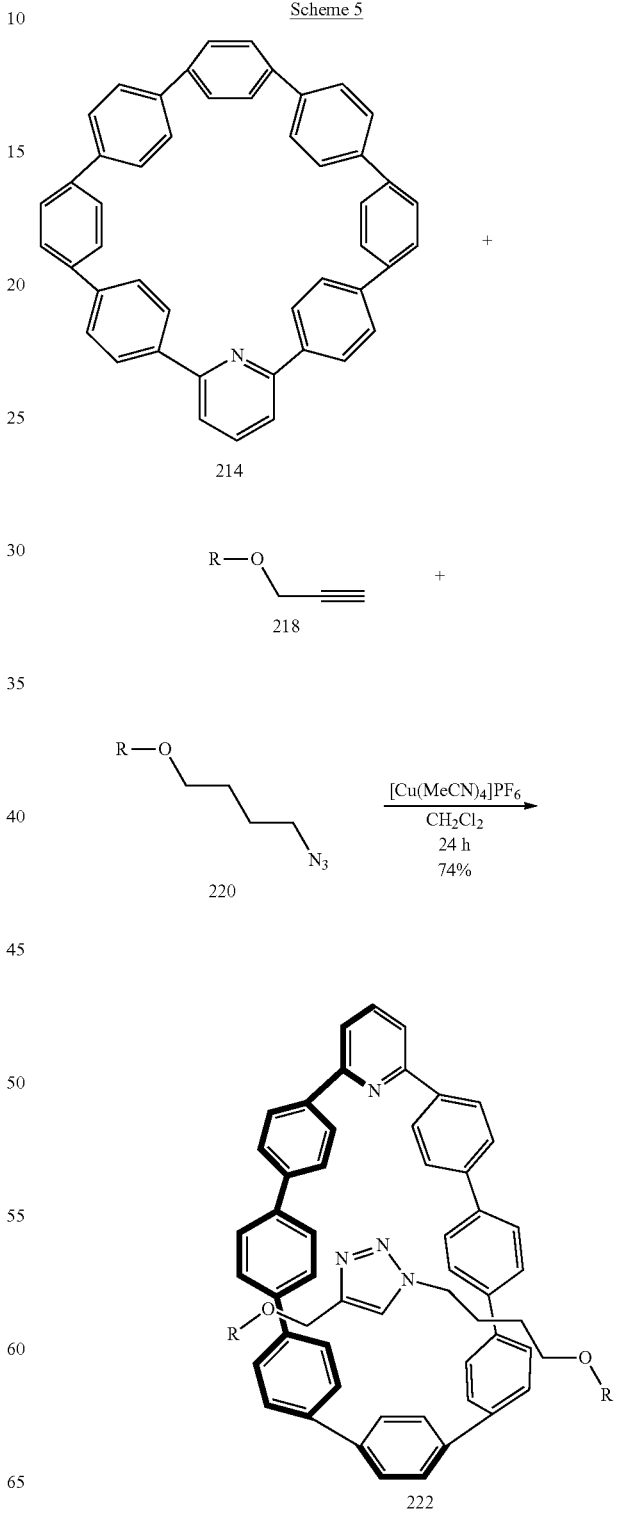

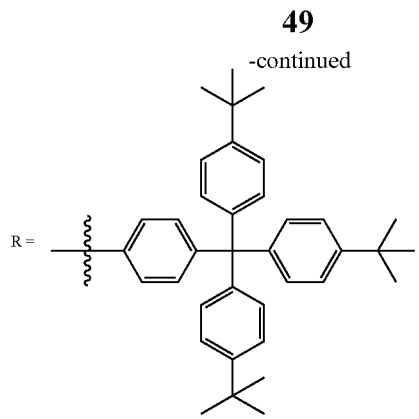

In another exemplary embodiment, nanohoop compound embodiment 214 can also be subjected to an in-situ Cadiot-Chodkiewicz reaction by reacting it with an alkyne (e.g., trityl-functionalized alkyne 218) and a bromide (e.g., trityl-functionalized bromide 224) to provide an alkyne-containing rotaxane (e.g., butadiyne-containing rotaxane 226), as illustrated in Scheme 6.

Scheme 6

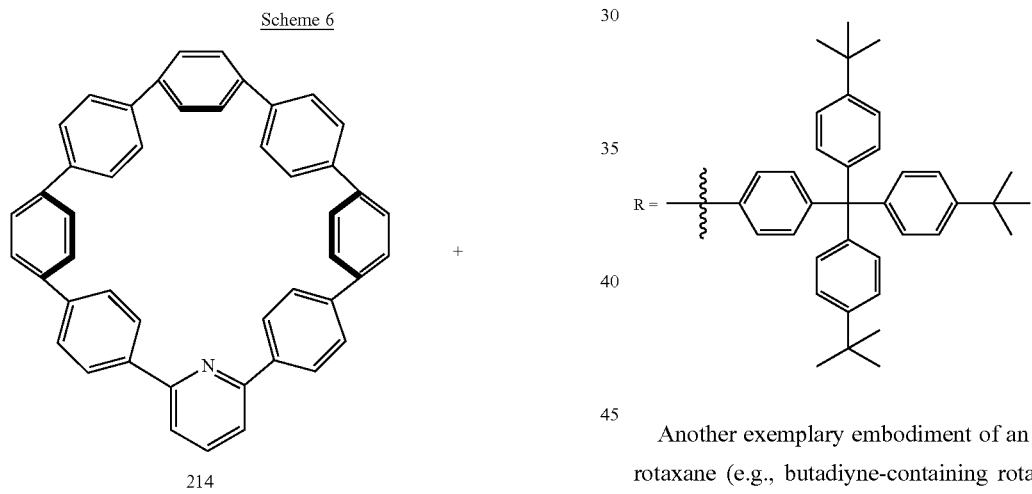

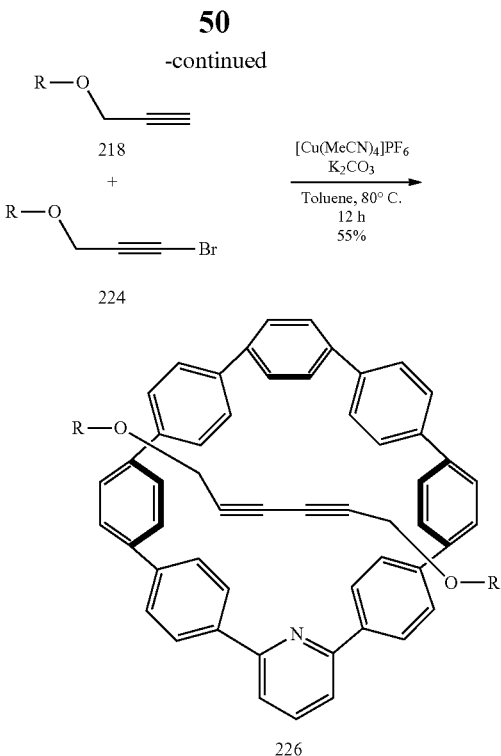

Another exemplary embodiment of an alkyne-containing rotaxane (e.g., butadiyne-containing rotaxane 316) is provided below in Scheme 7.

Scheme 7

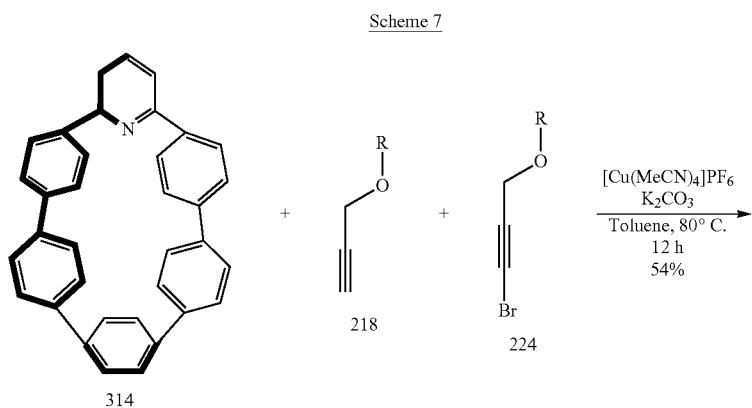

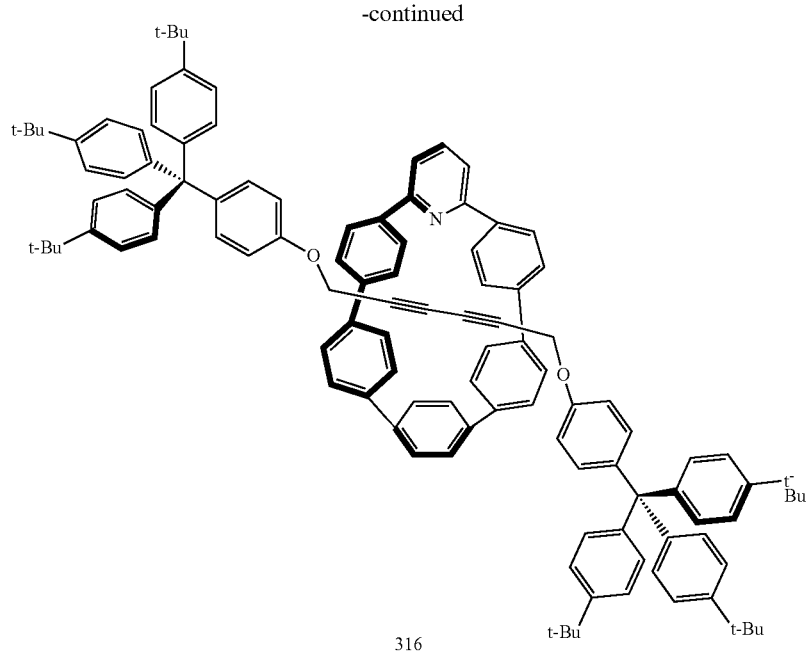
316
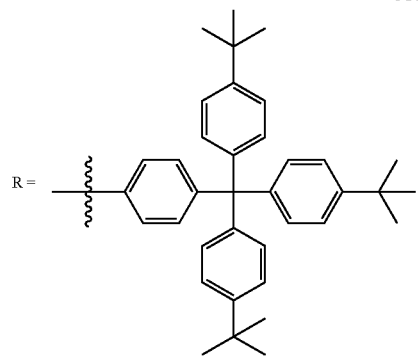
40
Additional exemplary nanohoop rotaxane compounds are illustrated below.
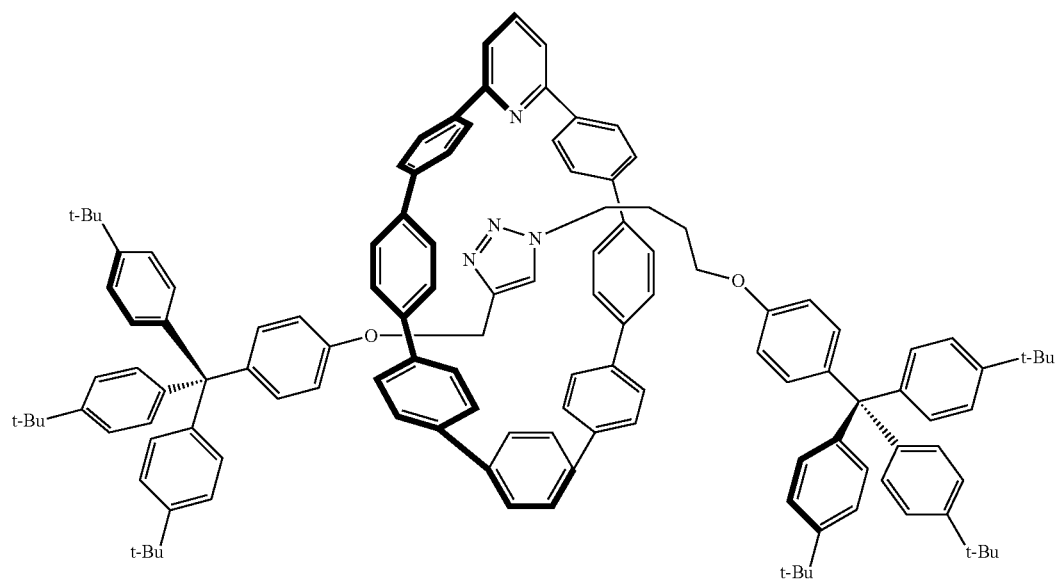

-continued
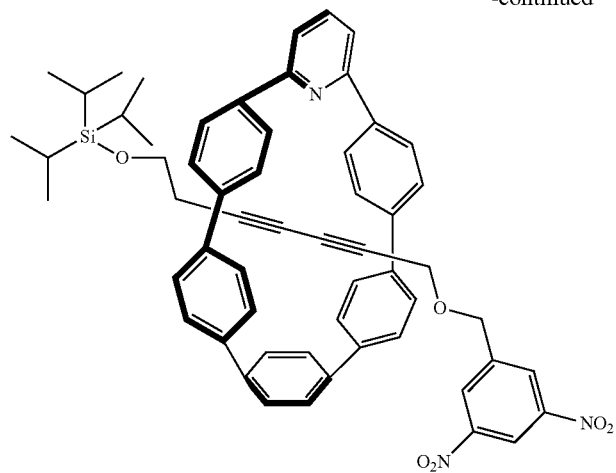
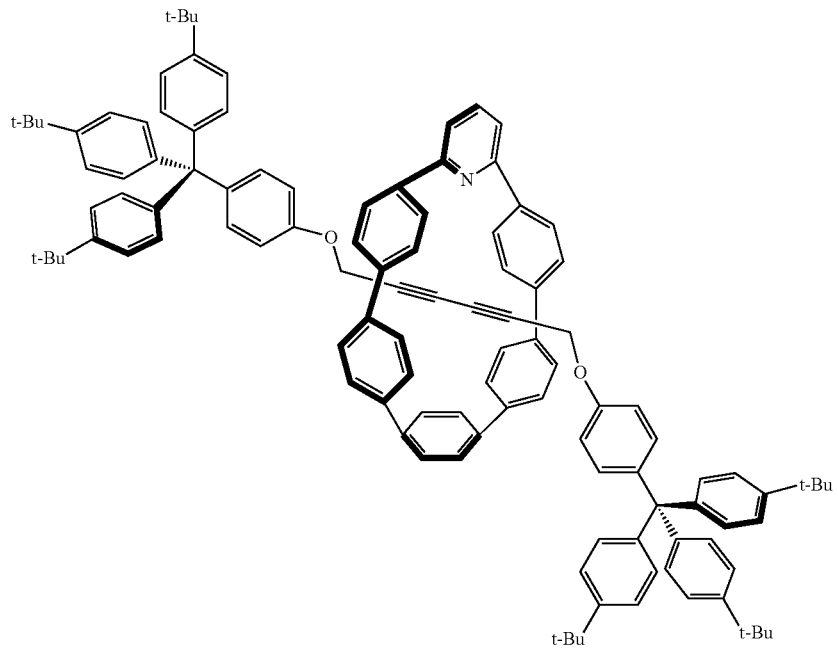
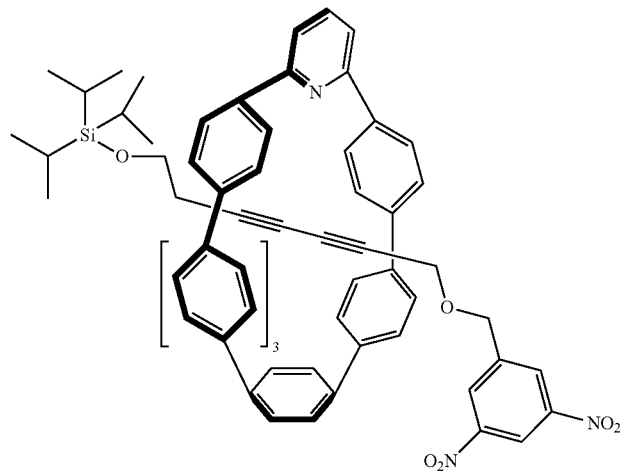

-continued
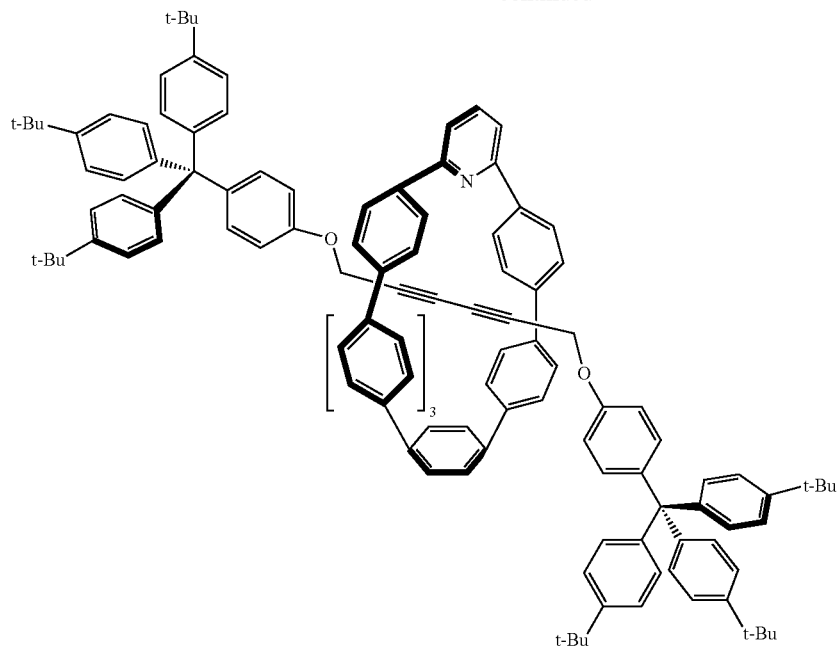
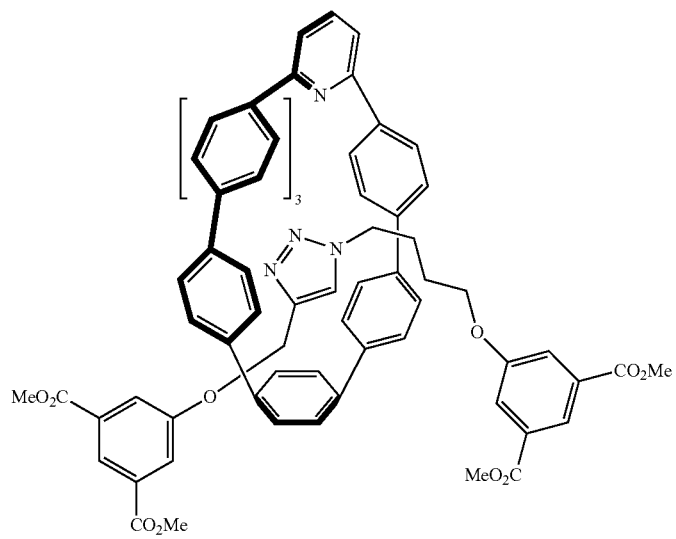
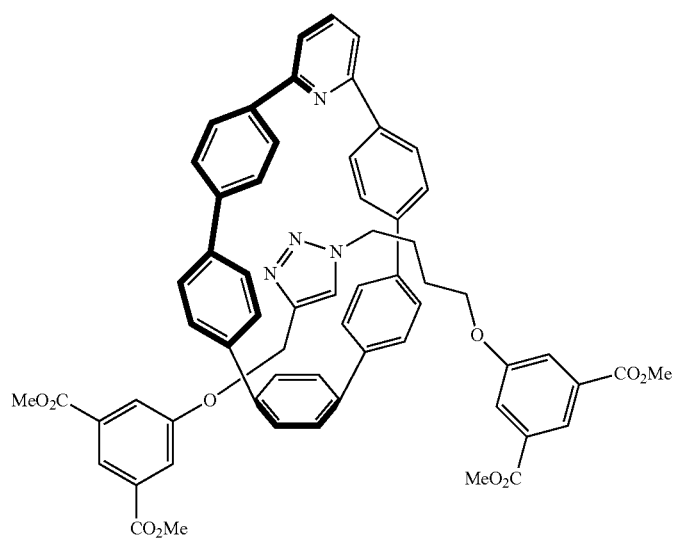

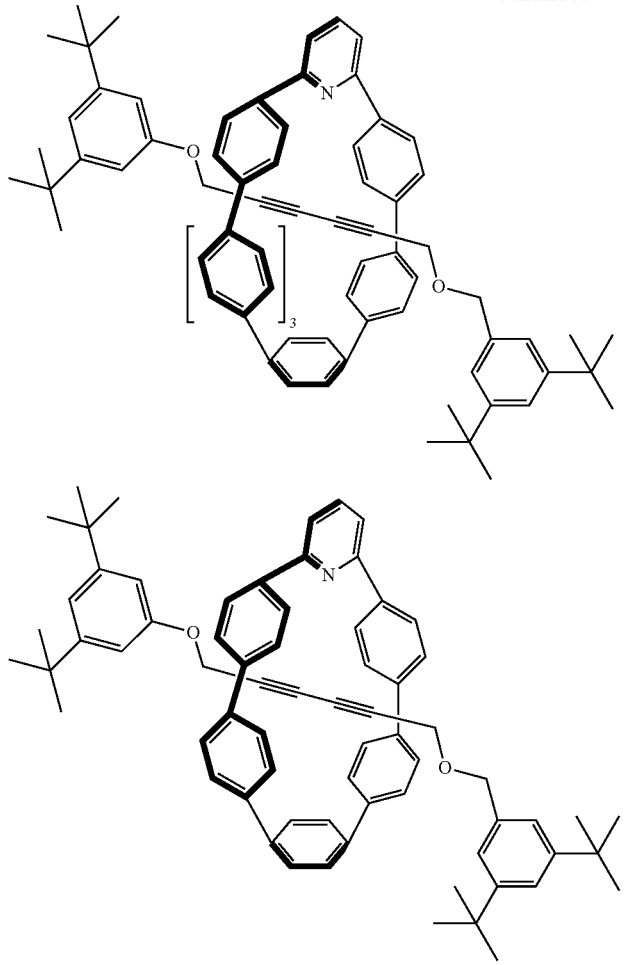

In some embodiments, nanohoop compound embodiments that further comprise a compound constrained within its cavity, such as in the above illustrated nanohoop-containing rotaxane embodiments, can coordinate metals in a reversible manner, which can result in fluorescence emission changes. For example, in some embodiments, nanohoop-containing rotaxane compounds can bind one or more metals, which can reduce the fluorescence exhibited by the nanohoop-containing rotaxane compound, and upon demetalation (that is, when the metal is released from coordination inside the cavity, the fluorescence returns. As such, these compounds can be useful as sensor compounds for determining the presence of metals in a sample. In yet additional embodiments, the compound constrained within the cavity can be used to control fluorescence of the nanohoop-containing rotaxane. For example, in some embodiments, the molecule constrained within the cavity of the nanohoop-containing rotaxane quenches fluorescence of the nanohoop-containing rotaxane. Then, when the compound is modified so as to be released from the cavity, fluorescence returns. In some embodiments, modifying the molecule constrained within the cavity can comprise chemically modifying the molecule, such as by cleaving one or more functional groups (e.g., silyl groups, boronate groups, amide groups, ester groups, and the like) from the molecule. In yet additional embodiments, the conformation of the molecule constrained within the cavity can be modified. In yet additional embodiments, the cavity itself can be modified to as to trigger release of the constrained molecule. Stimuli that can give rise to chemical and/or conformational changes that trigger release of the molecule from the cavity can include pH changes, electrochemical changes, reagents that cleave chemical bonds within the molecule, and the like. In some embodiments, cleaving one or more functional groups from the molecule can facilitate its release from the cavity.

In additional embodiments, different techniques can be used to evaluate structural features of rotaxanes (e.g., triazole-containing nanohoop rotaxane 222, butadiyne-containing nanohoop rotaxane 226, butadiyne-containing nanohoop rotaxane 316) and can be compared with those of the parent nanohoop compound (e.g., nanohoop compound embodiment 214, and/or compound 314) disclosed herein. Exemplary techniques used for the analysis of nanohoop-containing rotaxane compound embodiments are provided below.

In exemplary embodiments, the structure of a nanohoop rotaxane embodiment can be evaluated with mass spectroscopy (MALDI-TOF) and NMR spectroscopy. Additionally, in some embodiments, variable-temperature nuclear magnetic resonance spectroscopy (VT-NMR) can also be used to evaluate the structural features of the rotaxanes in relation to the corresponding parent nanohoop compound. Further, in yet additional embodiments, different techniques, such as mass spectroscopy (MALDI-TOF), NMR spectroscopy, time-dependent density functional theorem (TD-DFT), and the like, can be used to confirm the structure of nanohoop-containing rotaxane compound embodiments. Still further, in some embodiments, as described above, structural features of rotaxanes can also be characterized using solid-state, X-ray crystallography, UV-Vis absorption spectroscopy, and other techniques disclosed herein. Solid-state, single-crystal X-ray crystallography also can be used to determine the size of a cavity of a nanohoop compound embodiment.

In some embodiments, the discrete ring system connected to the para-linked aryl rings in the nanohoop structures disclosed herein (e.g., such as is illustrated in nanohoop compound embodiment 214) facilitates performing reactions (e.g., metalation reactions, click-chemistry reactions, and the like) within the cavity of the nanohoop, despite the highly-congested nature of the meta-linked discrete ring system. This results in a unique electronic environment within the cavity of the nanohoop. In an exemplary embodiment, meta-linked discrete ring systems of the nanohoop compound comprising one or more heteroaryl rings and/or aryl rings comprising a coordinating functional group (or combinations thereof), can be used in performing various reactions as described below.

In some embodiments, the nanohoop compound can facilitate polymerization reactions by anchoring a monomer within the cavity of the nanohoop structure. In one example, the polymerization reactions can be accomplished by binding the monomer to the coordinating functional group of the discrete ring system within the cavity of the nanohoop structure. The monomer, which is anchored to the nanohoop compound, can be subjected to a polymerization reaction. A final dissociation step may optionally be performed to separate the polymer from the nanohoop compound. In some other embodiments, a metalated-nanohoop compound can be used to catalyzing polymerization reactions, such as a metal-mediated polymerization reactions, within the cavity of the nanohoop structure. Exemplary metal-mediated polymerization reactions can include, but are not limited to, olefin polymerization, siloxane polymerization, phosphazene polymerization, and the like.

In some additional embodiments, the nanohoop compound disclosed herein can be used for binding and/or coordinating one or more charged guest species to one or more coordinating functional groups and/or metalated-heteroatoms of the discrete ring system within the cavity of the nanohoop compound, thereby forming a nanohoop-charged species complex for use with molecular recognition. In such embodiments, the nanohoop compound can act as a host species. In some embodiments, the host-guest interaction between the nanohoop compound and the charged species can involve non-covalent interaction, such as hydrogen bonds, ionic bonds, van der Waals forces, and hydrophobic interactions. In particular embodiments, a cation-containing discrete ring system can act as a host species to an anionic charged guest species. In another particular embodiment, an anion-containing discrete ring system can act as a host species to a cationic charged guest species. Exemplary applications of the molecular recognition using the nanohoop host-charged guest complexes can include, but are not limited to, chemical sensors, antigen-antibody, drug delivery applications, diseased cell-binding, fluorescence labelling, and the like. In some embodiments, the nanohoop can be a metalated-nanohoop compound that can be used to bind one or more charged guest species to the metal ion within the cavity of the nanohoop compound, thereby forming a metalated nanohoop-charged species complex for use with molecular recognition.

In yet some additional embodiments, the nanohoop compounds disclosed herein, and metalated versions thereof, can be used to catalyze carbon-carbon bond forming reactions, such as epoxidation, Michael reactions, aldol reactions, and the like. In additional embodiments, nanohoop embodiments comprising a discrete ring system can catalyze asymmetric organic reactions, such as asymmetric acylations, asymmetric phosphorylations, enantioselective oxidations, enantioselective reductions, enantioselective protonation, and the like. In yet additional embodiments, the discrete ring system of the nanohoop compounds can catalyze hydrolytic reactions. In the catalytic methods described above, the nanohoop compounds can be combined with a suitable starting material for the desired transformation (e.g., for an aldol reaction, the starting material would be an aldehyde or the corresponding carbon-containing alcohol compound reacted with the aldehyde) by coordinating (and/or covalently bonding) a suitable functional group of the starting material within the cavity of the nanohoop using functional groups present on the nanohoop and/or metals coordinated thereto.

IV. OVERVIEW OF SEVERAL EMBODIMENTS

Disclosed herein are embodiments of a nanohoop compound. In some embodiments, the nanohoop compound has a structure satisfying Formula 1 as disclosed herein and wherein each RS ring independently has a structure satisfying Formula II as disclosed herein and wherein at least one X is N, P, or C-CFG, wherein CFG is a coordinating functional group; each other X independently is C or $C(R^1)$ where $R^1$ is selected from an electron-accepting group or an electron-donating group; and r and t independently are 0 or 1; each A and A' ring independently is an aromatic ring; each R independently is selected from hydrogen, an electron-donating group, an electron-accepting group, or any combinations thereof; m is an integer selected from 1 to 4; m' is an integer selected from 0 to 4; each s and s' independently is an integer selected from 0 to 4; each n and n' independently is an integer selected from 0 to 24; and p is an integer selected from 1 to 20.

In any or all of the above embodiments, each RS ring independently has a structure satisfying Formula IIA, IIB, or IIC as disclosed herein.

In any or all of the above embodiments, ring B is a heteroaryl ring and r and t are 0.

In any or all of the above embodiments, ring B and ring C bind together to provide a hetero-biaryl ring group and r is 0.

In any or all of the above embodiments, ring B, ring C, and ring D bind together to provide a three-ring heteroaryl ring system and r is 0.

In any or all of the above embodiments, ring B, ring C, ring D, and ring E bind together to provide a four-ring fused heteroaryl ring system, and r is 0.

In any or all of the above embodiments, ring B, ring C, and ring F bind together to provide a heterotriaryl ring system.

In any or all of the above embodiments, the nanohoop compound has a structure satisfying any one or more of Formulas IIIA-IIIF as disclosed herein. In some embodiments, for Formulas IIIA, IIIB, IIIC, IIIE, and IIIF, each X is N and for Formula IIID, at least one X is $C(R^1)$ where $R^1$ is selected from an electron-accepting group or an electron-donating group and each other X independently is C or $C(R^1)$ where $R^1$ is selected from an electron-accepting group or an electron-donating group.

In any or all of the above embodiments, the nanohoop compound has a structure satisfying any one or more of Formulas IVA-IVC as disclosed herein and wherein n is 1, or 3-5.

In any or all of the above embodiments, the nanohoop compound is

In any or all of the above embodiments, the nanohoop compound further comprises an interlocked molecule that is confined by a cavity defined by the nanohoop compound.

In any or all of the above embodiments, the interlocked molecule is a triazole-containing compound or an alkyne-containing compound.

In any or all of the above embodiments, the nanohoop compound is selected from the nanohoop rotaxane compounds disclosed herein.

In any or all of the above embodiments, each RS group is connected to the A or A' ring in a manner such that atoms of the RS group are oriented substantially perpendicular to the atoms of the A ring or A' ring.

In any or all of the above embodiments, the nanohoop compound is a nanohoop compound comprising a major axis between a meta-linked RS group and a distal para-linked aryl ring that is substantially larger than a minor axis between two distal para-linked aryl rings.

Also disclosed herein are embodiments of a method for making a nanohoop rotaxane compound. In some embodiments, the method comprises combining a metal catalyst with (i) a nanohoop compound as described herein; (ii) an alkyne-containing compound; and (iii) a halogenated alkyne compound or an azide containing compound to provide a nanohoop rotaxane compound comprising an interlocked alkyne-containing compound or an interlocked triazole-containing compound constrained within a cavity of the nanohoop compound.

In any or all of the above embodiments, the alkyne containing compound has structure satisfying a formula

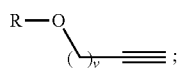

the halogenated alkyne compound has a structure satisfying a formula

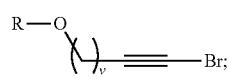

and the azide-containing compound has a structure satisfying a formula

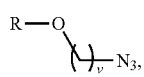

wherein each R independently is $-(CH_2)_w Ph(R')_z$, wherein each R' independently is trityl, nitro, silyl, ester, carboxylic acid, or aliphatic; each w independently is an integer selected from 0 to 10; each z independently is an integer selected from 1 to 5; and each v independently is an integer selected from 1 to 10.

In any or all of the above embodiments, the metal catalyst is $Pd(MeCN)_2(Cl)_2$ or $Cu(MeCN)_4 PF_6$.

Also disclosed herein are embodiments of a method of using the nanohoop rotaxane compound embodiments disclosed herein. In some embodiments, the method comprises using the nanohoop rotaxane compound according to any or all of the above embodiments as a sensor by exposing an analyte to the nanohoop rotaxane compound and determining the presence of fluorescence emitted by the nanohoop compound after the interlocked alkyne-containing compound or the interlocked triazole-containing compound is released from the cavity of the nanohoop compound.

Also disclosed herein are embodiments of a method for making a nanohoop compound. In some embodiments, the method comprises: cross-coupling a compound having a structure satisfying a Formula A with a RS precursor having a structure satisfying a Formula B to provide a substituted nanohoop precursor having a structure satisfying a compound C; and deprotecting the substituted nanohoop precursor to provide the substituted nanohoop compound; wherein Formula A, B, and C are as described herein and wherein each PG independently is a silyl protecting group, each LG independently is a leaving group selected from chloro, fluoro, bromo, or iodo, each s and s' can independently be an integer selected from 0 to 4; and each n and n' can independently be an integer selected from 0 to 24.

In any or all of the above embodiments, the cross-coupling is performed using a transition metal-based catalyst and a base and wherein the substituted nanohoop compound is exposed to a metal complex to provide a metalated-nanohoop compound.

Also disclosed herein are embodiments of a molecular machine, a chemical device, or a sensor comprising a nanohoop compound disclosed herein. In some embodiments, the molecular machine is selected from a molecular shuttle, a molecular motor, a molecular propeller, a molecular switch, or any combinations thereof. In some embodiments, the chemical device is configured to perform a polymerization reaction, asymmetric organic reactions, hydrolytic reactions, or any combinations thereof.

V. EXAMPLES

General Information:

$^1$H NMR spectra were recorded at 500 MHz on Varian VNMR spectrometer, 500 MHz on a Bruker, or 600 MHz on Bruker. All $^1$H NMR spectra are referenced to residual $CHCl_3$ (δ 7.26 ppm). All $^{13}$C NMR spectra are references to a residual $CHCl_3$ (δ 77.16 ppm). All reagents were obtained commercially. All glassware was flame-dried and cooled under an inert atmosphere of nitrogen unless otherwise noted. Moisture sensitive reactions were carried out under an inert atmosphere of nitrogen using standard syringe/septa technique. Silica column chromatography was conducted with Zeochem Zeoprep n60 Eco 40-63 μM silica gel while alumina chromatography utilized Sorbent Technologies 50-200 um Basic Activity II-II Alumina.

H2SnCl4, where noted, was prepared in the following manner: To a solution of $SnCl_2 \cdot 2H_2O$ (180.0 mg, 0.796 mmol, 1.00 equiv) in 10 mL THF was added conc. HCl (133.0 μL, 1.59 mmol, 2.0 equiv.). The resulting solution was then stirred for 15 minutes and used as needed.

Compounds 210 and 300 are prepared as described herein and compounds 218 and 220 can be made using procedures known to those of ordinary skill in the art with the benefit of the present disclosure. Compound 224 was prepared by treating compound 218 with NBS and AgNO3. Additional precursors for the molecules that can be constrained in the nanohoop cavity also are illustrated below.

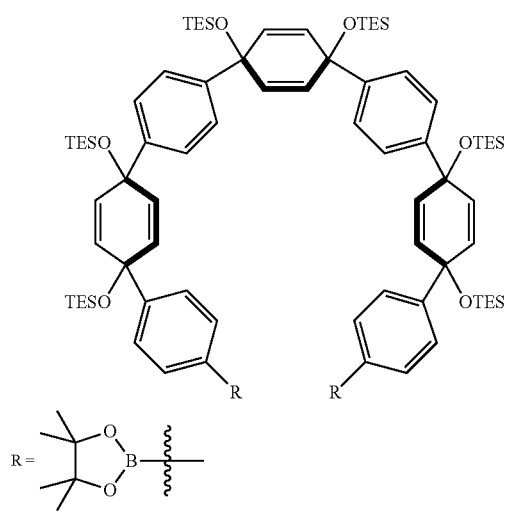
210
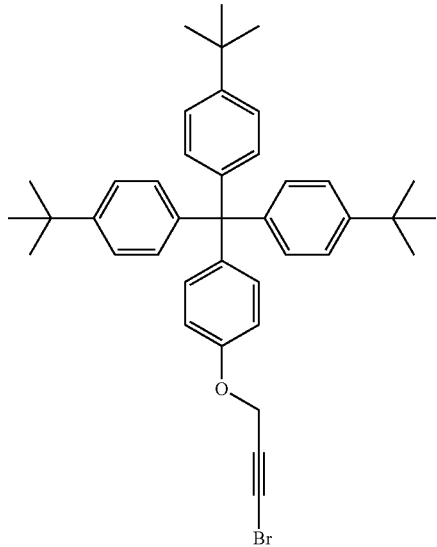
224
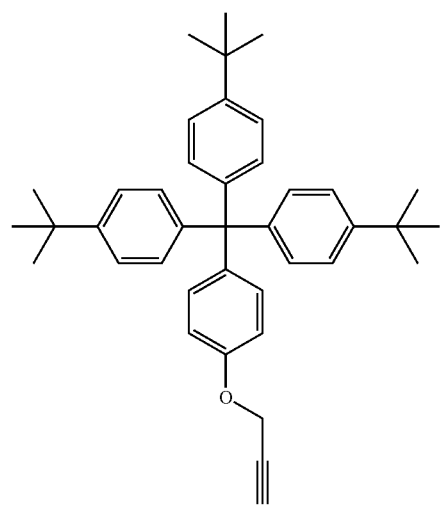
218
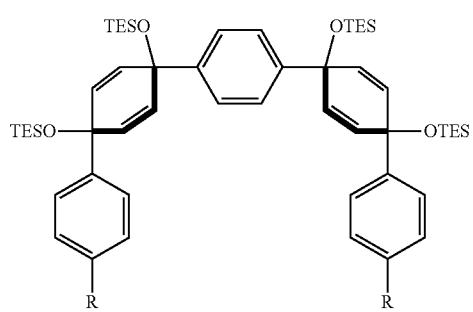
300
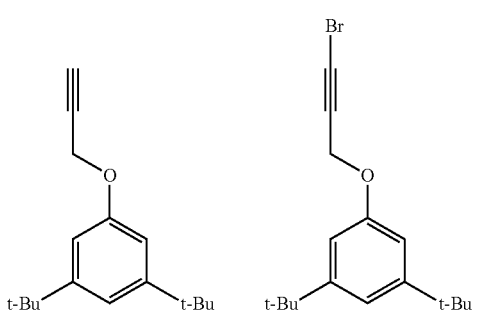
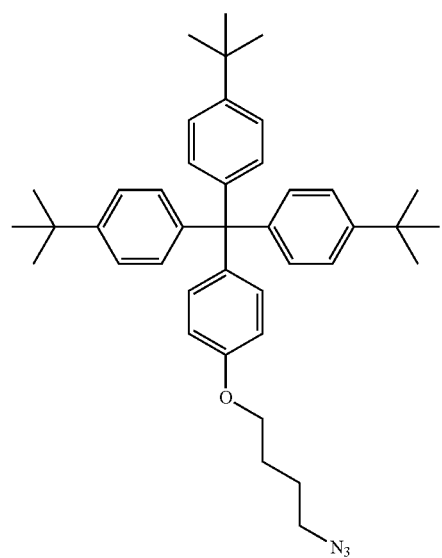
220
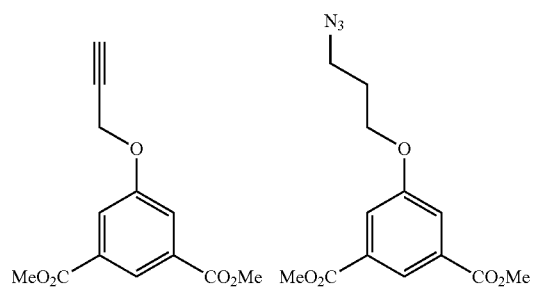

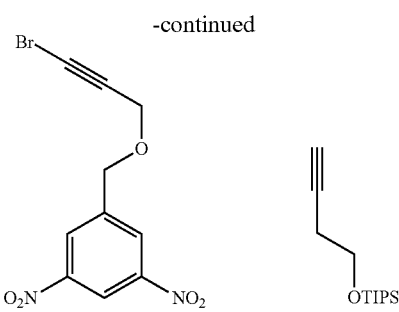

Computational Data

All calculations were carried out with the Gaussian 09 package using B3LYP-6-31 G level of theory. Geometries were first optimized in the gas phase. Once optimized a single point calculation was carried out using the CPCM solvation model with acetonitrile as the solvent continuum to account for charged species. All excited state calculations (TD-DFT) were performed on fully optimized structures. The fully optimized structures were confirmed to be true minima by vibrational analysis. Structures were minimized with no symmetry restrictions.

Example 1

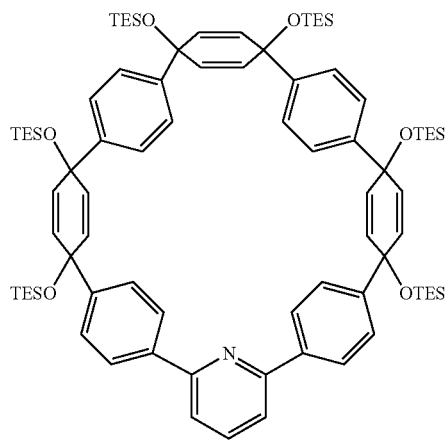

Figure 2:
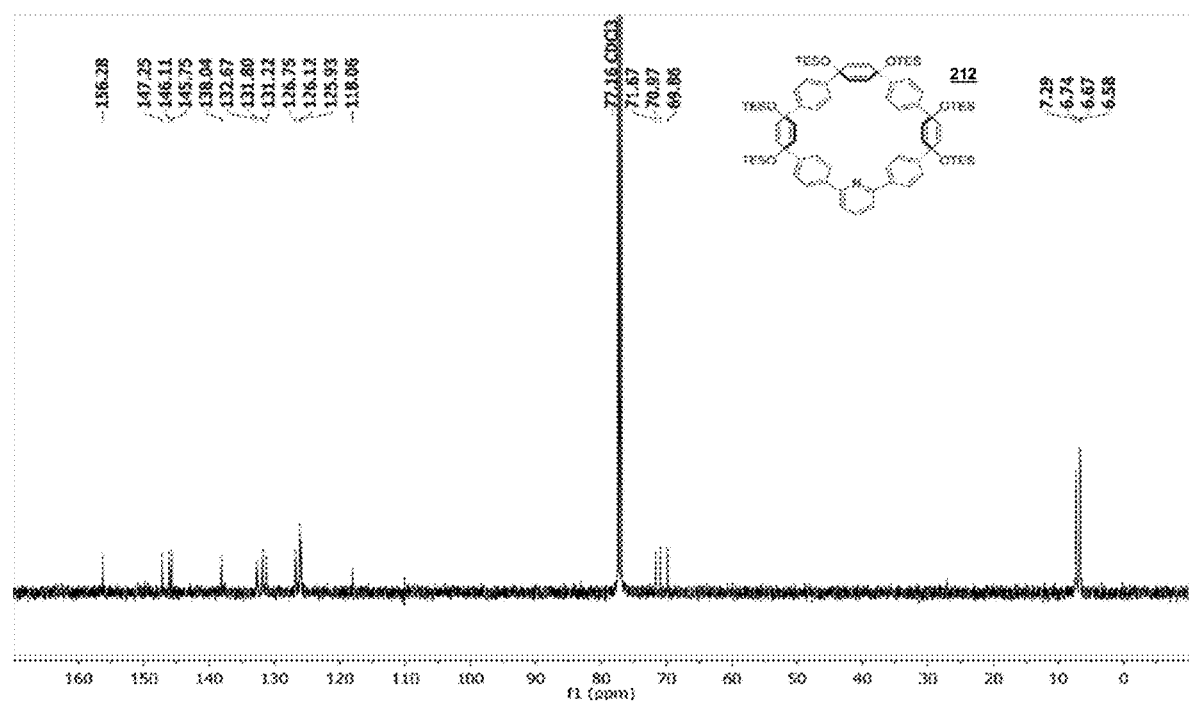
FIG. 2 is a $^{13}$C-NMR spectrum of nanohoop precursor embodiment 212.

To a flame-dried 2 L round bottom flask equipped with a stir bar, compound 210 (2.10 g, 1.33 mmol, 1.00 equiv.), 2,6-dibromopyridine (0.330 g, 1.40 mmol, 1.05 equiv.), and Pd SPhos GII (0.0958 g, 0.133 mmol, 0.10 equiv.) were added. The flask was evacuated and back-filled with $N_2$ five times, followed by addition of 1,4-dioxane (700 mL). This solution was then vigorously purged with $N_2$ for 30 minutes at which point it was then placed into an 80° C. oil bath for 30 minutes. At this point, an aqueous solution of 2M $K_3PO_4$ (70.0 mL, 35.0 mmol, 26.3 equiv.) was added, quickly turning the solution to a bright yellow. The reaction was monitored until all starting material was consumed (typically 1 hour), at which point the solution was allowed to cool to room temperature. After removal of the solvent via rotary evaporation, the resulting yellow/brown oil was extracted with DCM (3×75 mL), followed by washing of the combined organic phases with $H_2O$ (3×100 mL), brine (1×100 mL), and finally placed over sodium sulfate. Removal of the organic phase gave a yellow oil, which, on addition of acetone (5 mL), caused the precipitation of a white solid which was then collected via filtration to give compound 212 as a white solid (0.810 g, 45%). $^1H$ NMR (500 MHz, Chloroform-d) δ 8.05 (d, J=8.4 Hz, 4H), 7.78 (t, J=7.8 Hz, 1H), 7.67 (d, J=7.8 Hz, 2H), 7.52-7.41 (m, 12H), 6.14 (s, 4H), 6.05 (d, J=10.0 Hz, 4H), 5.90 (d, J=10.1 Hz, 4H), 0.98 (m, 18H), 0.91 (m, 36H), 0.70 (m, 12H), 0.59-0.50 (m, 24H)—see FIG. 1; $^{13}0$ NMR (126 MHz, Chloroform-d) δ 156.28, 147.25, 146.11, 145.75, 138.04, 132.67, 131.80, 131.22, 126.75, 126.12, 125.93, 118.06, 71.67, 70.97, 69.86, 7.29, 6.74, 6.67, 6.58—see FIG. 2; MS (MALDI-TOF) (m/z): [M]+calculated for $C_{83}H_{121}NO_6Si_6$, 1395.780; found, 1395.820.

Example 2

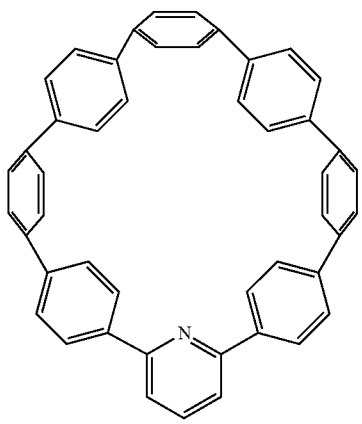

Figure 3:
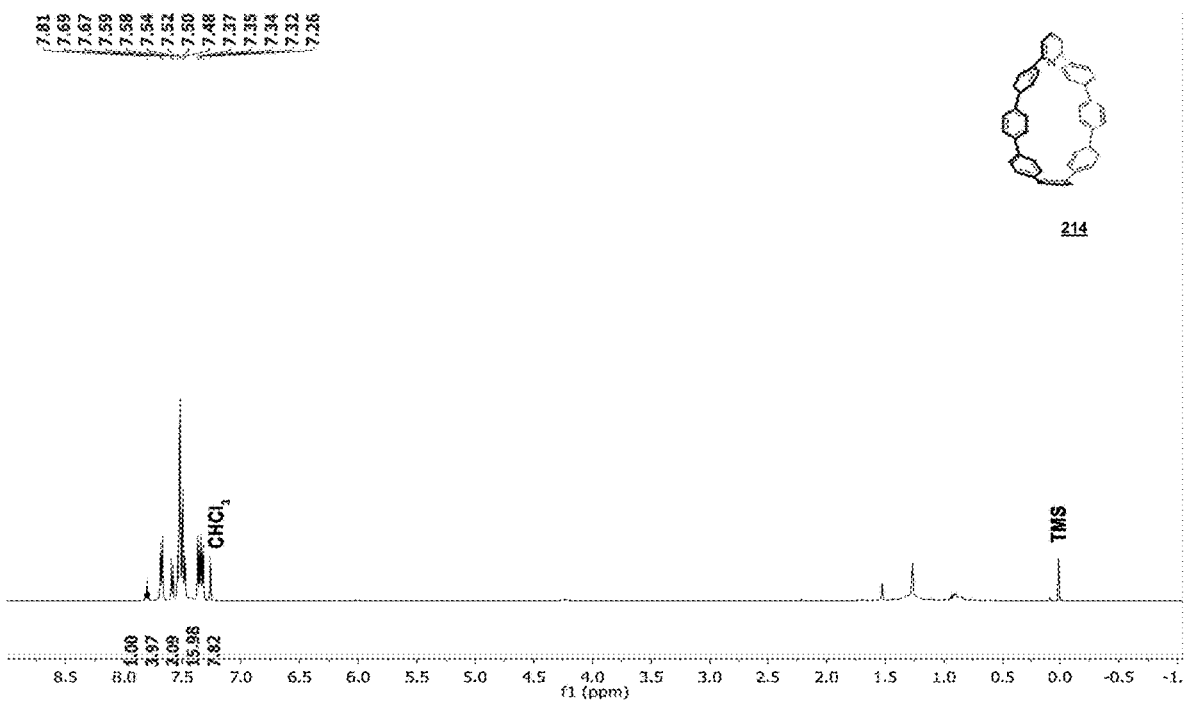
FIG. 3 is a $^1$H-NMR spectrum of nanohoop compound embodiment 214, which comprises an aromatic ring comprising meta-substitution.
Figure 4:
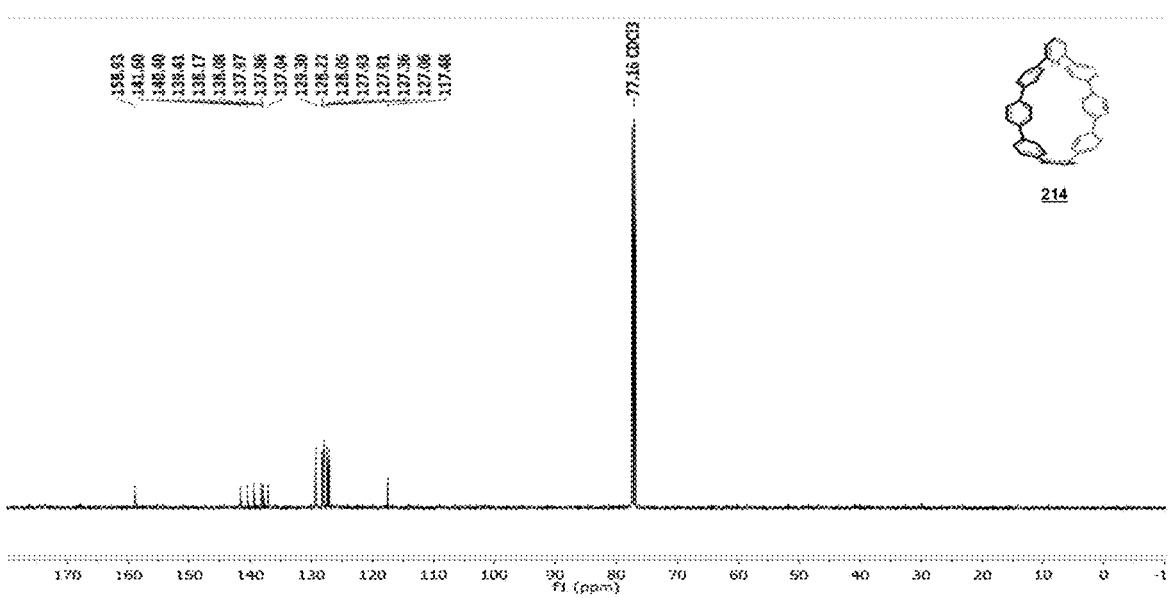
FIG. 4 is a $^{13}$C-NMR spectrum of nanohoop compound embodiment 214.
Figure 25:
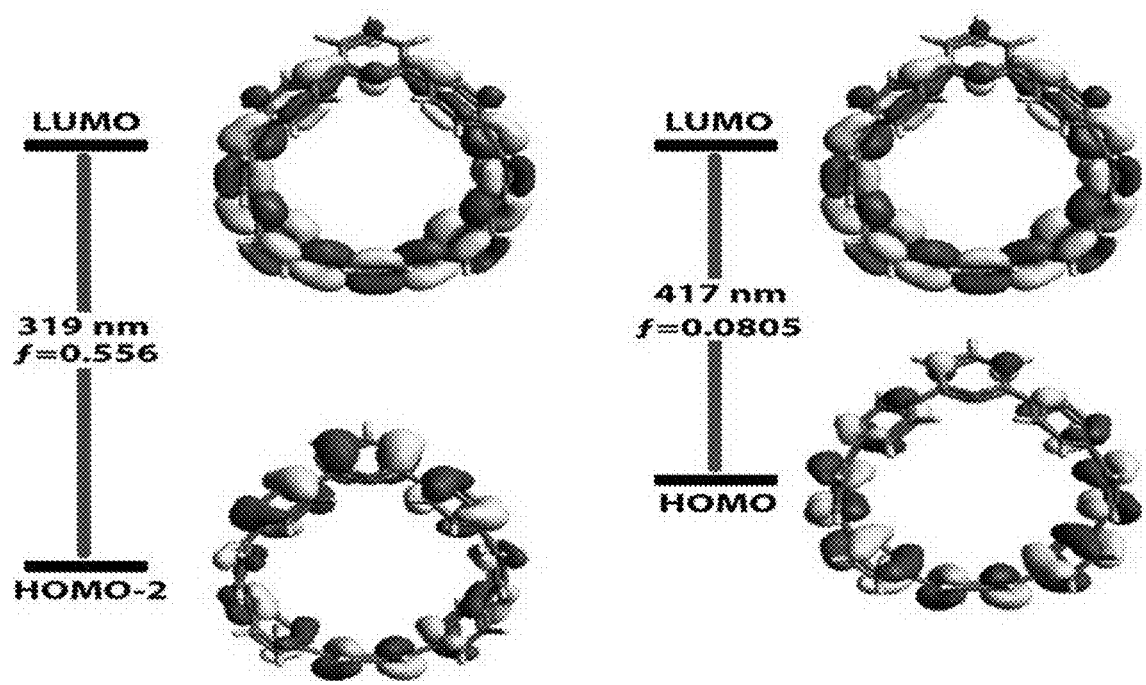
FIG. 25 is a time-dependent density functional theorem (TD-DFT) minimized structure of nanohoop compound embodiment 214 showing frontier molecular orbitals.

To a flame-dried 100 mL round bottom flask equipped with a stir bar, compound 212 (0.360 g, 0.257 mmol, 1.00 equiv.) was added, followed by THF (20 mL). To this solution, tetrabutylammonium fluoride (TBAF) (1 M in THF, 2.57 mmol, 2.58 mL, 10.0 equiv.) was added, resulting in a tan-colored suspension. After stirring for 45 minutes, THF was removed via rotary evaporation, followed by addition of $H_2O$ (20 mL) resulting in a white precipitate. The white solid was collected via filtration, washed with $H_2O$ (50 mL), DCM (5 mL) and was then transferred to a flame-dried 100 mL round-bottomed flask with stir bar. After addition of THF (20 mL), $H_2SnCl_4$ was added dropwise, turning the colorless solution to a bright orange over 20 minutes. This was then allowed to stir for 45 min, at which point aqueous 1M NaOH (5 mL) was added, quickly turning the solution from bright orange to bright yellow. The THF was removed via rotary evaporation, followed extraction of the resulting yellow/orange aqueous suspension with DCM (3×50 mL). The combined organic phases were washed with $H_2O$ (3×50 mL), brine (1×50 mL) and then dried over sodium sulfate. After removal of DCM under reduced pressure, the resulting yellow solid was run through a short alumina plug using DCM eluent, providing nanohoop compound embodiment 214 as a yellow solid (0.111 mg, 53%). $^1H$ NMR (500 MHz, Chloroform-d) δ 7.81 (t, J=7.8 Hz, 1H), 7.68 (d, J=8.2 Hz, 4H), 7.58 (d, J=7.8 Hz, 2H), 7.56-7.46 (m, 16H), 7.36 (d, J=8.4 Hz, 4H), 7.33 (d, J=8.5 Hz, 4H)—see FIG. 3; $^{13}0$ NMR (126 MHz, $CDCl_3$) δ 158.93, 141.60, 140.40, 139.41, 138.17, 138.08, 137.97, 137.86, 137.04, 129.30, 128.22, 128.05, 127.93, 127.91, 127.36, 127.06, 117.48—see FIG. 4; MS (MALDI-TOF) (m/z): [M+H]+calculated for $C_{47}H_{32}N$, 610.251; found, 610.210. A time-dependent density functional theorem (TD-DFT) minimized structure of nanohoop compound embodiment 214 showing frontier molecular orbitals is provided by FIG. 25.

Computational Data

TABLE 1

Major electronic transitions for Nanohoop Compound Embodiment 214 determined by TD-DFT method using B3LYP/6-31g

| Wavelength (nm) | Osc. Strength | Major contributions |
|---|---|---|
| 417.2977572 | 0.0805 | HOMO->LUMO (94%) |
| 367.7175806 | 0.2811 | HOMO->L + 1 (90%) |
| 344.7908358 | 1.112 | H − 1->LUMO (89%) |
| 339.9784376 | 0.0057 | H − 1->L + 1 (84%) |
| 328.8072152 | 0.2313 | HOMO->L + 2 (86%) |

TABLE 1-continued

Major electronic transitions for Nanohoop Compound Embodiment 214 determined by TD-DFT method using B3LYP/6-31g

| Wavelength (nm) | Osc. Strength | Major contributions |
|---|---|---|
| 319.5199769 | 0.556 | H − 2->LUMO (87%) |
| 306.9274332 | 0.0236 | H − 2->L + 1 (48%), H − 1->L + 2 (46%) |
| 304.3805677 | 0.1149 | HOMO->L + 3 (59%), HOMO->L + 4 (20%) |
| 297.3649365 | 0.0991 | HOMO->L + 3 (20%), HOMO->L + 4 (45%) |
| 295.9170763 | 0.0066 | H − 4->LUMO (11%), H − 1->L + 4 (10%), HOMO->L + 5 (22%), HOMO->L + 6 (37%) |
| 293.2018556 | 0.0483 | H − 2->L + 1 (34%), H − 1->L + 2 (41%) |
| 287.3709824 | 0.0171 | H − 5->LUMO (15%), H − 3->LUMO (40%), H − 3->L + 2 (10%) |

Example 3

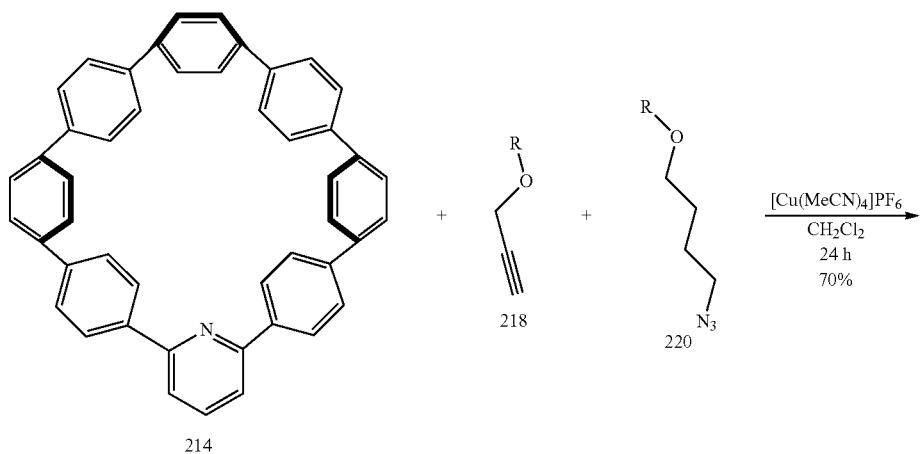

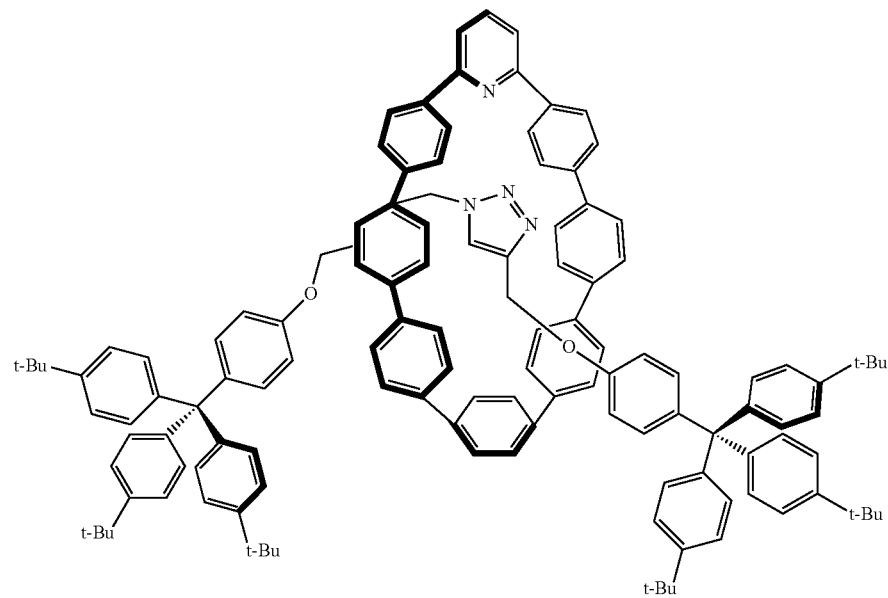

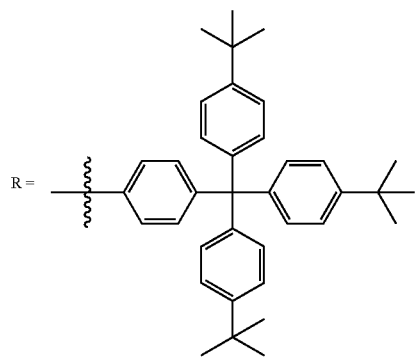

R =

Figures 6, 7:
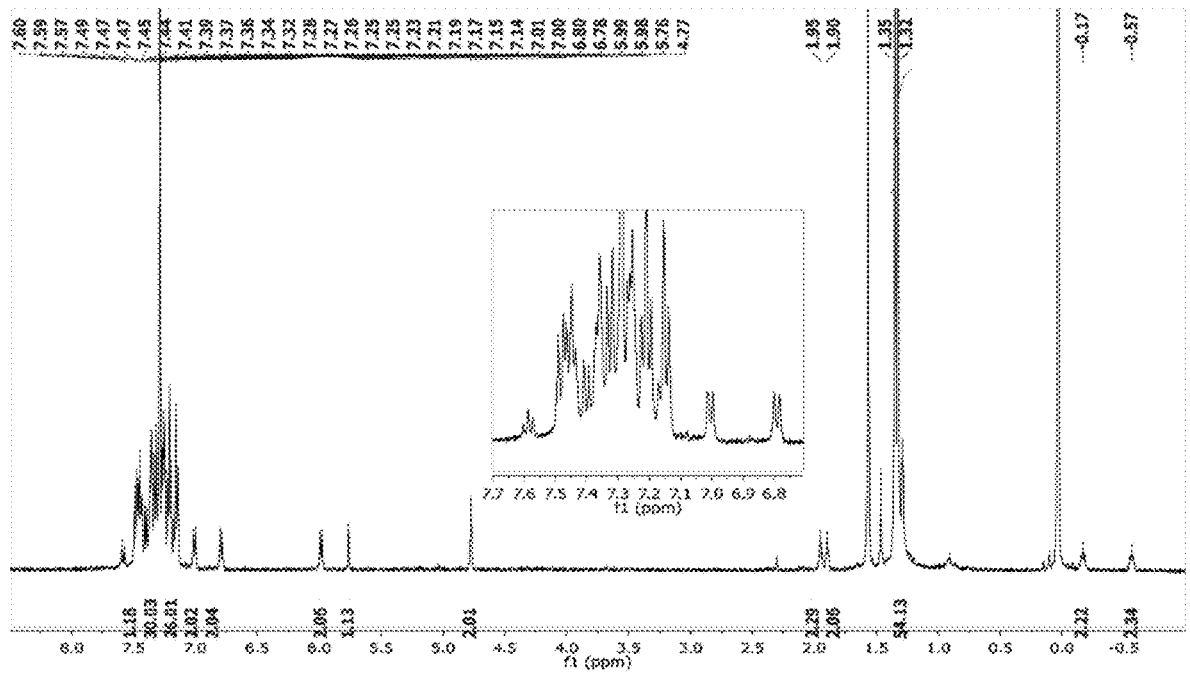
FIG. 6 is a $^1$H-NMR spectrum of triazole-containing rotaxane 222, which comprises a nanohoop compound embodiment and a triazole molecule constrained within a cavity of the nanohoop compound.
FIG. 7 is a $^{13}$C-NMR spectrum of triazole-containing rotaxane 222.

To a flame-dried 25 mL flask equipped with a stir bar, nanohoop compound embodiment 214 (11.7 mg, 0.0192 mmol, 1.00 equiv.), Cu(MeCN)$_4$PF$_6$ (6.4 mg, 0.0184 mmol, 0.96 equiv.), azide 220 (0.115 g, 0.192 mmol, 10.0 equiv.) and alkyne 218 (0.104 g, 0.192 mmol, 10.0 equiv.) were added. The flask was then evacuated and refilled with N$_2$ for about five times. A septum was then placed on the flask, followed by the addition of 5 mL DCM. The reaction was followed with TLC and allowed to stir until complete consumption of azide 220 or alkyne 218. At this point, the reaction was quenched with an NH$_3$-EDTA (2 mL) and then allowed to stir for 10 minutes. The layers were separated, followed by additional washing of the aqueous phase with DCM (2×20 mL). The combined organic phases were washed with H$_2$O (3×20 mL), and brine (1×20 mL), and dried over sodium sulfate to give a bright yellow solid, which after chromatography (50% diethyl ether/hexanes, SiO$_2$), yielded the desired triazole-containing rotaxane 222 as a yellow solid/oil (23.5 mg, 70%). $^1$H NMR (500 MHz, Chloroform-d) δ 7.56 (t, J=7.9 Hz, 1H), 7.50-7.28 (m, 30H), 7.24-7.08 (m, 26H), 6.97 (d, J=8.8 Hz, 2H), 6.76 (d, J=8.4 Hz, 2H), 5.73 (s, 1H), 4.74 (s, 2H), 1.92 (t, J=6.7 Hz, 2H), 1.86 (d, J=4.8 Hz, 2H), 1.32 (s, 27H), 1.29 (s, 27H), −0.17--0.21 (m, 2H), −0.51--0.65 (m, 2H)—see FIG. 6; $^{13}$C NMR (126 MHz, CDCl$_3$) δ 148.59, 148.50, 144.40, 144.24, 141.01, 140.55, 139.01, 136.89, 132.48, 131.88, 130.87, 130.84, 129.27, 128.17, 127.85, 127.53, 127.34, 127.17, 124.35, 124.26, 122.35, 117.49, 113.26, 63.27, 34.50, 34.46, 31.57, 31.54—see FIG. 7; MS (MALDI-TOF) (m/z): [M]+ calculated for C$_{128}$H$_{128}$N$_4$O$_2$, 1753.003; found, 1752.858.

Example 4

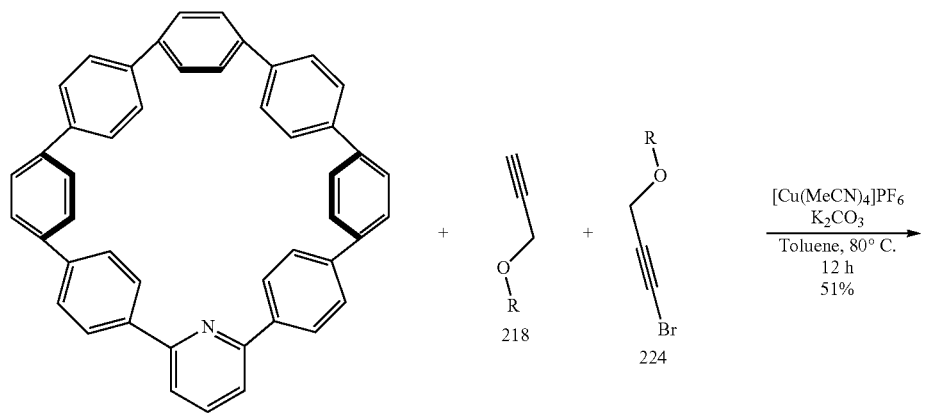

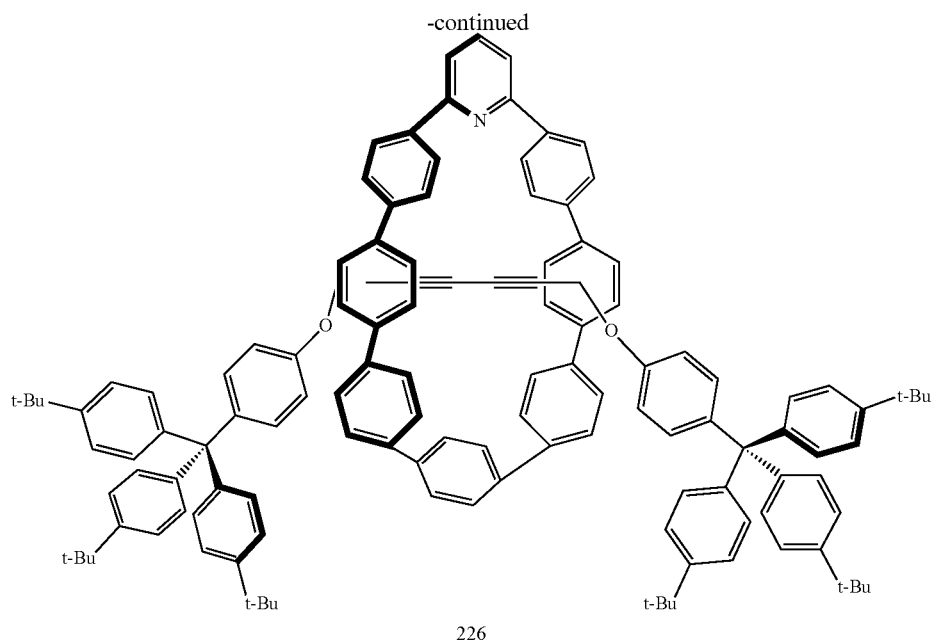

226

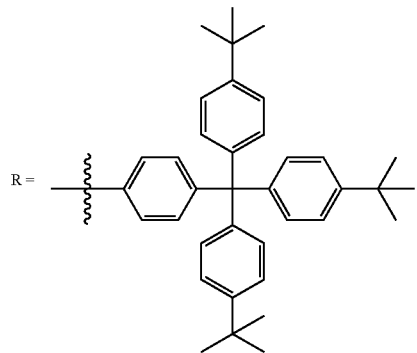

R =

Figure 11:
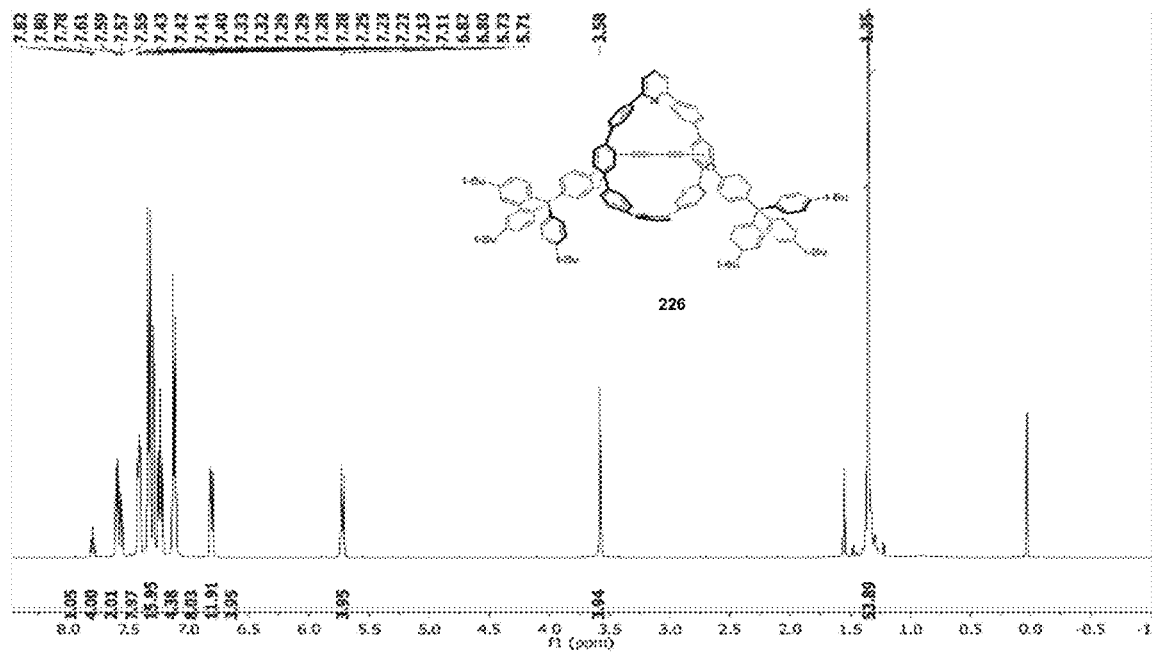
FIG. 11 is a $^1$H-NMR spectrum of butadiyne-containing rotaxane 226, which comprises a nanohoop compound embodiment and a di-alkyne molecule constrained within a cavity of the nanohoop compound.
Figure 12:
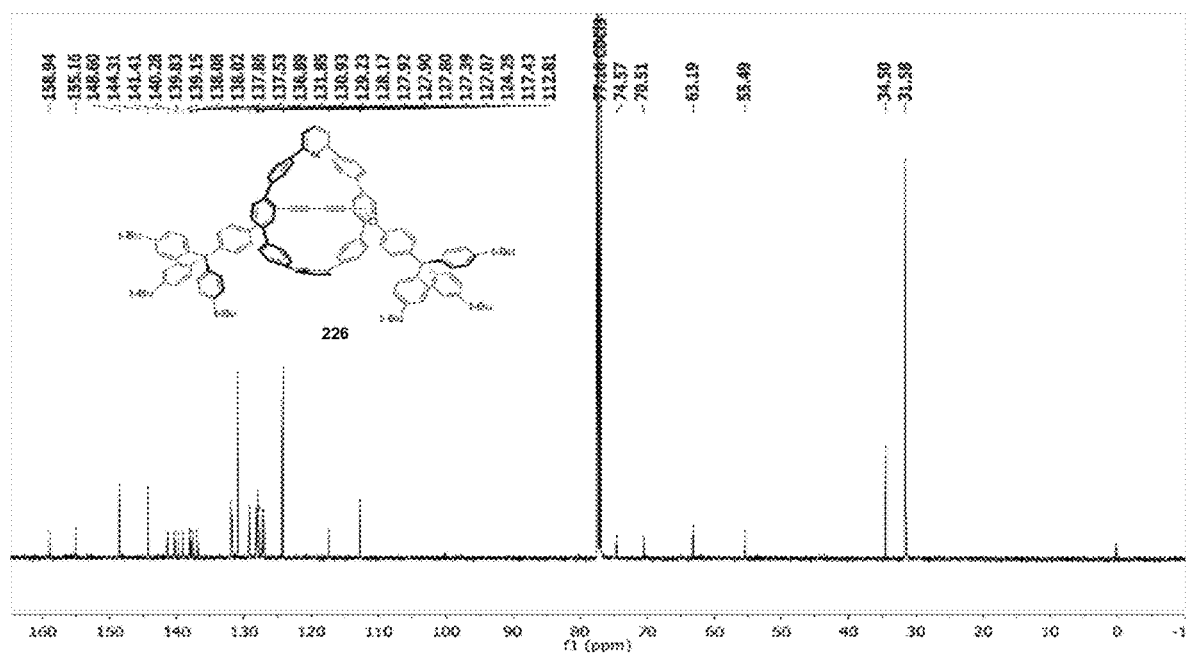
FIG. 12 is a $^{13}$C-NMR spectrum of butadiyne-containing rotaxane 226.

To a flame-dried 25 mL flask equipped with a stir bar, nanohoop compound embodiment 214 (17.8 mg, 0.0292 mmol, 1.00 equiv.), Cu(MeCN)$_4$PF$_6$ (10.4 mg, 0.0280 mmol, 0.96 equiv.), bromo alkyne 224 (0.0190 g, 0.0350 mmol, 1.2 equiv.), terminal alkyne 218 (0.0217 g, 0.0350 mmol, 1.2 equiv.), and potassium bicarbonate (20.1 mg, 0.146 mmol, 5.00 equiv.) were added. The flask was then evacuated and refilled with N$_2$ for about five times. A septum was then placed on the flask, followed by the addition of 5 mL toluene. The reaction was then heated to 80° C. and the reaction progress was followed with TLC. On completion, the reaction was quenched with an NH$_3$-EDTA (2 mL) solution and then allowed to stir for 10 minutes. The layers were separated, followed by additional washing of the aqueous phase with DCM (2×20 mL). The combined organic phases were washed with H$_2$O (3×20 mL), and brine (1×20 mL), and dried over sodium sulfate to give a bright yellow solid/oil, which after chromatography (50% diethyl ether/hexanes), yielded the desired rotaxane 226 as a yellow solid (25.2 mg, 51%). $^1$H NMR (500 MHz, Chloroform-d) δ 7.77 (t, J=7.8 Hz, 1H), 7.57 (d, J=7.9 Hz, 4H), 7.54 (d, J=7.8 Hz, 2H), 7.43-7.36 (m, 8H), 7.30 (d, J=8.5 Hz, 16H), 7.27 (s, 4H), 7.21 (t, J=8.5 Hz, 8H), 7.09 (d, J=8.4 Hz, 12H), 6.78 (d, J=8.7 Hz, 4H), 5.70 (d, J=8.9 Hz, 4H), 3.56 (s, 4H), 1.33 (s, 54H)—see FIG. 11. $^{13}$C NMR (126 MHz, CDCl$_3$) δ 148.59, 148.50, 145.90, 144.40, 144.24, 141.01, 140.55, 139.01, 136.89, 132.48, 131.88, 130.87, 130.84, 129.27, 128.17, 127.85, 127.53, 127.34, 127.17, 124.35, 124.26, 117.49, 113.26, 63.27, 34.50, 34.46, 31.57, 31.54—see FIG. 12. MS (MALDI-TOF) (m/z): [M]+calculated for C$_{127}$H$_{121}$NO$_2$, 1691.944; found, 1692.020.

Example 5

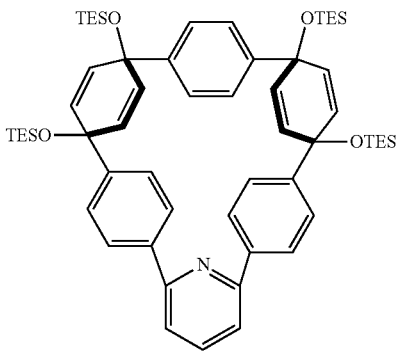

312

Figure 15:
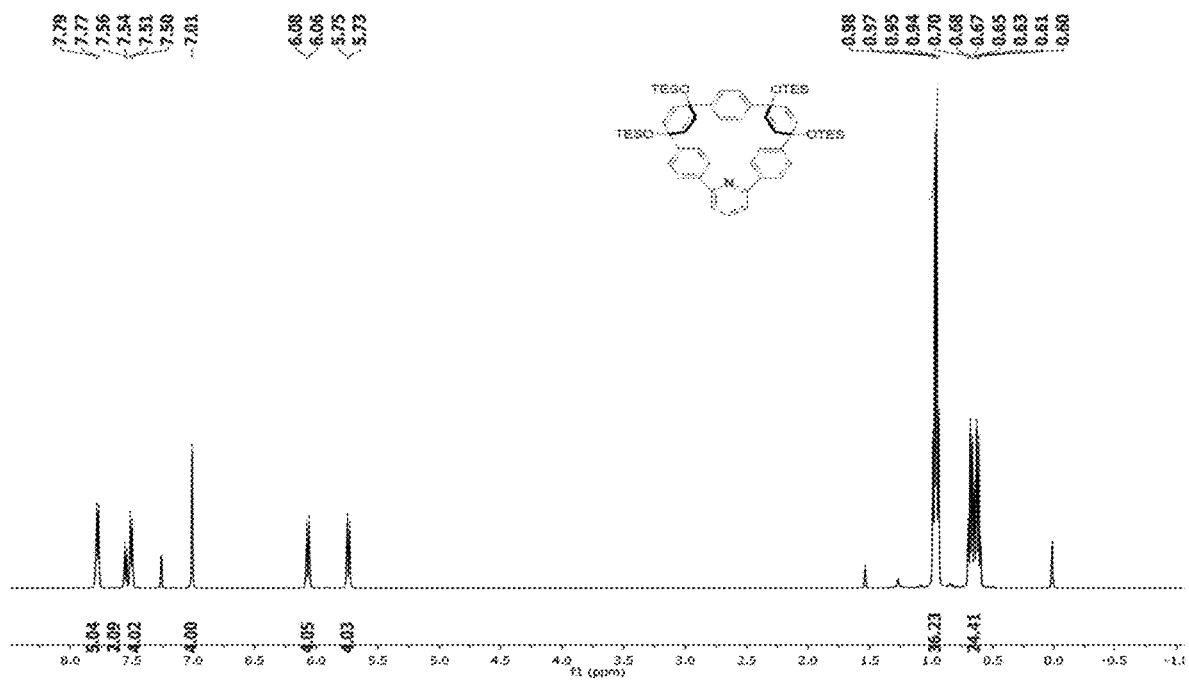
FIG. 15 is a $^1$H-NMR spectrum of nanohoop precursor embodiment 312.
Figure 16:
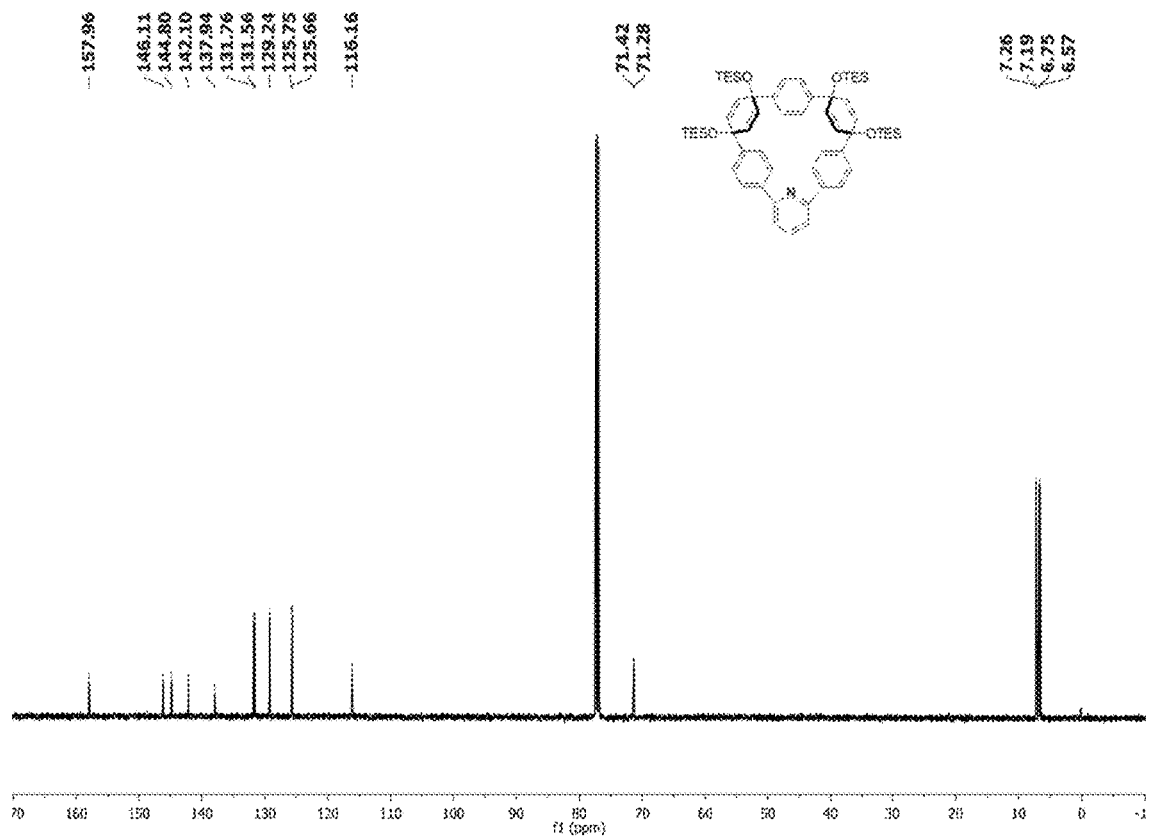
FIG. 16 is a $^{13}$C-NMR spectrum of nanohoop precursor embodiment 312.

To a 500 mL round bottom flask equipped with a stir bar, compound 300 (0.500 g, 0.432 mmol, 1.00 equiv.), 2,6-dibromopyridine (0.102 g, 0.432 mmol, 1.00 equiv.), and Pd SPhos G2 (0.033 g, 0.0432 mmol, 0.10 equiv.) were added. The flask was evacuated and back-filled with $N_2$ for about five times, followed by addition of 1,4-dioxane (200 mL). This solution was then vigorously sparged with $N_2$ for 30 minutes at which point it was then placed into an 80° C. oil bath for 30 minutes. At this point, an $N_2$ sparged aqueous solution of 2M $K_3PO_4$ (20.0 mL, 40.0 mmol, 92.6 equiv.) was added, quickly turning the solution to a bright yellow. The reaction was monitored until all starting material was consumed (typically 1 hour), at which point the solution was allowed to cool to room temperature. After removal of the solvent via rotary evaporation, the resulting yellow/brown oil was extracted with DCM (3×75 mL), followed by washing of the combined organic phases with $H_2O$ (3×100 mL), brine (1×100 mL), and finally placed over sodium sulfate. Removal of the organic phase gave a yellow oil, which, was then chromatographed (40% DCM/Hexanes, $SiO_2$) to give compound 312 as a white solid (0.271 g, 64%). On larger scale reactions, the desired product 312 can be isolated via the addition of acetone (5 mL) to the yellow oil obtained after workup, followed by sonication and collection of the solid via filtration to give compound 312 as a white solid. $^1H$ NMR (500 MHz, Chloroform-d) δ 7.83-7.73 (m, 5H), 7.55 (d, J=7.5 Hz, 2H), 7.50 (d, J=7.6 Hz, 4H), 7.01 (s, 4H), 6.07 (d, J=8.9 Hz, 4H), 5.74 (d, J=8.8 Hz, 4H), 1.04-0.91 (m, 36H), 0.78-0.57 (m, 24H)—see FIG. 15; $^{13}C$ NMR (126 MHz, $CDCl_3$) δ 157.96, 146.11, 144.80, 142.10, 137.94, 131.76, 131.56, 129.24, 125.75, 125.66, 116.16, 71.42, 71.28, 7.26, 7.19, 6.75, 6.57—see FIG. 16; HRMS (ESI-TOF) (m/z): [M]+calculated for $C_{59}H_{83}NO_4Si_4$, 981.5400; found, 981.5406.

Example 6

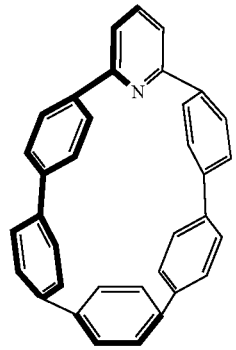

314

Figure 17:
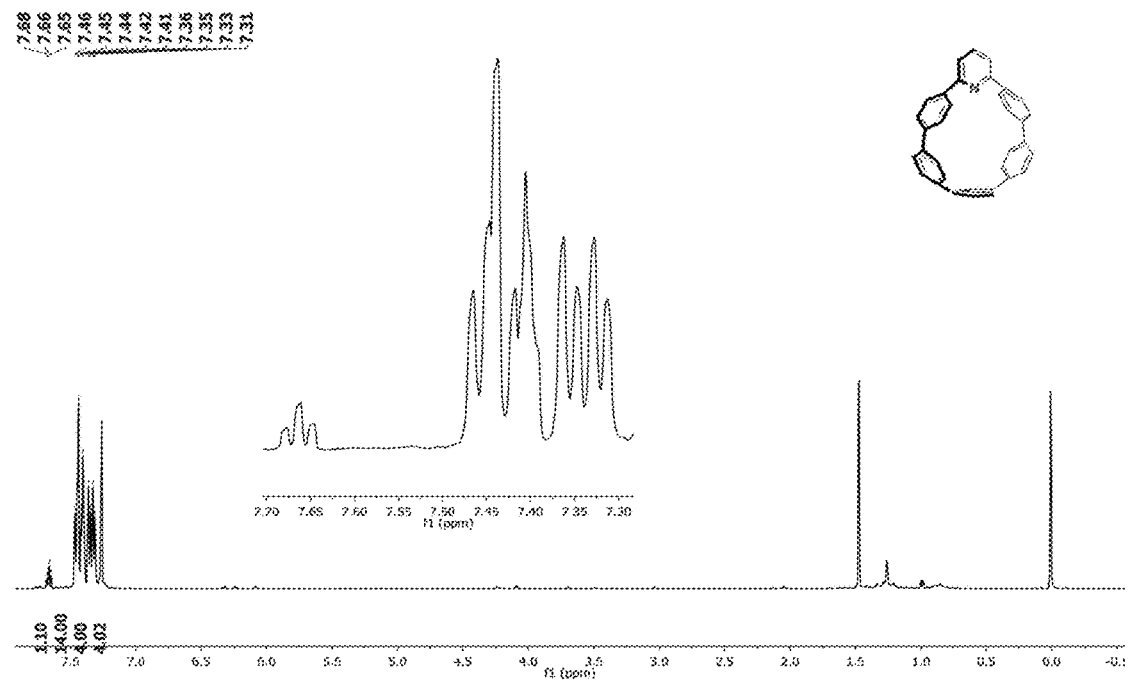
FIG. 17 is a $^1$H-NMR spectrum of nanohoop compound embodiment 314.
Figure 18:
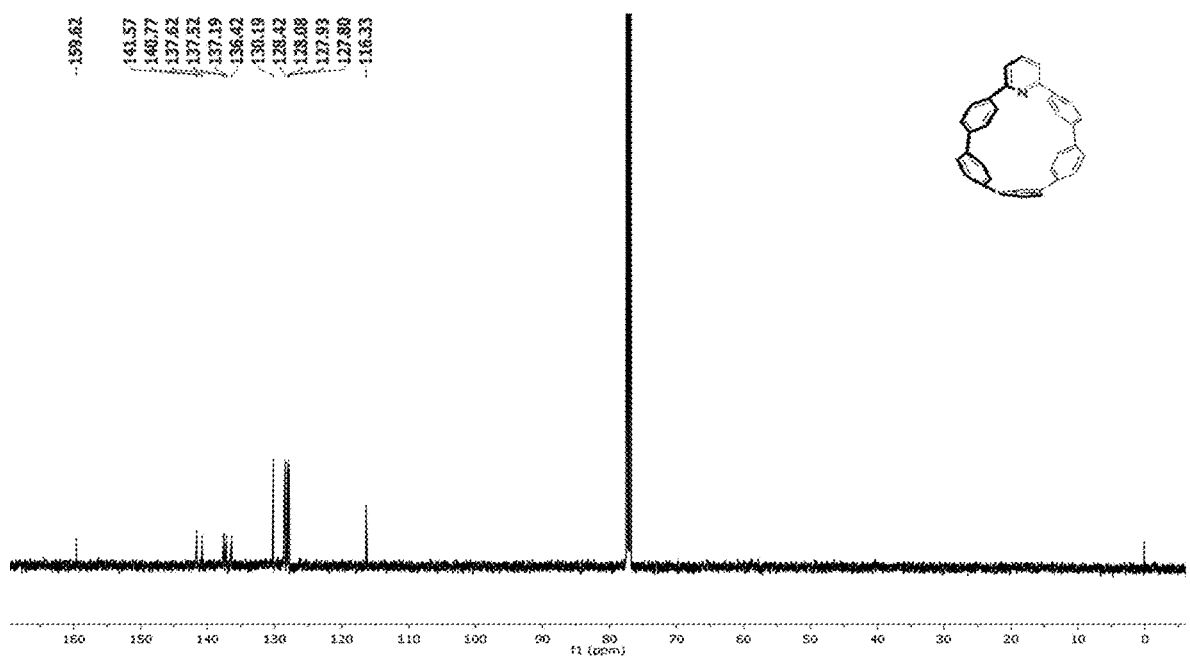
FIG. 18 is a $^{13}$C-NMR spectrum of nanohoop compound embodiment 314.

To a flame-dried 100 mL round bottom flask equipped with a stir bar, compound 312 (0.270 g, 0.270 mmol, 1.00 equiv.), followed by THF (20 mL) was added. To this solution was slowly added TBAF (1 M in THF, 2.20 mmol, 2.20 mL, 8.00 equiv.), resulting in a tan suspension. After stirring for 1 hour, the THF was removed via rotary evaporation, followed by addition of $H_2O$ (20 mL) resulting in a white precipitate. The white solid was collected via filtration, washed with $H_2O$ (50 mL), DCM (5 mL) and was then transferred to a flame-dried 100 mL RBF with stir bar. After addition of THF (20 mL), $H_2SnCl_4$ (5 equiv.) was added dropwise, turning the colorless solution to a bright orange over 20 minutes. After stirring for 1 hour, the solution was neutralized with 1M NaOH, quickly turning the solution from bright orange to bright yellow. The THF was removed via rotary evaporation, followed extraction of the resulting yellow/orange aqueous suspension with DCM (3×50 mL). The combined organic phases were washed with $H_2O$ (3×50 mL), brine (1×50 mL) and then dried over sodium sulfate. After removal of DCM under reduced pressure, the resulting yellow solid was run through a short alumina plug using DCM as eluent, providing compound 314 as a yellow solid (0.111 g, 90%). $^1H$ NMR (500 MHz, Chloroform-d) δ 7.81 (t, J=7.8 Hz, 1H), 7.68 (d, J=8.2 Hz, 4H), 7.58 (d, J=7.8 Hz, 2H), 7.56-7.46 (m, 16H), 7.36 (d, J=8.4 Hz, 4H), 7.33 (d, J=8.5 Hz, 4H)—see FIG. 17; $^{13}C$ NMR (126 MHz, $CDCl_3$) δ 158.93, 141.60, 140.40, 139.41, 138.17, 138.08, 137.97, 137.86, 137.04, 129.30, 128.22, 128.05, 127.93, 127.91, 127.36, 127.06, 117.48—see FIG. 18; HRMS (ESI-TOF) (m/z): [M]+calculated for $C_{35}H_{23}N$, 457.1831; found, 457.1843.

TABLE 2

Major electronic transitions for Compound 314 determined by TD-DFT method using B3lYP/6-31g

| Wavelength (nm) | Osc. Strength | Symmetry | Major contributions |
|---|---|---|---|
| 420.6389708 | 0.0998 | Singlet-A | HOMO->LUMO (97%) |
| 358.1470236 | 0.1503 | Singlet-A | H − 1->LUMO (12%), HOMO->L + 1 (87%) |
| 323.6571296 | 0.5588 | Singlet-A | H − 1->LUMO (81%), HOMO->L + 1 (11%) |
| 322.22714 | 0.0767 | Singlet-A | HOMO->L + 2 (89%) |
| 311.9313071 | 0.0514 | Singlet-A | H − 4->LUMO (12%), HOMO->L + 3 (77%) |
| 310.6495368 | 0.0262 | Singlet-A | H − 2->LUMO (20%), H − 1->L + 1 (70%) |
| 297.136885 | 0.2715 | Singlet-A | H − 2->LUMO (69%), H − 1->L + 1 (12%) |
| 294.3224609 | 0.0202 | Singlet-A | HOMO->L + 4 (66%) |
| 288.3534587 | 0.0163 | Singlet-A | H − 3->LUMO (65%) |
| 282.261438 | 0.0053 | Singlet-A | H − 1->L + 2 (33%), HOMO->L + 5 (30%), HOMO->L + 6 (12%) |
| 279.3046556 | 0.0002 | Singlet-A | H − 6->LUMO (10%), H − 3->L + 1 (57%), HOMO->L + 8 (11%) |

TABLE 2-continued

Major electronic transitions for Compound 314
determined by TD-DFT method using B3lYP/6-31g

| Wavelength (nm) | Osc. Strength | Symmetry | Major contributions |
|---|---|---|---|
| 278.5078434 | 0.0498 | Singlet-A | H − 2->L + 1 (12%), H − 1->L + 2 (36%), HOMO->L + 5 (32%) |

Example 7

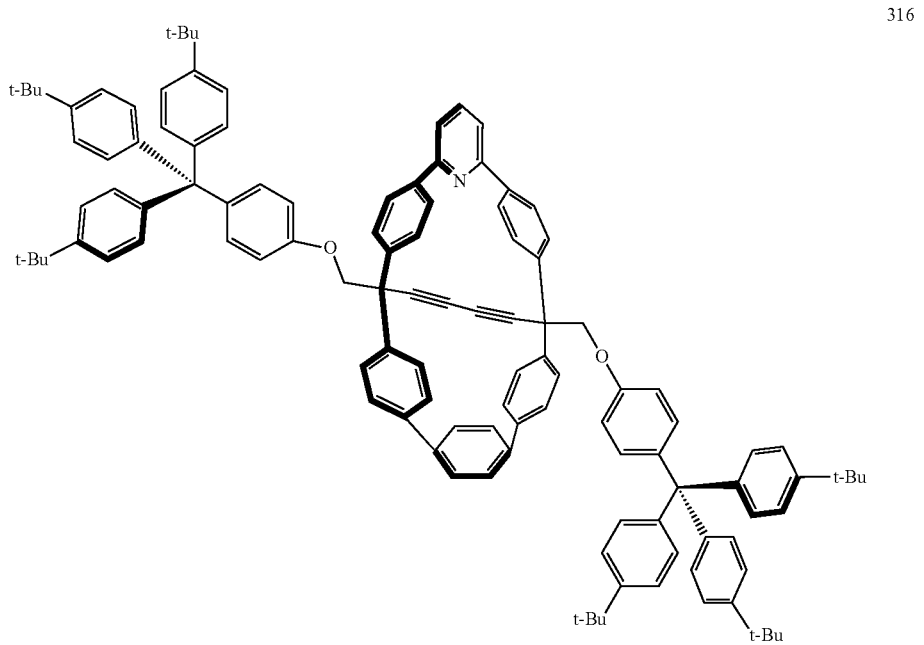

Figure 19:
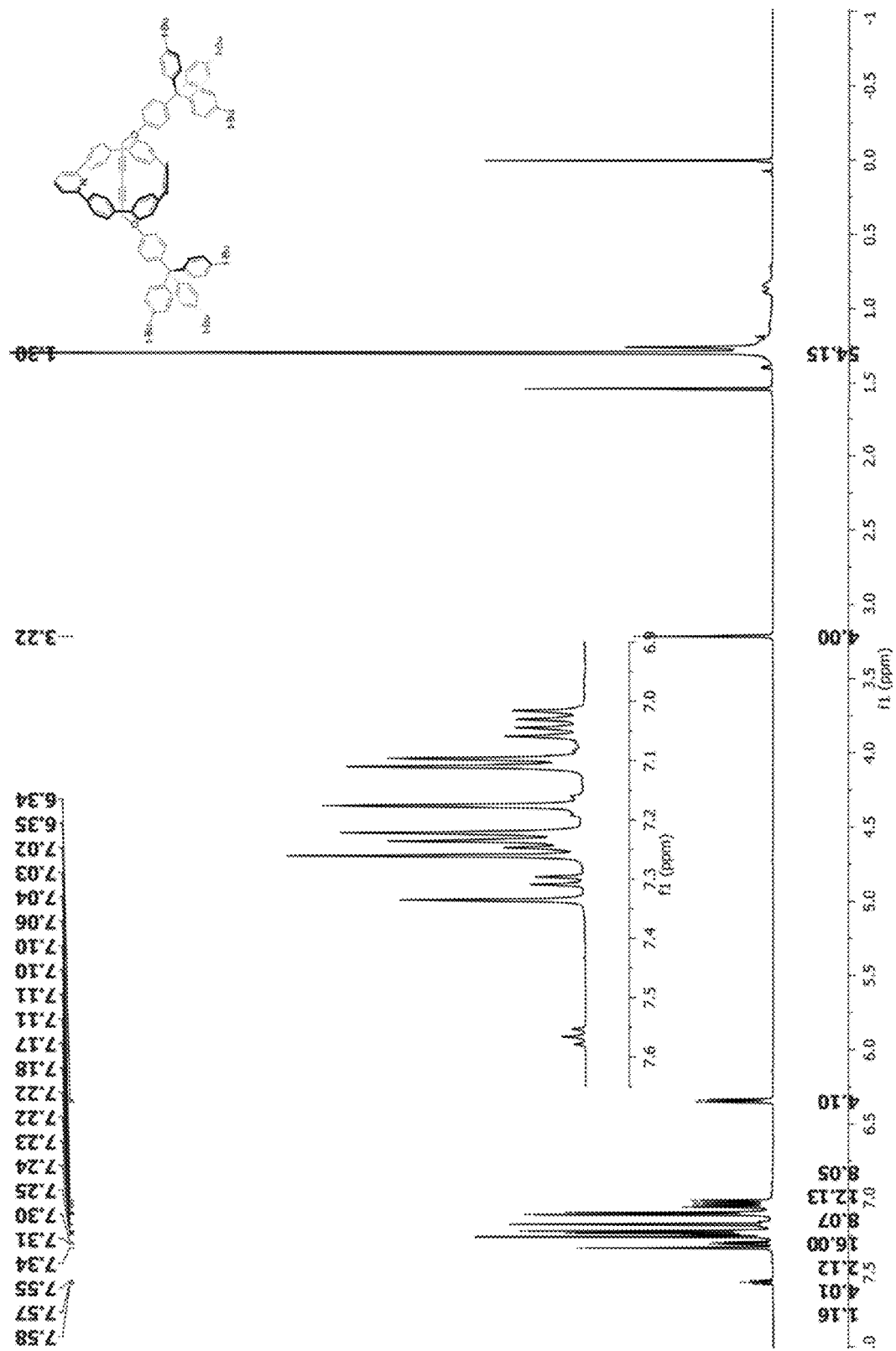
FIG. 19 is a $^1$H-NMR spectrum of a butadiyne-containing nanohoop rotaxane 316.
Figure 20:
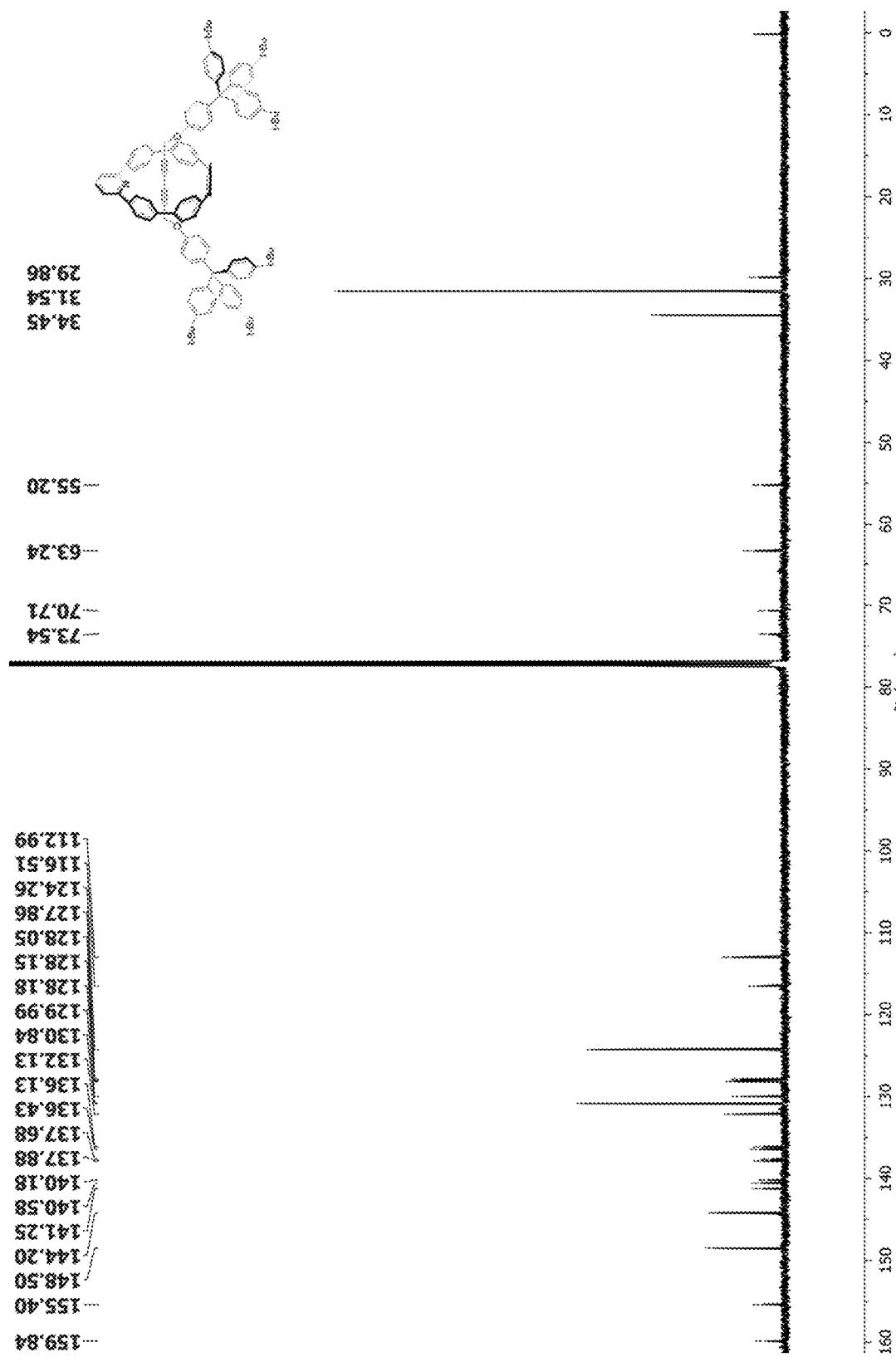
FIG. 20 is a $^{13}$C-NMR spectrum of a butadiyne-containing nanohoop rotaxane 316.

To a flame-dried 25 mL flask equipped with a stir bar, compound 314 (22.2 mg, 0.0485 mmol, 1.00 equiv.), $Cu(MeCN)_4PF_6$ (17.0 mg, 0.0461 mmol, 0.95 equiv.), bromo alkyne 228 (36.5 mg, 0.0582 mmol, 1.2 equiv.), terminal alkyne 218 (31.4 mg, 0.0582 mmol, 1.2 equiv.), and potassium bicarbonate (33.5 mg, 0.243 mmol, 5.00 equiv.) were added. The flask was then evacuated and refilled with $N_2$ for about five times. A septum was then placed on the flask, followed by the addition of 5 mL toluene. The reaction was then heated to 80° C. and the reaction progress was followed with TLC. On completion, the reaction was quenched with an $NH_3$-EDTA (2 mL) solution and then allowed to stir for 10 minutes. The layers were separated, followed by additional washing of the aqueous phase with DCM (2×20 mL). The combined organic phases were washed with $H_2O$ (3×20 mL), and brine (1×20 mL), and dried over sodium sulfate to give a bright yellow solid/oil. This oil was then loaded onto $SiO_2$, eluted with 15% EtOAc/Hexanes to separate butadiyne-containing nanohoop rotaxane 316 from unreacted compound 314. Next, crude butadiyne-containing nanohoop rotaxane 316 was purified on $SiO_2$ (30%DCM/Hexanes) to give the desired butadiyne-containing nanohoop rotaxane 316 as a yellow solid (40.4 mg, 54%). $^1$H NMR (600 MHz, Chloroform-d) δ 7.57 (t, J=7.7 Hz, 1H), 7.34 (s, 4H), 7.30 (d, J=7.7 Hz, 2H), 7.25-7.21 (m, 16H), 7.18 (d, J=1.1 Hz, 8H), 7.10 (d, J=8.6 Hz, 12H), 7.05 (d, J=8.8 Hz, 4H), 7.02 (d, J=8.9 Hz, 4H), 3.22 (s, 4H), 1.30 (s, 54H)—see FIG. 19; $^{13}$C NMR (151 MHz, $CDCl_3$) δ 159.84, 155.40, 148.50, 144.20, 141.25, 140.58, 140.18, 137.88, 137.68, 136.43, 136.13, 132.13, 130.84, 129.99, 128.18, 128.15, 128.05, 127.86, 124.26, 116.51, 112.99, 73.54, 70.71, 63.24, 55.20, 34.45, 31.54, 29.86—see FIG. 20; HRMS (ESI-TOF) (m/z): [M]+calculated for $C_{115}H_{113}NO_2$, 1539.8771; found, 1539.8601.

Example 8

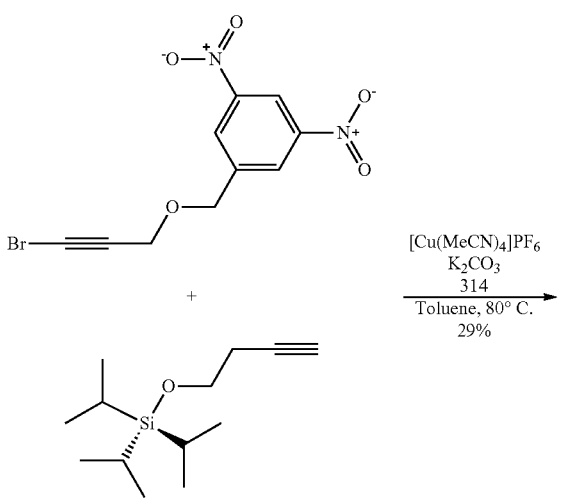

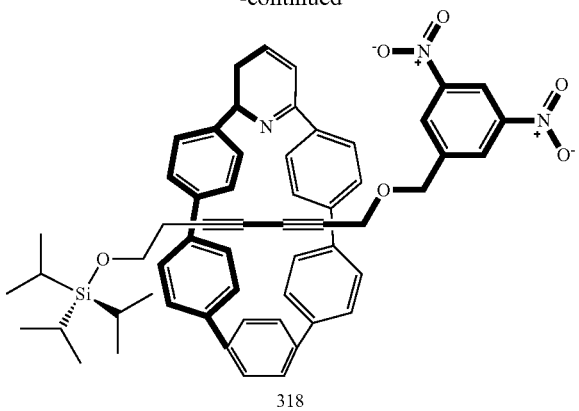

318

In this example, a procedure similar to that described in Example 3 was used to make nanohoop rotaxane compound 318.

Example 9

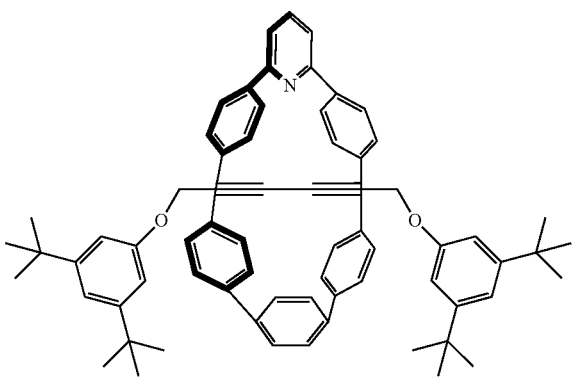

320

To a flame-dried 25 mL flask equipped with a stir bar was added nanohoop 314 (22.2 mg, 0.0485 mmol, 1.00 equiv.), Cu(MeCN)$_4$PF$_6$ (17.0 mg, 0.0461 mmol, 0.95 equiv.), the bromo alkyne (36.5 mg, 0.0582 mmol, 1.2 equiv.), and a terminal alkyne (31.4 mg, 0.0582 mmol, 1.2 equiv.), and potassium bicarbonate (33.5 mg, 0.243 mmol, 5.00 equiv.). The flask was then evacuated and refilled with N$_2$ 5 times. A septum was then placed on the flask, followed by the addition of 5 mL toluene. The reaction was then heated to 80= C. and the reaction progress was followed with TLC. On completion, the reaction was quenched with an NH$_3$-EDTA (2 mL) solution and then allowed to stir for 10 min. The layers were separated, followed by additional washing of the aqueous phase with DCM (2×20 mL). The combined organic phases were washed with H$_2$O (3×20 mL), and brine (1×20 mL), and dried over sodium sulfate to give a bright yellow solid/oil. This oil was then loaded onto SiO$_2$, eluted with 15% EtOAc/Hexanes to separate nanohoop 314 from 320. Next, crude 320 was purified on SiO2 (20%DCM/Hexanes) to give the desired rotaxane as a yellow solid (40.4 mg, 54%). $^1$H NMR (500 MHz, Chloroform-d) δ 7.73 (t, J=7.5, 1H), 7.50 (s, 4H), 7.46 (d, J=7.7, 2H), 7.33-7.28 (m, 8H), 7.20 (d, J=7.9, 4H), 7.01-6.91 (m, 6H), 6.28 (s, 4H), 2.92 (s, 4H), 1.28 (s, 36H). $^{13}$C NMR (126 MHz, CDCl$_3$) δ 159.93, 157.14, 152.10, 141.38, 141.14, 138.34, 137.78, 136.99, 136.46, 130.03, 128.60, 128.55, 128.23, 116.78, 115.17, 108.51, 74.33, 70.46, 55.00, 35.09, 31.63. HRMS (ESI-TOF) (m/z): [M]+calculated for C$_{69}$H$_{69}$NO$_2$, 943.5328; found, 943.5315.

Example 10

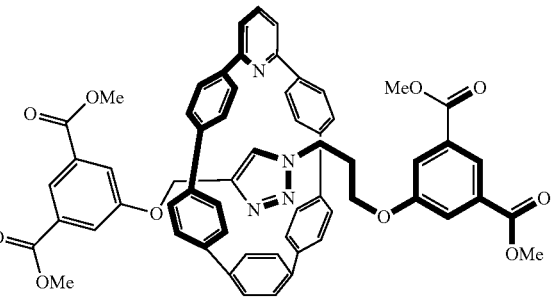

322

To a flame-dried 25 mL flask equipped with a stir bar was added nanohoop 314 (30.1 mg, 0.0658 mmol, 1.00 equiv.), Cu(MeCN)$_4$PF$_6$ (23.3 mg, 0.0625 mmol, 0.95 equiv.), azide (0.180 g, 0.658 mmol, 10.0 equiv.) and alkyne (0.163 g, 0.658 mmol, 10.0 equiv.). The flask was then evacuated and refilled with N$_2$ 5 times. A septum was then placed on the flask, followed by the addition of 10.0 mL DCM. The reaction was followed with TLC and allowed to stir until complete consumption of azide or alkyne. At this point, the reaction was quenched with an NH$_3$-EDTA (2 mL) and then allowed to stir for 10 min. The layers were separated, followed by additional washing of the aqueous phase with DCM (2×20 mL). The combined organic phases were washed with H$_2$O (3×20 mL), and brine (133 20 mL), and dried over sodium sulfate to give a bright yellow solid, which after chromatography (50% DCM/Hexanes to remove unreacted nanohoop 314, then 0→50% EtOAc/hexanes to elute 322, SiO$_2$), yielded the desired rotaxane 322 as a yellow oil (29.6 mg, 45%). $^1$H NMR (500 MHz, Chloroform-d) δ 8.39 (s, 1H), 8.36 (s, 1H), 7.90 (s, 2H), 7.75 (t, J=8.5 Hz, 1H), 7.64 (s, 2H), 7.60 (d, J=9.0 Hz, 2H), 7.55 (s, 2H), 7.53-7.44 (m, 8H), 7.38 (d, J=8.7 Hz, 4H), 7.21 (d, J=8.4 Hz, 2H), 7.10 (d, J=8.9 Hz, 2H), 7.01 (d, J=9.5 Hz, 2H), 6.38 (s, 1H), 5.18 (s, 2H), 4.06 (s, 6H), 3.97 (s, 6H), 1.68-1.64 (m, 2H), 1.42 (t, J=7.5 Hz, 2H), −1.40 (q, J=8.5 Hz, 2H). $^{13}$C NMR (126 MHz, CDCl$_3$) δ 166.48, 166.13, 159.96, 158.99, 158.60, 142.09, 141.51, 139.52, 137.92, 136.97, 135.85, 135.62, 132.28, 132.07, 130.32, 130.05, 129.97, 129.46, 128.62, 128.48, 127.87, 127.51, 126.58, 124.70, 123.80, 122.72, 122.19, 120.13, 119.37, 118.05, 64.08, 62.83, 52.77, 52.72, 44.96, 25.78.MS (ESI-TOF) (m/z): [M]+calculated for C$_{61}$H$_{50}$N$_4$O$_{10}$, 998.3527; found, 998.3525.

Example 11

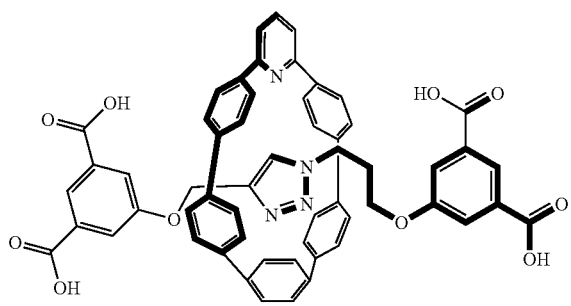

324

To a 50 mL flask equipped with a stir bar was added rotaxane 322 (20.2 mg, 0.0202 mmol, 1.00 equiv.) and NaOH (242.6 mg, 6.07 mmol, 300.0 equiv.) followed 20.0 mL of a 1:1 THF:H20 solution. The resulting suspension was heated at 55 °C. for 16h, at which point the THF was removed via rotary evaporation. The resulting bright green/yellow solution was then acidified with 1M HCl and extracted with EtOAc (3×25 mL). The combined organic phases were washed with $H_2O$ (3×20 mL), and brine (1×20 mL), and dried over sodium sulfate to give 324 as a bright yellow/orange solid (40.4 mg, 99%). $^1$H NMR (500 MHz, $D_2O$) δ 8.05 (s, 1H), 7.98 (s, 1H), 7.83-7.78 (m, 3H), 7.70 (d, J=8.0 Hz, 4H), 7.66 (d, J=8.5 Hz, 4H), 7.50 (d, J=7.8 Hz, 2H), 7.44 (d, J=8.9 Hz, 2H), 7.41-7.34 (m, 6H), 7.19 (d, J=8.4 Hz, 2H), 7.09 (d, J=8.9 Hz, 2H), 6.94 (d, J=8.4 Hz, 2H), 6.53 (s, 1H), 5.35 (s, 2H), 1.71 (t, J=7.0 Hz, 2H), 1.17-1.14 (m, 2H), −1.39 (q, J=8.4 Hz, 2H).$^{13}$C NMR (126 MHz, $D_2O$) δ 174.84, 173.98, 159.51, 157.81, 156.85, 141.98, 141.44, 138.75, 138.49, 138.32, 138.19, 136.63, 135.73, 135.40, 130.22, 129.81, 128.83, 128.58, 128.48, 128.29, 127.52, 127.43, 127.08, 125.25, 123.88, 122.99, 121.19, 118.70, 118.05, 117.64, 64.05, 61.80, 44.72, 24.

Example 12

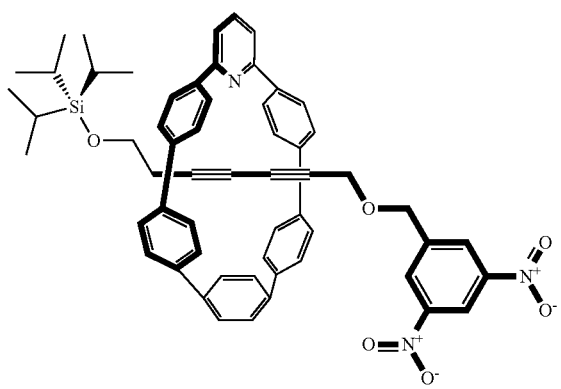

326

To a flame-dried 25 mL flask equipped with a stir bar was added nanohoop 314 (35.2 mg, 0.0770 mmol, 1.00 equiv.), $Cu(MeCN)_4PF_6$ (27.2 mg, 0.0731 mmol, 0.95 equiv.), bromo alkyne (72.8 mg, 0.231 mmol, 3.0 equiv.), terminal alkyne (52.3 mg, 0.231mmol, 3.0 equiv.), and potassium bicarbonate (53.1 mg, 0.385 mmol, 5.00 equiv.). The flask was then evacuated and refilled with $N_2$ 5 times. A septum was then placed on the flask, followed by the addition of 8.0 mL toluene. The reaction was then heated to 80° C. and the reaction progress was followed with TLC. On completion, the reaction was quenched with an $NH_3$-EDTA (2 mL) solution and then allowed to stir for 10 min. The layers were separated, followed by additional washing of the aqueous phase with DCM (2×20 mL). The combined organic phases were washed with $H_2O$ (3×20 mL), and brine (1×20 mL), and dried over sodium sulfate to give a bright yellow solid/oil. This oil was then loaded onto SiO2, eluted with 50% DCM/Hexanes to separate nanohoop 314 from 326. Next, crude 326 was purified via size exclusion chromatography to give the desired rotaxane as an orange foam/solid (20.1 mg, 29%). $^1$H NMR (500 MHz, Chloroform-d) δ 8.79 (s, 1H), 7.77 (t, J=7.7 Hz, 1H),), 7.69-7.65 (m, 8H), 7.57 (s, 2H), 7.45 (d, J=7.7 Hz, 2H), 7.41 (d, J=8.4 Hz, 2H), 7.31 (d, J=8.9 Hz, 2H), 7.19 (s, 2H), 7.10 (d, J=8.4 Hz, 2H), 6.88 (d, J=8.3 Hz, 2H), 6.80 (d, J=8.9 Hz, 2H), 3.74 (t, J=6.9 Hz, 2H), 2.42 (t, J=6.9 Hz, 2H), 1.90 (s, 2H), 1.77 (s, 2H), 1.09-1.08 (m, 21H).$^{13}$C NMR (126 MHz, $CDCl_3$) δ 159.92, 147.61, 144.06, 141.59, 139.64, 138.12, 137.31, 136.30, 136.17, 131.22, 131.15, 129.33, 129.06, 128.78, 128.06, 127.41, 127.15, 126.70, 126.55, 124.04, 117.29, 116.83, 83.64, 78.06, 72.76, 71.91, 67.20, 66.52, 61.77, 57.82, 25.18, 23.97, 18.16, 12.14. HRMS (ESI-TOF) (m/z): [M]+ calculated for $C_{58}H_{55}N_3O_6Si$, 917.3860; found, 917.3832.

Example 13

Figure 26:
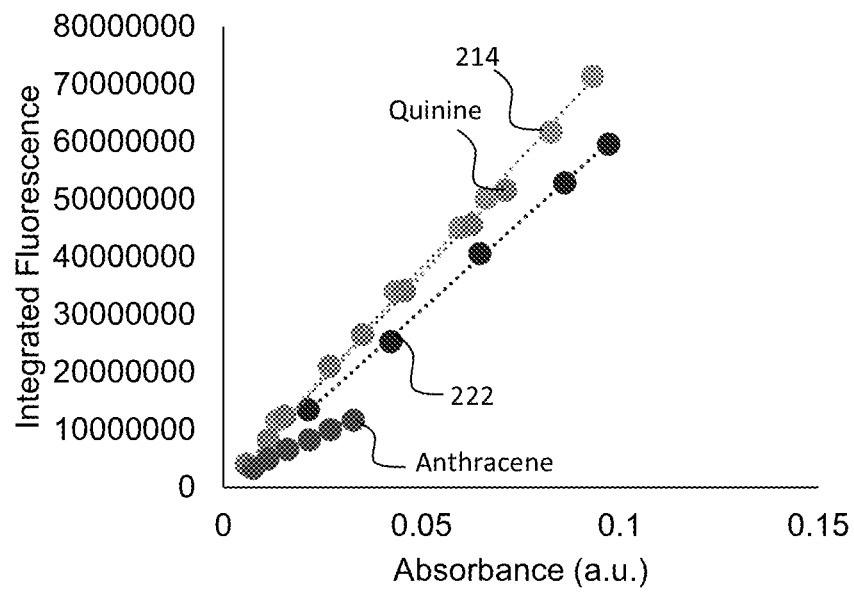
FIG. 26 is a graphic plot showing photophysical data comparing nanohoop compound embodiment 214 and triazole-containing rotaxane 222.
Figure 27:
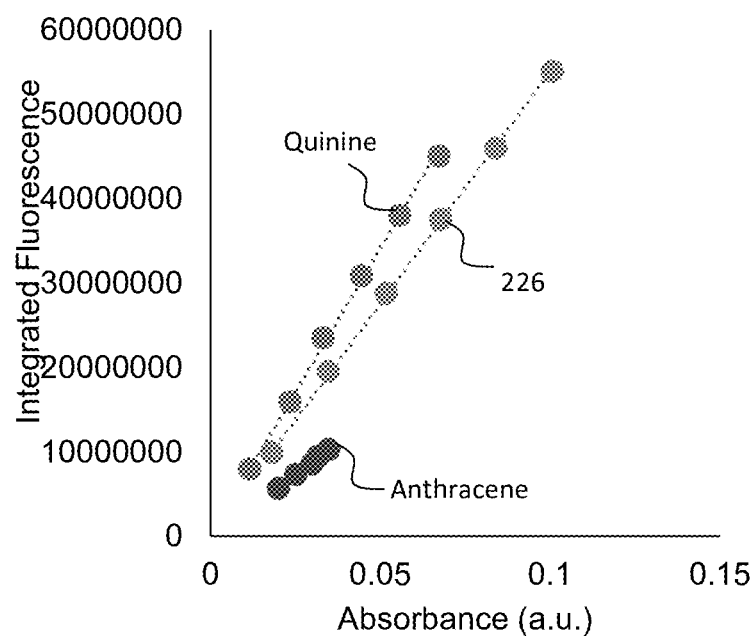
FIG. 27 is a graphic plot showing photophysical data of butadiyne-containing rotaxane 226.
Figure 28:
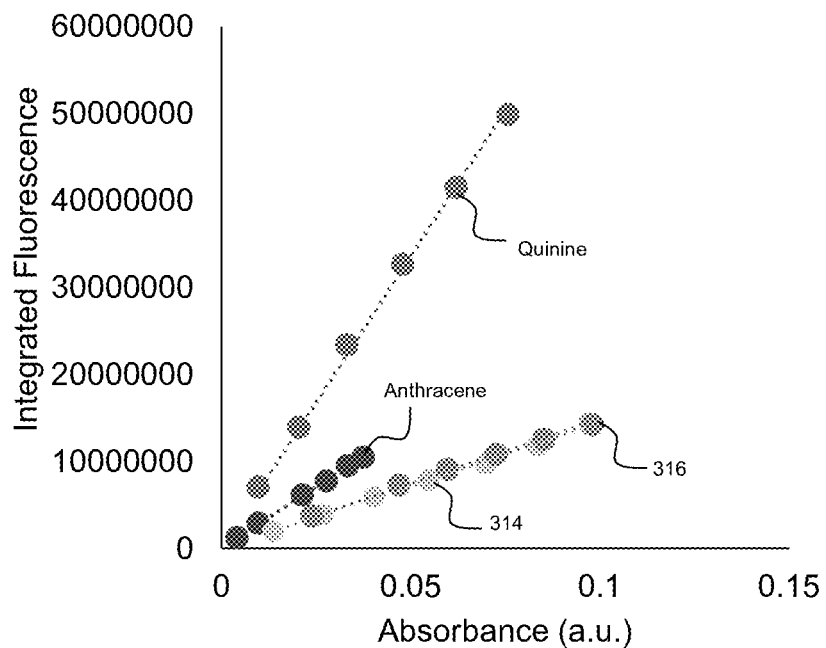
FIG. 28 is a graphic plot showing photophysical data of nanohoop compound embodiment 314 and butadiyne-containing nanohoop rotaxane 316.

In this example, the quantum yield of nanohoop compound embodiment 214, triazole-containing rotaxane 222 and alkyne-containing rotaxane 226, in dichloromethane (DCM) as a solvent was determined using anthracene (in ethanol as a solvent) and quinine sulfate (0.1 M $H_2SO_4$) as standards while exciting at 325 nm. The fluorescence of nanohoop compound embodiment 214, triazole-containing rotaxane 222 and alkyne-containing rotaxane 226 was integrated from 415-600 nm while anthracene was integrated from 360-480 nm, and quinine sulfate was integrated from 400-600 nm. While FIG. 26 depicts a graphic plot showing photophysical data comparing nanohoop compound embodiment 214 and triazole-containing rotaxane 222, FIG. 27 depicts a graphic plot showing photophysical data of rotaxane 226. Additionally, FIG. 28 depicts a graphic plot showing photophysical data comparing compound 314 and butadiyne-containing nanohoop rotaxane 316.

Example 14

In this example, diffraction intensities for nanohoop compound embodiment 214 and butadiyne-containing nanohoop rotaxane 316 were collected at 173 K on a Bruker Apex2 CCD diffractometer using CuKα radiation, λ=1.54178 Å. Space groups were determined based on intensity statistics. Absorption corrections were applied by SADABS. Structures were solved by direct methods and Fourier techniques and refined on $F^2$ using full matrix least-squares procedures. All non-H atoms were refined with anisotropic thermal parameters. Hydrogen atoms in both structures were refined in calculated positions in a rigid group model. There are two symmetrically independent main molecules in nanohoop compound embodiment 214. Thermal parameters for some of the terminal t-Bu groups in butadiyne-containing nanohoop rotaxane 316 are significantly elongated due to their flexibility or a disorder in the crystal structure. Two solvent molecules ($CH_2Cl_2$, 42 electrons) are highly disordered inside the main hoop in nanohoop compound embodiment 214 and were treated by SQUEEZE. Correction of the X-ray data by SQUEEZE is 334 electron/cell; the required value is 336 electron/cell. All calculations were performed by the Bruker SHELXL-2014 package.

Crystallographic Data for nanohoop compound embodiment 214: $C_{49}H_{35}Cl_4N$, $C_{47}H_{31}N.(CH_2Cl_2)_2$, M=779.58, 0.22×0.18×0.12 mm, T=173(2) K, Triclinic, space group P-1, a=12.3367(8) Å, b=15.3339(10) Å, c=22.9899(15) Å, α=98.146(3)°, β=91.411(3)°, γ=111.537(3)°, V=3990.6(3) Å$^3$, Z=4, $D_c$=1.298 Mg/m$^3$, μ(Cu)=2.963 mm$^{-1}$, F(000)=1616, $2\theta_{max}$=133.65°, 55669 reflections, 14063 independent reflections [$R_{int}$=0.0433], R1=0.0453, wR2=0.1229 and GOF=1.036 for 14063 reflections (867 parameters) with I>2σ(I), R1=0.0526, wR2=0.1268 and GOF=1.036 for all reflections, max/min residual electron density+0.191/-0.195 eÅ$^{-3}$. CCDC #1851935.

Crystallographic Data for butadiyne-containing nanohoop rotaxane 316: $C_{115}H_{113}NH_2$, M=1541.06, 0.15×0.12×0.04 mm, T=173(2) K, Triclinic, space group P-1, a=11.8752(4) Å, b=19.0169(6) Å, c=21.4758(7) Å, α=99.972(2)°, β=100.647(2)°, γ=103.394(2)°, V=4516.9(3) Å$^3$, Z=2, $D_c$=1.133 Mg/m$^3$, μ(Cu)=0.496 mm$^{-1}$, F(000)=1652, $2\theta_{max}$=133.42°, 64826 reflections, 15906 independent reflections [$R_{int}$=0.0531], R1=0.0593, wR2=0.1641 and GOF=1.054 for 15906 reflections (1063 parameters) with I>2σ(I), R1=0.0715, wR2=0.1764 and GOF=1.061 for all reflections, max/min residual electron density +0.732/-0.426 eÅ$^{-3}$. CCDC #1851936.

Example 15

Figure 5:
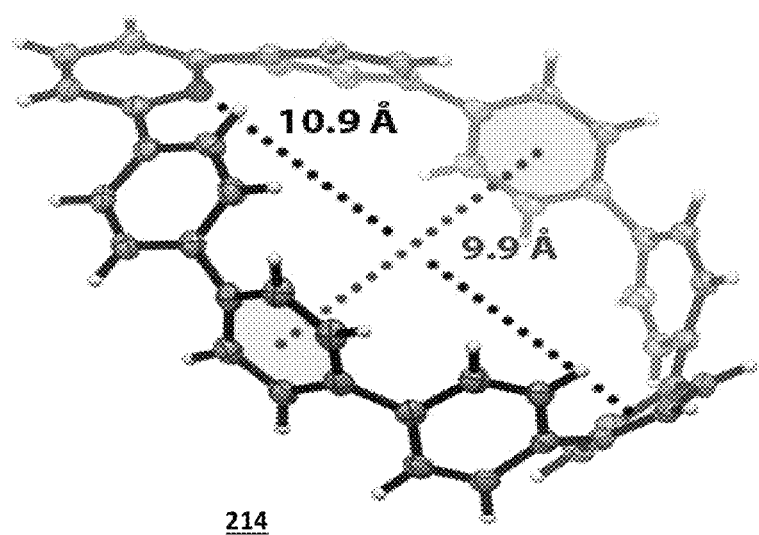
FIG. 5 is an ORTEP representation of the X-ray crystallographic structure of nanohoop compound embodiment 214.

In this example, certain physical characteristics of a representative nanohoop compound embodiment were evaluated. A representative single-crystal X-ray structure determination of nanohoop compound embodiment 214 is illustrated in FIG. 5. FIG. 5 shows an ORTEP image in which the solid-state structure of nanohoop compound embodiment 214 reveals a distance between meta-linked discrete ring system and distal para-linked aryl ring, and also a distance between two distal para-linked aryl ring. As shown in FIG. 5, the distance between meta-linked discrete ring system and distal para-linked aryl ring was been found to be 10.9 Å, while the distance between two para-linked aryl rings was been found to be 9.9 Å. Additionally, FIG. 5 also reveals a cavity size of approximately 10 Å, along with a strikingly large deviation)(Δ-16°) from the expected 180° "turn angle" of a typical 2,6-aryl-functionalized pyridine ring. Without being limited to a single theory, it currently is believed that this reduction in turn-angle, presumably owing to the strained nature of the nanohoop compound embodiment 214, likely renders the binding cavity of nanohoop compound embodiment 214 more sterically congested than unstrained meta-substituted macrocycles. In another representative embodiment, single-crystal X-ray structure determination of compound 314 revealed a cavity size of approximately 7.8 Å.

Example 16

Figure 8:
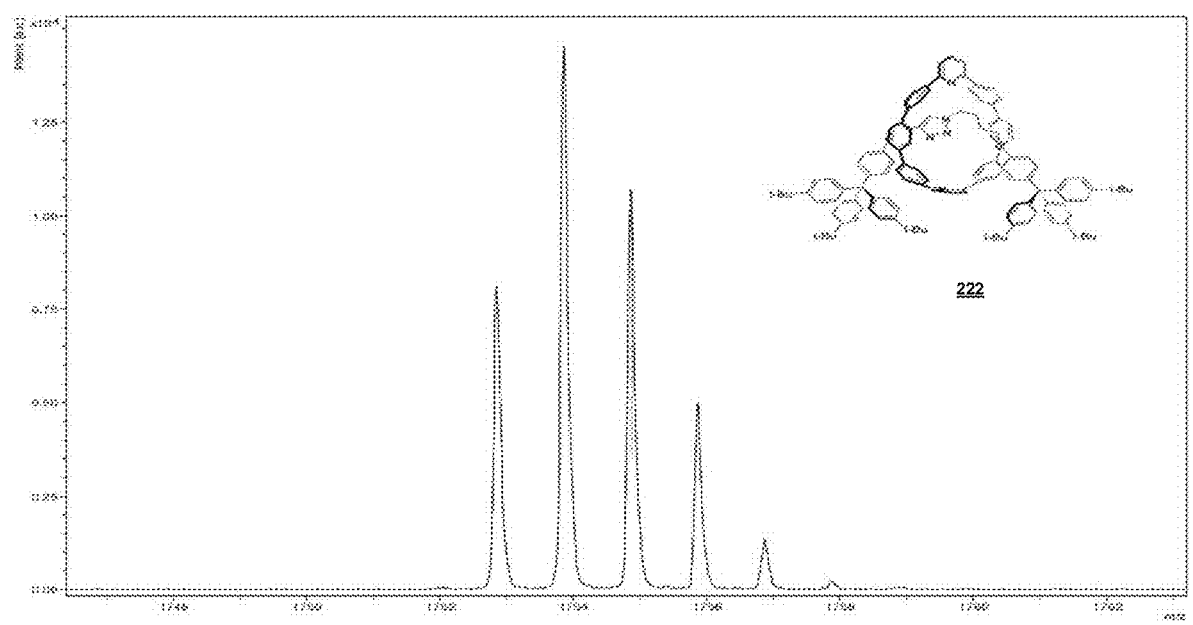
FIG. 8 is a mass spectrum of triazole-containing rotaxane 222.
Figure 13:
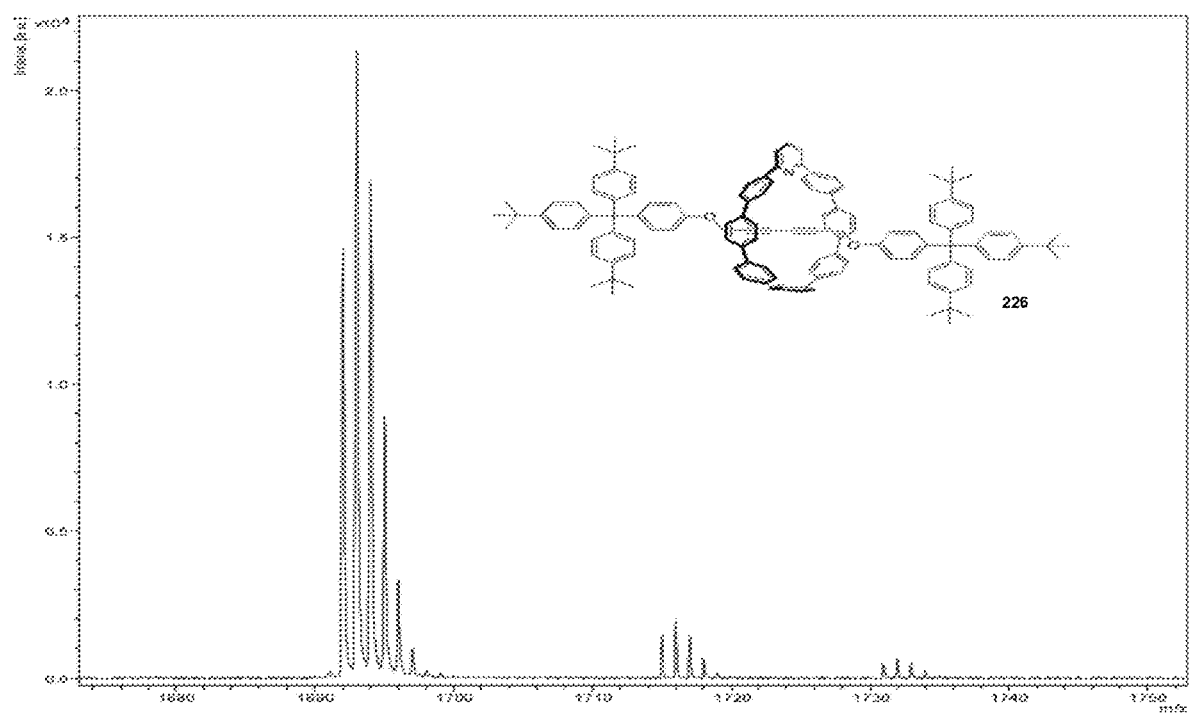
FIG. 13 is a mass spectrum of butadiyne-containing rotaxane 226.
Figure 14:
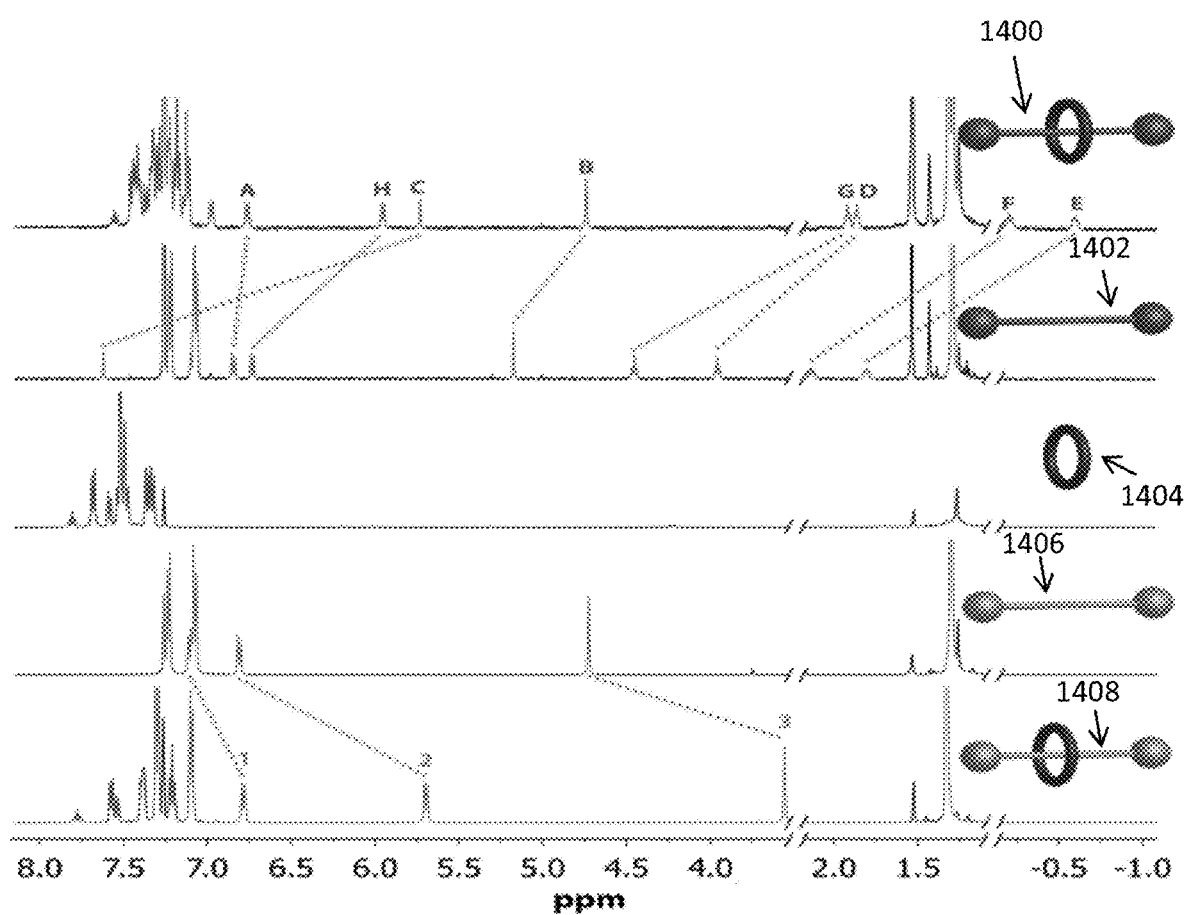
FIG. 14 shows partial $^1$H-NMR spectra comparing proton assignments of triazole-containing rotaxane 222 (illustrated as 1400, top spectrum), an unconstratined triazole compound (illustrated as 1402, second spectrum from top), nanohoop compound embodiment 214 (illustrated as 1404, middle spectrum), an unconstrained butadiyne compound (illustrated as 1406, second spectrum from bottom), and butadiyne-containing rotaxane 226 (illustrated as 1408, bottom spectrum).

In this example, mass spectral analysis of representative nanohoop-containing rotaxane compound embodiments was conducted. FIG. 8 shows a mass spectrum having a peak at m/z=1752.858 that is consistent with the formation of triazole-containing nanohoop rotaxane 222, while FIG. 13 shows a mass spectrum having a peak at m/z=1695.020 that is consistent with the formation of butadiyne-containing nanohoop rotaxane 226. Additionally, in some embodiments, comparative NMR studies can also confirm unique structural features of the nanohoop-containing rotaxane compound embodiments that can be synthesized using the nanohoop compounds disclosed herein. Exemplary NMR spectral comparisons of the nanohoop-containing rotaxane compound embodiments with that of the parent nanohoop compound can be seen in FIGS. 14A-14E. FIG. 14 shows partial $^1$H NMR spectra of triazole-containing nanohoop rotaxane 222 (illustrated as 1400 in FIG. 14, top spectrum), the unconstrained triazole compound (which for example, is the precursor for triazole-containing nanohoop rotaxane 222) (illustrated as 1402 in FIG. 14, second spectrum from top), nanohoop compound embodiment 214 (illustrated as 1404 in FIG. 14, middle spectrum), the unconstrained butadiyne compound (which, for example, is the precursor for butadiyne-containing nanohoop rotaxane 226) (illustrated as 1406 in FIG. 14, second spectrum from bottom), and butadiyne-containing nanohoop rotaxane 226 (illustrated as 1408 in FIG. 14, bottom spectrum), respectively. As depicted in FIG. 14, each of these $^1$H spectra show several unique features that illustrate the shielding ability of the nanohoop's cavity. While the spectral changes of nanohoop compound embodiment 214 (FIG. 14, middle spectrum) were rather modest, the encircled compound units that become constrained in the cavity (such as an unconstrained triazole compound (FIG. 14, second spectrum from top) and an unconstrained butadiyne compound (FIG. 14, second spectrum from bottom) were strongly influenced by the nanohoop. In the case of triazole-containing nanohoop rotaxane 222, nearly all protons belonging to the unconstrained triazole compound (FIG. 14, second spectrum from top) are shifted strongly upfield. Notably, the triazole Hc proton and methylene $H_{DG}$ protons are all shifted nearly 2 ppm units upfield. Additionally, similar to that of triazole-containing nanohoop rotaxane 226, several large upfield shifts were observed in alkyne-containing nanohoop rotaxane 226 (FIG. 14, bottom spectrum) relative to the unconstrained butadiyne compound (FIG. 14, second spectrum from bottom). Most notably, proton $H_3$ and aryl $H_2$ protons are both shifted upfield by nearly 1.5 ppm, indicative of being locked within the electron-rich nanohoop pore. The influence of the nanohoop compound on the compound that becomes constrained in its cavity (such as unconstrained butadiyne compound (FIG. 14, second spectrum from bottom)) is perhaps most apparent when compared with a similar constrained compound (FIG. 14, bottom spectrum), where aryl $H_2$ protons are shifted by only 0.2 ppm.

Example 17

Figure 9:
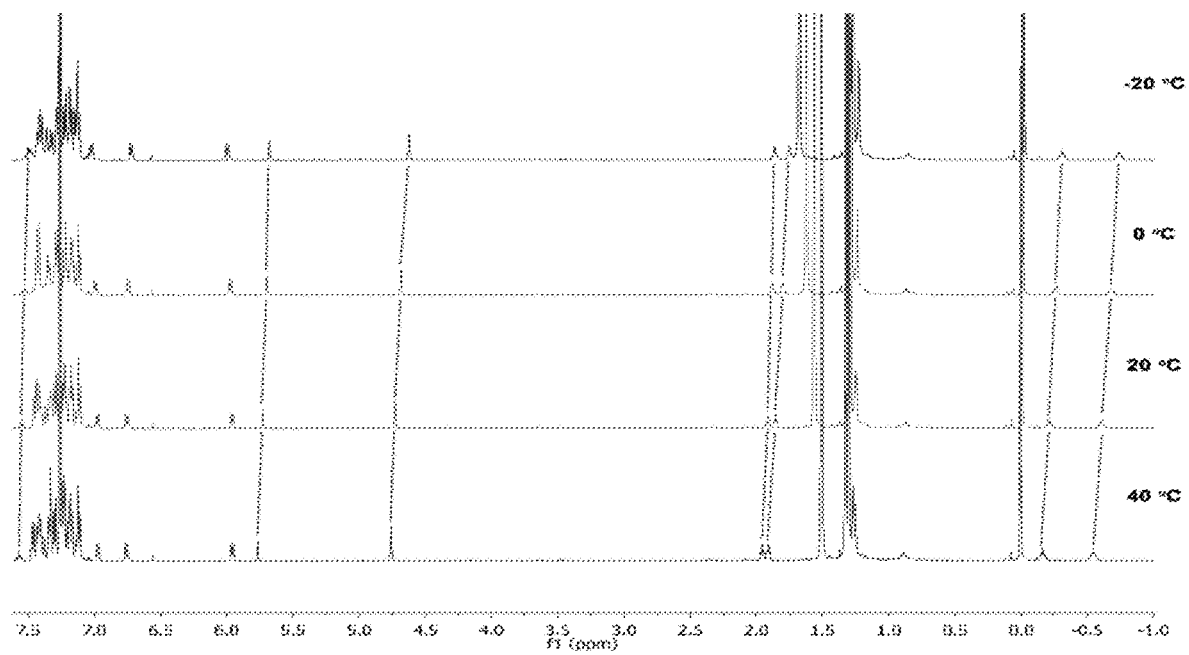
FIG. 9 is a variable temperature-NMR (VT-NMR) spectrum of triazole-containing rotaxane 222.
Figure 10:
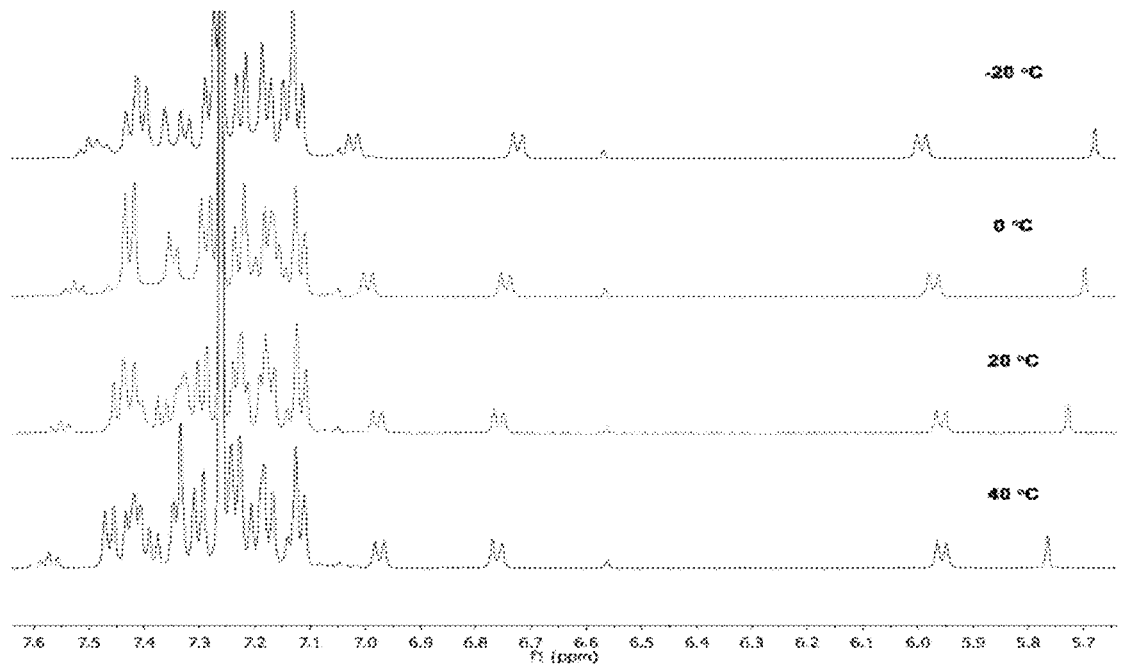
FIG. 10 is a zoomed view of a region of the VT-NMR spectrum of triazole-containing rotaxane 222 shown in FIG. 9.

In this example, variable-temperature nuclear magnetic resonance spectroscopy of nanohoop-containing rotaxane compound embodiments was conducted. In some embodiments, the nanohoop compound can have a restricted motion along an axis of the constrained compound (such as, triazole-containing nanohoop rotaxane 222 and/or butadiyne-containing nanohoop rotaxane 226), presumably due to interactions, such as metal coordination, hydrogen bonding, or the like. In one example, the restricted motion of the nanohoop structure can be confirmed by the proton resonances of the parent nanohoop compound in the presence of temperature changes using VT-NMR. Exemplary VT-NMR spectrum of triazole-containing nanohoop rotaxane 222 is shown in FIG. 9, and FIG. 10 shows a more detailed view of the VT-NMR spectrum of triazole-containing nanohoop rotaxane 222. As depicted in FIG. 9, the proton resonances belonging to the parent nanohoop structure of the rotaxanes (such as, triazole-containing nanohoop rotaxane 222) can be quite sensitive to temperature changes, where the corresponding peaks were found to be highly dynamic between −20 and 40° C., thus indicating that the nanohoop may experience restricted motion along the constrained compound.

Example 18

Figure 24:
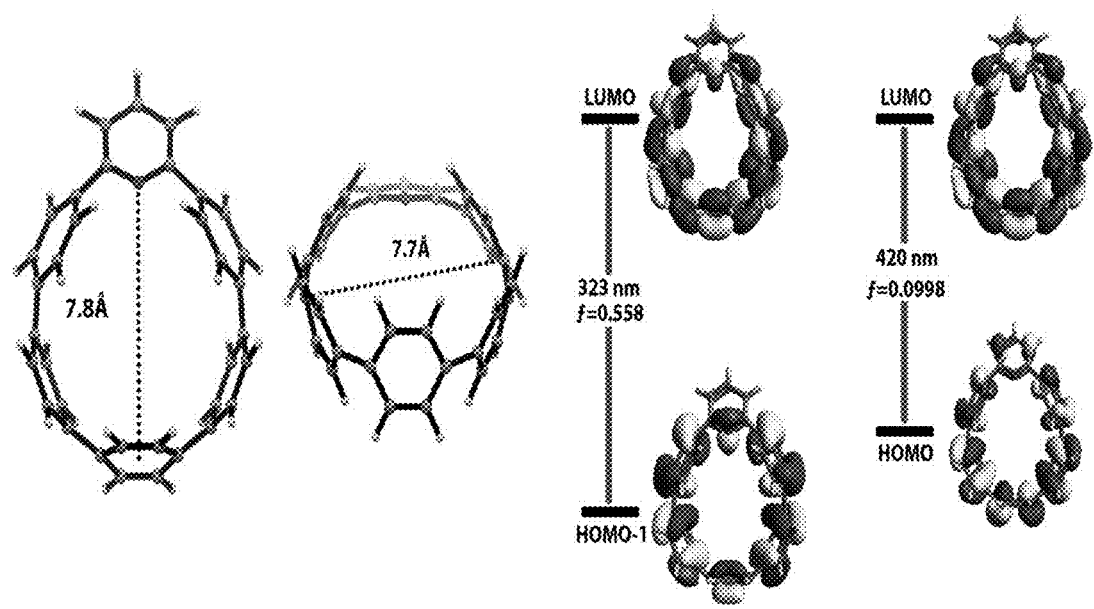
FIG. 24 is a time-dependent density functional theorem (TD-DFT) minimized structure of compound 314 showing (a) cavity dimensions, and (b) frontier molecular orbitals.

In this example, additional characterization techniques for nanohoop-containing rotaxane compound embodiments was conducted. Compound 314 has been found to have a calculated cavity size of only 7.8 Å (see FIG. 24), and the highly strained nature causes even further deviation)(Δ-23°) from planarity, rendering the binding site highly congested. In spite of the highly strained nature of the nanohoop, compound 314 has been readily found to form the desired [2]rotaxane, (e.g., butadiyne-containing nanohoop rotaxane 316) with substantially minimal or no loss in reaction efficiency. The formation of the butadiyne-containing nanohoop rotaxane 316 can be confirmed using, for example, high-resolution mass spectrum. An exemplary HRMS spectrum showed a peak at 1539.8601 that is consistent with the formation of butadiyne-containing nanohoop rotaxane 316. In some embodiments, NMR spectral studies can also be used to further characterize the structural features of compound 314, and the structural features of the corresponding butadiyne-containing nanohoop rotaxane 316. For example, the NMR spectrum of compound 314 shows that resonance of proton $H_x$ (FIG. 17) shifts even further upfield by additional 0.33 ppm, presumably as a result of the reduced diameter of compound 314 relative to nanohoop compound embodiment 214. This indicates that the reduced diameter of compound 314 results in an enhancement of the shielding ability of compound 314 on a constrained compound.

Figure 21:
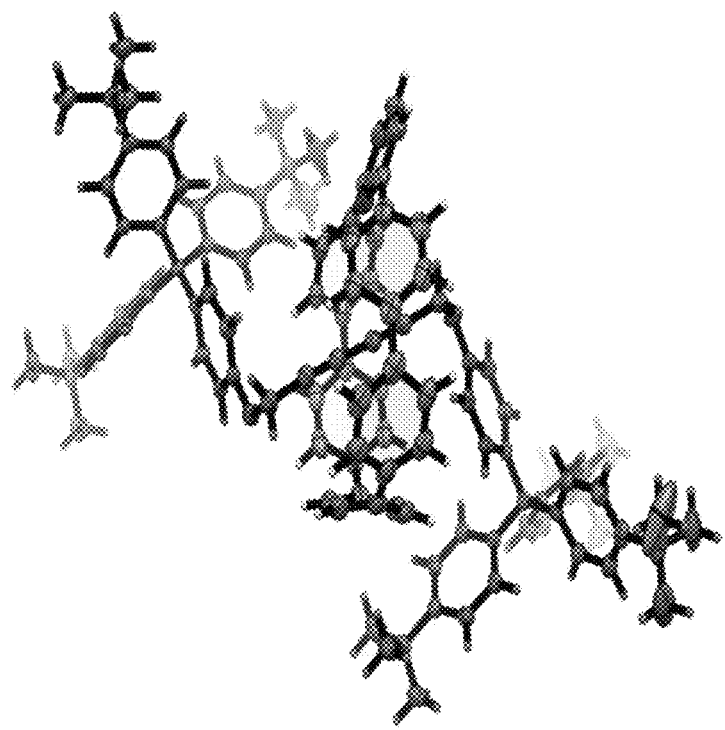
FIG. 21 is an ORTEP representation of the X-ray crystallographic structure of butadiyne-containing nanohoop rotaxane 316.
Figure 22:
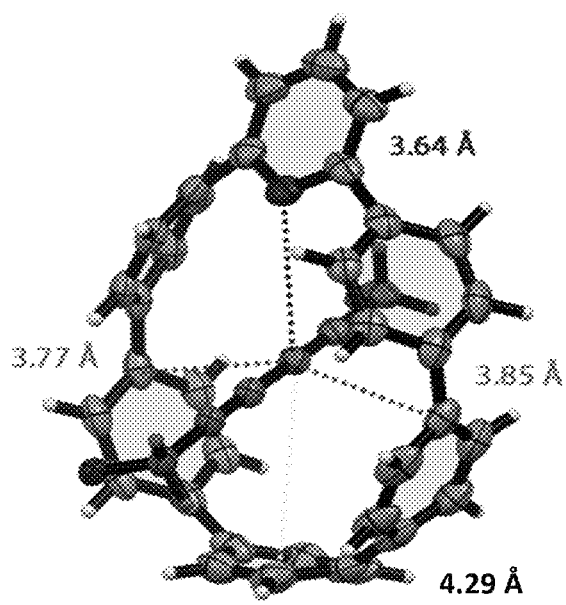
FIG. 22 is another view of the ORTEP representation of the X-ray crystallographic structure of butadiyne-containing nanohoop rotaxane 316 of FIG. 21 showing selected distances between the constrained compound (with trityl moieties removed for clarity) and butadiyne-containing nanohoop rotaxane 316.

Slow evaporation of a concentrated acetonitrile solution of butadiyne-containing nanohoop rotaxane 316 readily provided single crystals suitable for X-ray crystallography. Crystallographic analysis of these single crystals (FIG. 21) confirmed the identity of butadiyne-containing nanohoop rotaxane 316 as well as provided a better understanding of the congested nature of butadiyne-containing nanohoop rotaxane 316. As shown in FIGS. 21 and 22, the cavity of butadiyne-containing nanohoop rotaxane 316 is nearly a perfect fit for the alkyne compound that becomes constrained in the cavity (FIG. 22) and, interestingly, there was no solvent observed in the crystal structure. Based on these observations, it can be contemplated that large, traditional trityl-based stopper groups may not be necessary for the rotaxane formation with butadiyne-containing nanohoop rotaxane 316.

Figure 23:
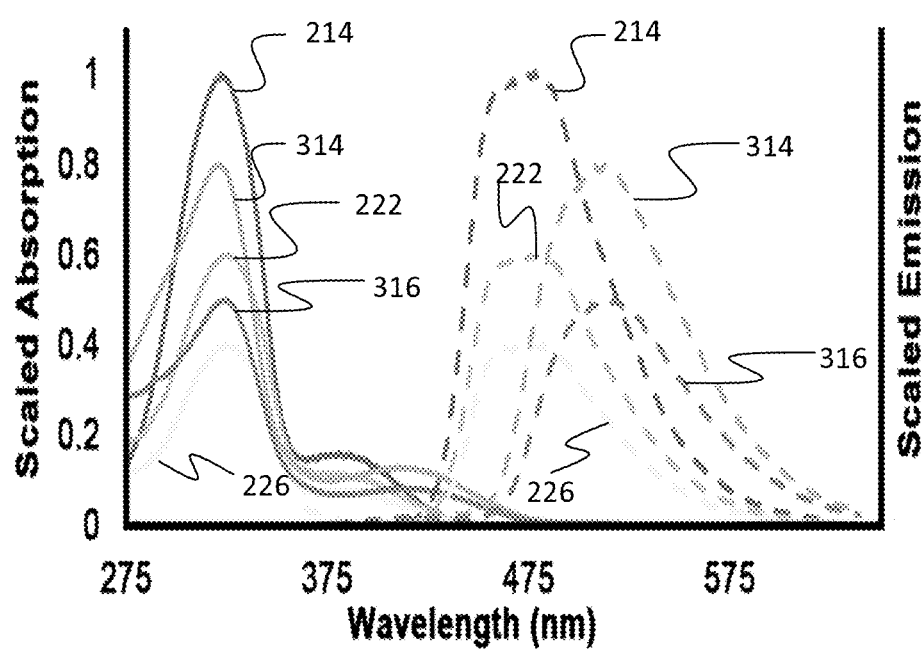
FIG. 23 is a combined UV-Vis absorbance (solid lines) and fluorescence spectrum (dashed lines) illustrating results obtained from UV-Vis and fluorescence analysis of nanohoop compound embodiment 214, triazole-containing rotaxane 222, butadiyne-containing rotaxane 226, nanohoop compound embodiment 314, and butadiyne-containing nanohoop rotaxane 316.

The effect of the substitution pattern change, e.g., from para to meta-position of the aryl rings in the discrete ring systems of the nanohoop compounds disclosed herein, as well as the impact of the rotaxane formation on the nanohoop electronic structure can be understood by evaluating their optoelectronic properties. In some embodiments, the UV-Vis absorption and emission spectra of nanohoop compound embodiment 214, compound 314, triazole-containing rotaxane 222, alkyne-containing rotaxane 226 and butadiyne-containing nanohoop rotaxane 316 were evaluated. Solely by way of example, FIG. 23 shows absorption and emission spectra of nanohoop compound embodiment 214 and compound 314, and compares with those of triazole-containing rotaxane 222, and alkyne [2]rotaxanes 226 and butadiyne-containing nanohoop rotaxane 316. Each of the nanohoop compounds (e.g., nanohoop compound embodiment 214, and butadiyne-containing nanohoop rotaxane 316) as well as the corresponding [2]rotaxanes are highly emissive. While certain [n]CPPs and related nanohoops can exhibit size-dependent fluorescence properties, the absorption and the emission spectra confirmed that replacing a single para-linked benzene with a 2,6-pyridine strongly impacted the photophysical properties. For example, in the case of compound 314, which is a [6]CPP derivative, an emission maximum centered at 509 nm was observed. Interestingly, owing to orbital symmetry and rigidity of smaller [n]CPPs, a corresponding conventional [6]CPP, is non-emissive, suggesting that the substitution of the 2,6-pyridine ring causes a breakage of orbital symmetry (See FIGS. 24 and 25, respectively). In some embodiments, these fluorescent properties can readily be transferred to the corresponding rotaxanes with minimal loss in ε or $\varphi_F$ (See Tables 2 and 3, respectively, for all exemplary photophysical data). Thus, in some embodiments, in addition to exploring different sizes and compositions of the termini on the alkyne and/or triazole moieties, functionalization of the nanohoop itself can be evaluated to understand the factors that impact this emission behavior using the absorption and the emission spectra.

Figure 30:
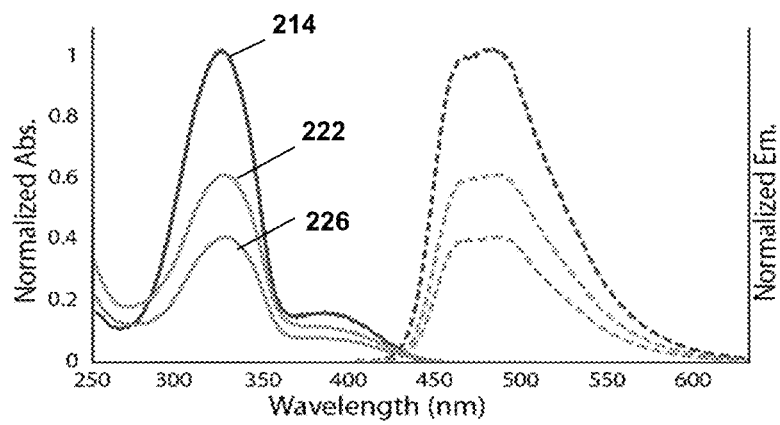
FIG. 30 is a combined UV-Vis absorbance (solid lines) and fluorescence spectrum (dashed lines) illustrating results obtained from UV-Vis and fluorescence analysis of nanohoop compound embodiment 214, triazole-containing rotaxane 222, and butadiyne-containing rotaxane 226.

In an exemplary embodiments, the UV-Vis absorption and emission spectra of nanohoop compound embodiment 214, triazole-containing rotaxane 222, and alkyne-containing rotaxane 226 were evaluated. Exemplary results are depicted in FIG. 30, and the photophysical data is summarized in Table 3. For example, Table 3 summarizes photophysical properties of nanohoop compound embodiment 214, triazole-containing rotaxane 222, and alkyne-containing rotaxane 226, and compares these properties with those of conventional [8]CPP and aza [8]CPP, respectively.

TABLE 3

| Compound | $\lambda_{abs}$ (nm) | ε (M$^{-1}$ cm$^{-1}$) | $\lambda_{em}$ (nm) | $\varphi_F$ |
|---|---|---|---|---|
| [8]CPP | 340 | 1.0 × 10$^5$ | 533 | 0.10 |
| Aza[8]CPP | 345 | 2.5 × 10$^5$ | 541 | N/A |
| 214 | 323 | 7.0 × 10$^4$ | 476 | 0.62 |
| 222 | 325 | 2.9 × 10$^4$ | 477 | 0.50 |
| 226 | 325 | 4.2 × 10$^4$ | 479 | 0.53 |

Figure 29:
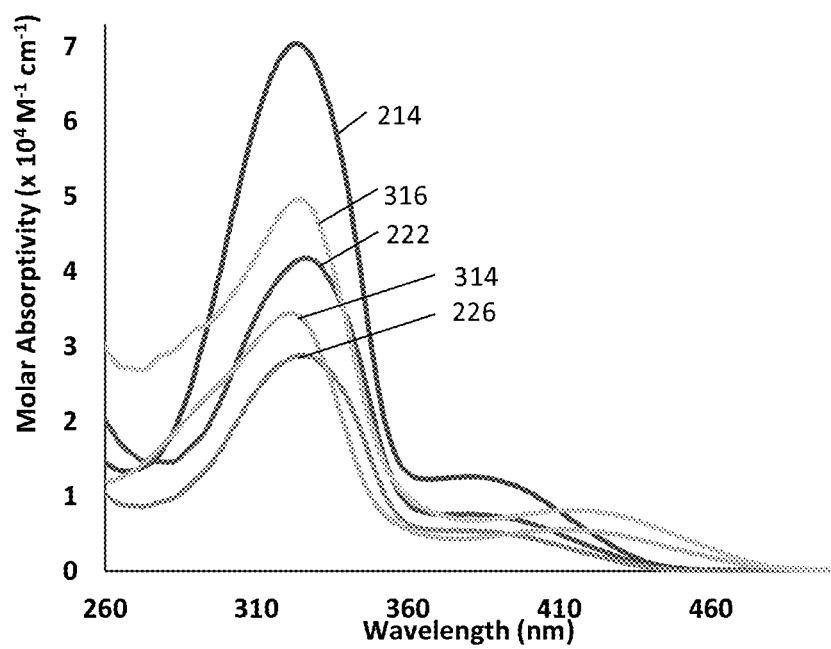
FIG. 29 is a graphic plot showing molar absorptivities of nanohoop compound embodiment 214, nanohoop compound embodiment 314, triazole-containing rotaxane 222, butadiyne-containing rotaxane 226, and butadiyne-containing nanohoop rotaxane 316.

Comparing nanohoop compound embodiment 214 to [8]CPP and aza[8]CPP, respectively, Table 3 shows that major absorption and emission maxima have both blue-shifted and that the extinction coefficients are slightly reduced. Additionally, an absorption centered at 381 nm (e=1.26×10$^4$) can be observed in nanohoop compound embodiment 214 (FIG. 30). Through time-dependent density functional theorem (TD-DFT), this transition can be assigned to a HOMO-LUMO transition based on a calculated HOMO-LUMO oscillator strength (f) of 0.0805 for nanohoop compound embodiment 214. Interestingly, this is nearly four times higher than the TD-DFT predicted HOMO-LUMO f of both [8]CPP (f=0.0201) and aza[8]CPP (f=0.0201). As depicted FIG. 26 and FIG. 27 for triazole-containing rotaxane 222, and butadiyne-containing rotaxane 226, respectively, this increased f in nanohoop compound embodiment 214 may be attributed to a breakage of orbital symmetry which, presumably is a direct result of changing the linkage of the discrete ring system of the nanohoop from para to meta. Thus, these optical properties, in particular the emission properties, were readily transferred to the rotaxane structures with minimal loss in ε or φ$_F$. FIG. 29 provides a graphic plot showing molar absorptivities of nanohoop compound embodiment 214, nanohoop compound embodiment 314, triazole-containing rotaxane 222, butadiyne-containing rotaxane 226, and butadiyne-containing nanohoop rotaxane 316.

Figure 31:
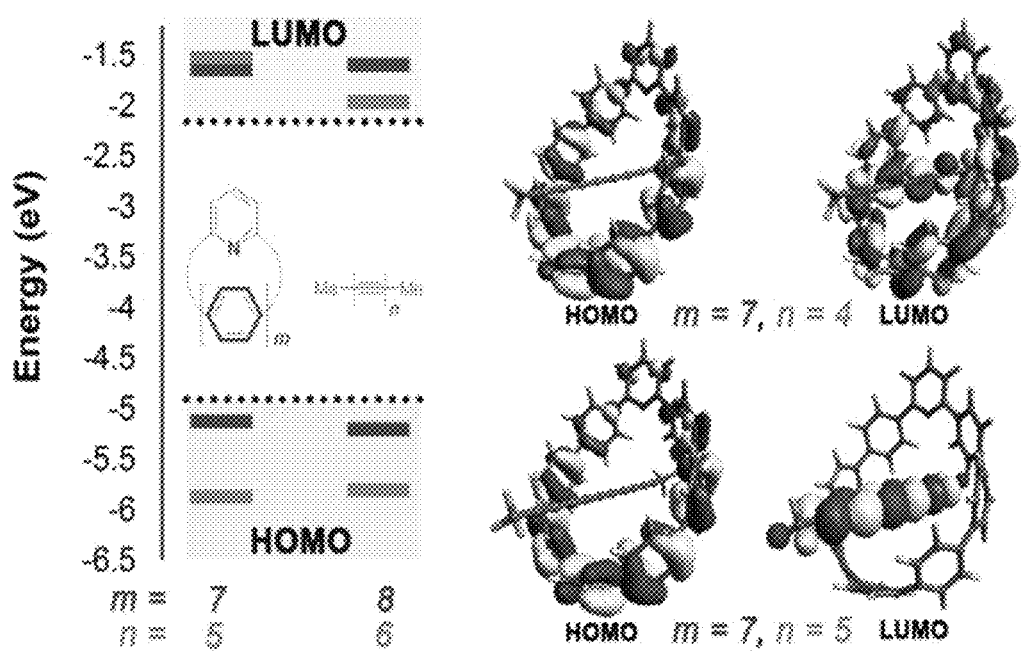
FIG. 31 is a time-dependent density functional theorem (TD-DFT) absorbance plot for nanohoop compound embodiment 214 and butadiyne-containing rotaxane 226.

In some embodiments, the nanohoop's extended conjugation can be leveraged to modify the electronic structure (e.g. HOMO-LUMO energy levels, photophysics, etc.) of a corrresponding polyyne constrained compound in rotaxane embodiments. Exemplary results are provided in FIG. 31, which shows DFT calculated HOMO-LUMO energy levels. For example, the HOMO-LUMO energy levels of a family of meta-pyridine-embedded nanohoop ligands ranging from 5 to 9 aryl rings can be calculated. Next, the HOMO-LUMO energy levels of methyl-terminated polyynes ranging from the 2 to 9 alkyne units (see FIG. 31) can be calculated. The LUMO energy of a butadiyne constrained compound (such as, the butadiyne component of the butadiyne-containing rotaxane 226) is more than a full electron volt higher in energy than the LUMO energy of nanohoop compound embodiment 214. However, as the number of alkyne units increases to 4 (as in a tetryne), the LUMO energy is sufficiently lowered to the level of nanohoop compound embodiment 214 (FIG. 31, chart on left), suggesting that orbital mixing (or electronic communcation) can take place. Additionally, increasing the constrained compound to 5 alkynes reduced the LUMO energy level of the polyyne to an energy level lower than that of the LUMO of nanohoop compound embodiment 214, implying that the orbitals should be separated, with the HOMO residing on the nanohoop and the LUMO residing the on the constrained compound. In another example, two polyyne-containing pseudorotaxane structures with nanohoop compound embodiment 214 were calculated, where the constrained compound length was either 4 and 5 alkyne units. Exemplary results are provided in FIG. 31 (structures on the right). As depicted, the resulting orbital plots show a mixed orbital system in the case of 4 alkynes and completely separated orbital system in the case of 5 alkynes.

Example 19

Figure 32:
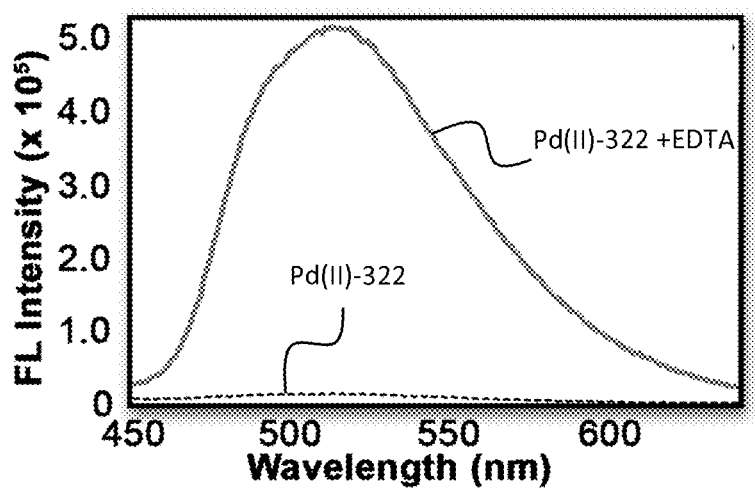
FIG. 32 shows emission spectra (8.6 µM, CHCl$_3$) for a nanohoop-containing rotaxane compound embodiment without coordinated Pd (solid line) and with coordinated Pd (dotted line).

In this example, the effects of metalation on an exemplary nanohoop-containing rotaxane compound embodiment was evaluated in both the solid state and solution through single-crystal X-ray crystallography, 1 HNMR titrations, and fluorescence spectroscopy. In the solid-state, without a coordinated metal, the nanohoop component of the nanohoop-containing rotaxane compound resides over the propyl chain of the molecule constrained within its cavity. In solution, a resonance at @1.43 ppm can be observed, indicating that the propyl chain experiences a particularly strong shielding effect, suggesting that the nanohoop component resides over the propyl chain. On addition of CuI, this signal broadens, but never fully vanishes. Additionally, the appearance of multiple new resonances was observed, which indicates the formation of a new species alongside the metal-free nanohoop-containing rotaxane compound. The nanohoop-containing rotaxane compound was co-crystallized with 1.0 equiv of [Cu(MeCN)$_4$]PF$_6$, which revealed that in the solid state, the nanohoop becomes localized over the triazole unit with the CuI metal coordinated to both the triazole and the nitrogen atom of the nanohoop component. A similar shuttling effect was observed when the nanohoop-containing rotaxane compound was titrated with [Pd(MeCN)$_4$](BF$_4$)$_2$. Notably, in the presence of Pd(II), the observed signals in the $^1$H NMR spectrum were noticeably sharper relative to that observed with [Cu-(MeCN)$_4$](PF$_6$), indicating a less dynamic system. Taken together, it is currently believed that, despite the sterically congested environment, triazole embedded nanohoop-containing rotaxane compound embodiments can bind metals (e.g., CuI and Pd(II)). In some examples, as the amount of Pd(II) increased, the fluorescence of the nanohoop-containing rotaxane compound decreased. As can be seen in FIG. 32, the addition of 1.0 equiv of [Pd(MeCN)$_4$](BF$_4$)$_2$ to the nanohoop-containing rotaxane compound results in a non-emissive rotaxane complex. Given that metalation with Pd(II) effectively traps the fluorophore in a non-emissive state, it was anticipated that de-metalation should result in a turn-on response. The non-emissive rotaxane complex was treated with 1.0 equiv of ethylenediaminetetraacetic acid (EDTA), which quickly resulted in a pronounced 30-fold increase in emission (FIG. 32). The emission responses of a water-soluble nanohoop-containing rotaxane compound 324 also was evaluated. In fact, emission of nanohoop-containing rotaxane compound 324 comprising a constrained compound comprising carboxylate moieties was readily quenched in aqueous media (PBS buffer) by the addition of 1.0 equiv of [Pd(MeCN)$_4$](BF$_4$)$_2$. Upon addition of EDTA to this aqueous solution, it was again found that the emission quickly returned, albeit with reduced intensity (10-fold increase) in some embodiments.

Example 20

Figure 33:
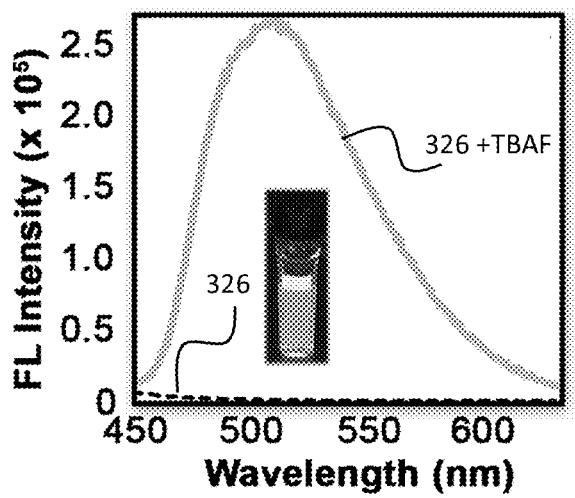
FIG. 33 shows emission spectra (8.6 µM, CHCl$_3$) of 326 before (dotted) and after (solid trace) addition of 1.0 equivalent of TBAF.
Figure 34:
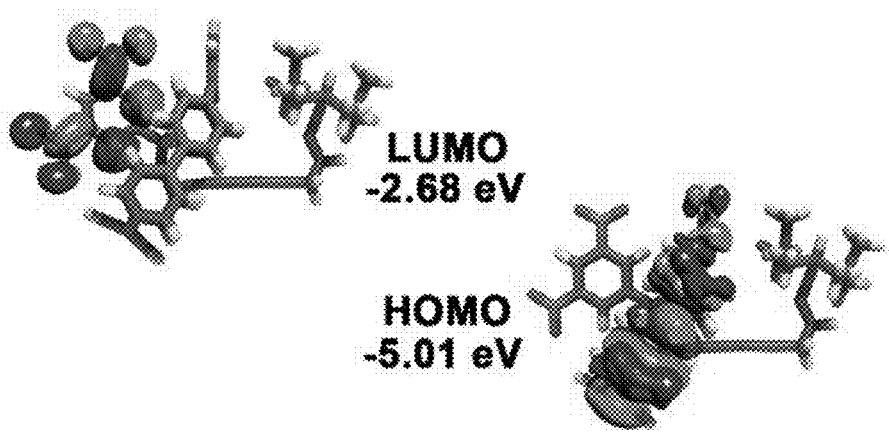
FIG. 34 is an image showing the DFT calculated (B3LYP/6-31 g) frontier molecular orbitals for nanohoop-containing rotaxane compound embodiment 326.

In this example, the ability of nanohoop-containing rotaxane compound embodiments to act as sensor compounds by manipulation of modifiable compounds constrained within the nanohoop core was evaluated. In particular, analyte-induced bond cleavage of the constrained compound was evaluated as a potential chemical modification that could release the fluorescence-quenching constrained compound. A 3,5-dinitro-functionalized compound was made as the compound to be constrained within the nanohoop cavity. This compound comprised a fluoride-cleavable triisopropylsilyl (TIPS) terminal group and was found to be non-emissive (FIG. 33). Treating the nanohoop-containing rotaxane compound 326 comprising this constrained compound with 1.0 equiv of tetra-n-butylammonium fluoride (TBAF) resulted in a nearly instantaneous de-threading event, which was accompanied by a dramatic 123-fold increase in emission intensity (FIG. 33), thereby establishing the ability of the nanohoop-containing rotaxane compound embodiments to serve as a highly responsive self-immolative sensor. This is illustrated schematically below in Scheme 8. Additionally, through density functional theorem (DFT), it was found that the frontier molecular orbitals of nanohoop-containing rotaxane compound 326 are redistributed relative to the corresponding nanohoop compound (FIG. 34). Specifically, for the nanohoop compound, both the highest-occupied molecular orbital (HOMO) and the lowest-unoccupied molecular orbital (LUMO) reside over the nanohoop backbone. In contrast, in the case of the nanohoop-containing rotaxane compound 326, the HOMO is localized on the nanohoop component and the LUMO is localized over the electron-deficient nitrobenzene constrained compound, consistent with a charge-transfer quenching mechanism. As such, modifying the electronic structure of nanohoop-containing rotaxane compound embodiments may provide an additional means for determining suitable sensor compounds.

Scheme 8

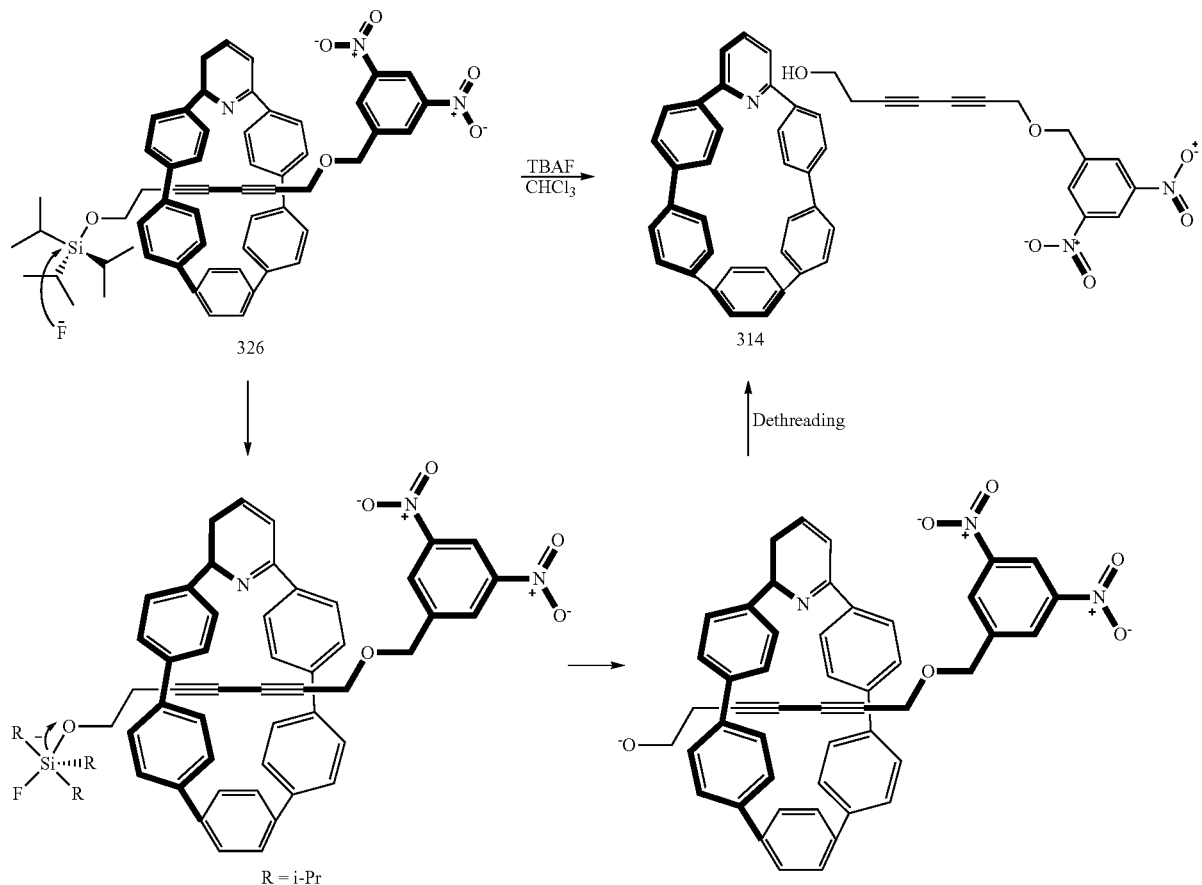

In view of the many possible embodiments to which the principles of the present disclosure may be applied, it should be recognized that the illustrated embodiments are only preferred examples and should not be taken as limiting. Rather, the scope is defined by the following claims. We therefore claim as our invention all that comes within the scope and spirit of these claims.

We claim:

1. A nanohoop compound, having a structure satisfying Formula 1

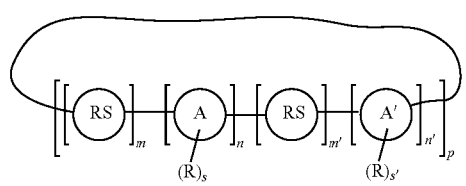

wherein each RS ring independently has a structure satisfying Formula II

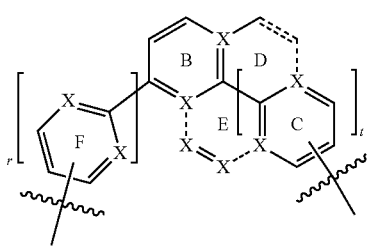

wherein at least one X is N, P, or C-CFG, wherein CFG is a coordinating functional group;
each other X independently is C or C($R^1$) where $R^1$ is selected from an electron-accepting group or an electron-donating group; and
r and t independently are 0 or 1;
each A and A' ring independently is an aromatic ring;
each R independently is selected from hydrogen, an electron-donating group, an electron-accepting group, or any combinations thereof;
m is an integer selected from 1 to 4;
m' is an integer selected from 0 to 4;
each s and s' independently is an integer selected from 0 to 4;
each n and n' independently is an integer selected from 0 to 24; and
p is an integer selected from 1 to 20.

2. The nanohoop compound of claim 1, wherein each RS ring independently has a structure satisfying one or more of Formulas IIA-IIC Formula IIA

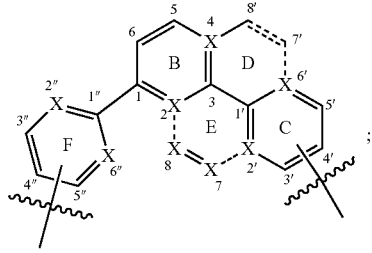

Formula IIB

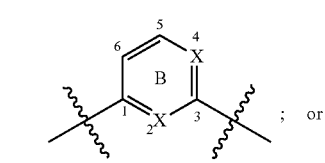
; or

Formula IIC

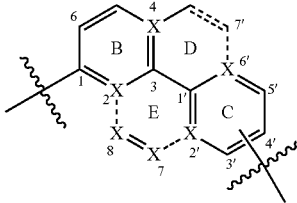

3. The nanohoop compound of claim 1, wherein ring B is a heteroaryl ring and r and t are 0.

4. The nanohoop compound of claim 1, wherein ring B and ring C bind together to provide a hetero-biaryl ring group and r is 0.

5. The nanohoop compound of claim 1, wherein ring B, ring C, and ring D bind together to provide a three-ring heteroaryl ring system and r is 0.

6. The nanohoop compound of claim 1, wherein ring B, ring C, ring D, and ring E bind together to provide a four-ring fused heteroaryl ring system, and r is 0.

7. The nanohoop compound of claim 1, wherein r is 1 and t is 1 and ring B, ring C, and ring F bind together to provide a heterotriaryl ring system.

8. The nanohoop compound of claim 1, wherein the nanohoop compound has a structure satisfying any one or more of Formulas IIIA-IIIF Formula IIIA

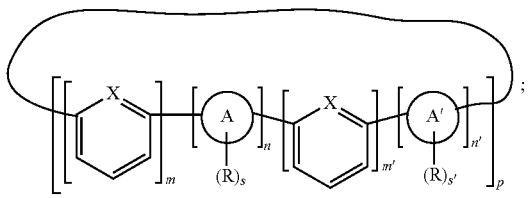

Formula IIIB

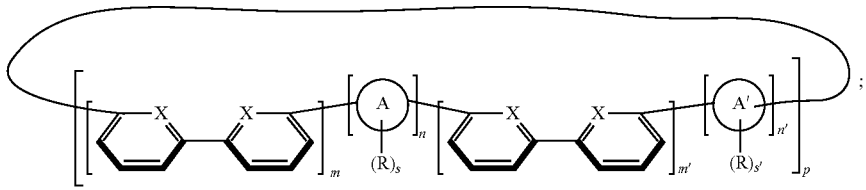

Formula IIIC

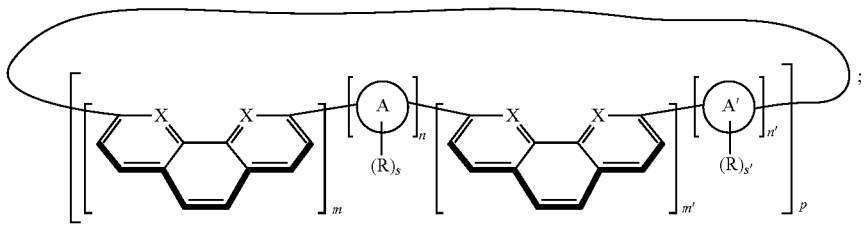

-continued
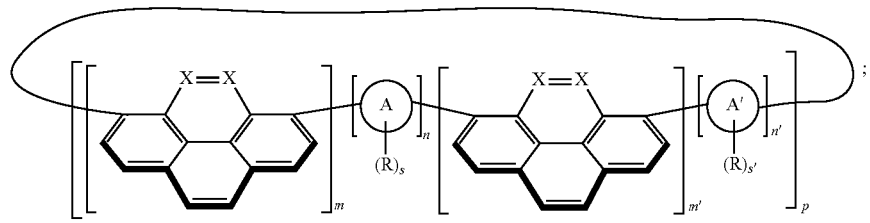
Formula IIID
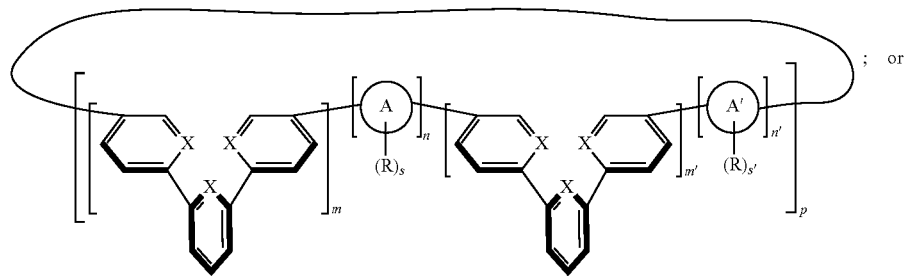
Formula IIIE
; or
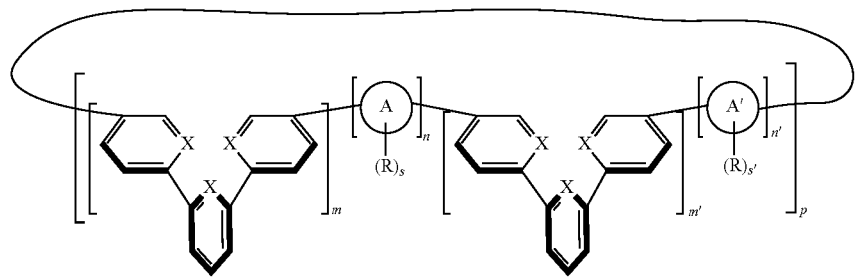
Formula IIIF
.

9. The nanohoop compound of claim 8, wherein for Formulas IIIA, IIIB, IIIC, IIIE, and IIIF, each X is N and for Formula IIID, at least one X is C(R$^1$) where R$^1$ is selected from an electron-accepting group or an electron-donating group and each other X independently is C or C(R$^1$) where R$^1$ is selected from an electron-accepting group or an electron-donating group.

10. The nanohoop compound of claim 1, wherein the nanohoop compound has a structure satisfying any one or more of Formulas IVA-IVC Formula IVA

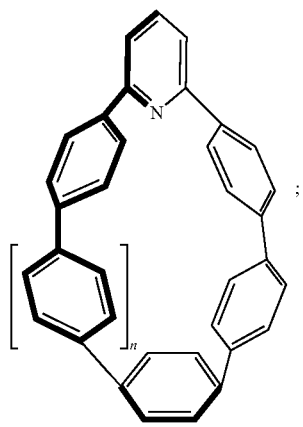

Formula IVB

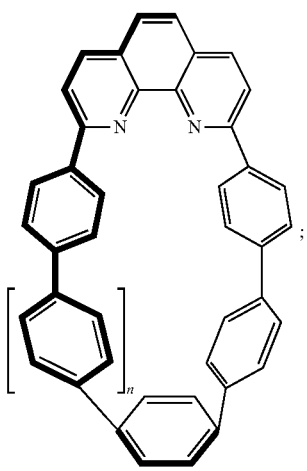

Formula IVC

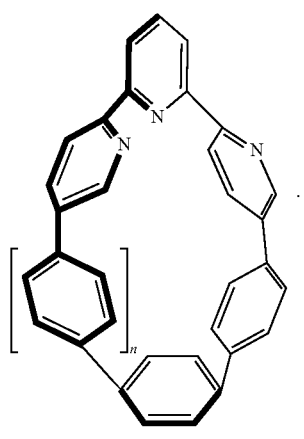

wherein n is 1, or 3-5.

11. The nanohoop compound of claim 1, wherein the nanohoop compound is

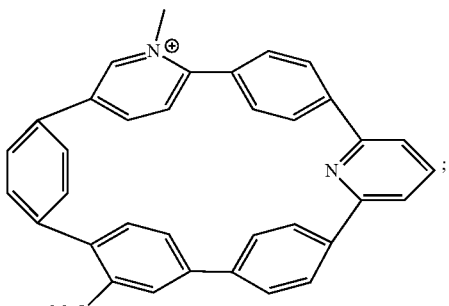

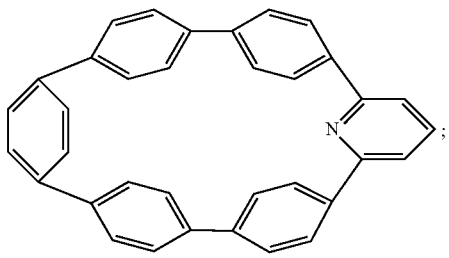

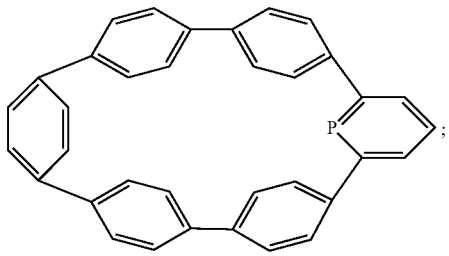

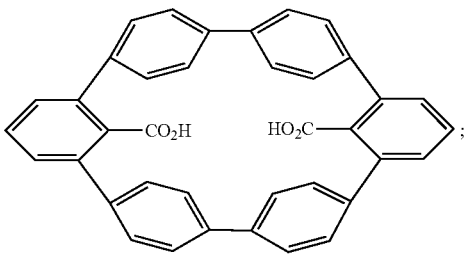

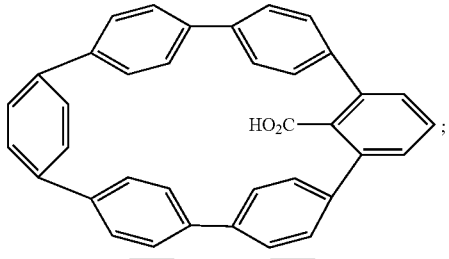

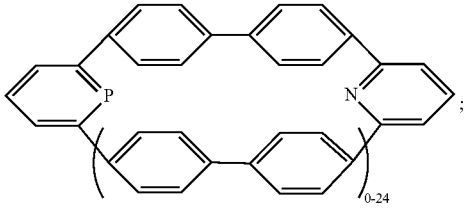

95
-continued
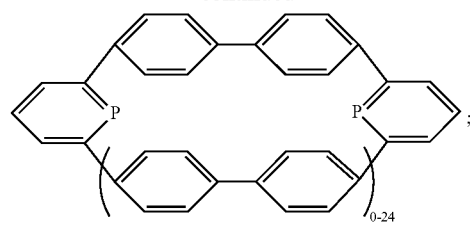
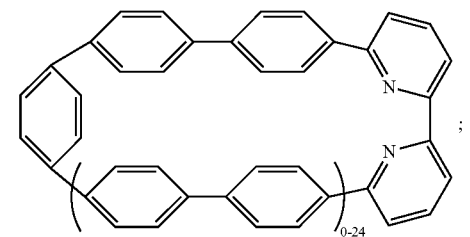
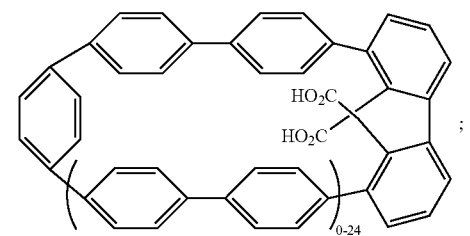
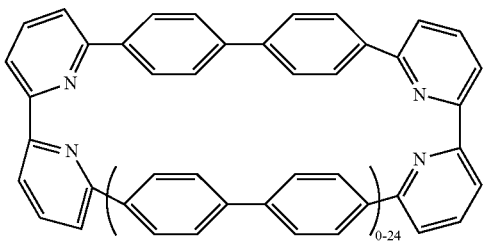
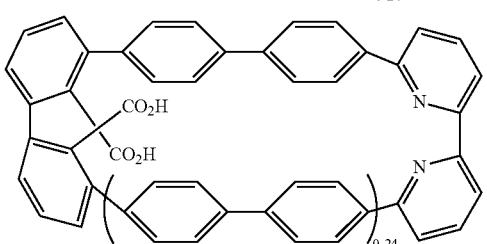
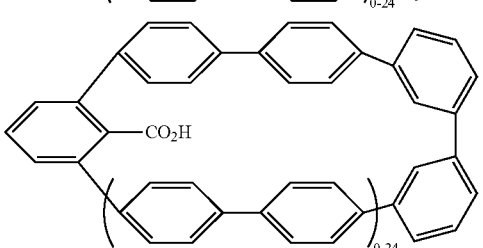
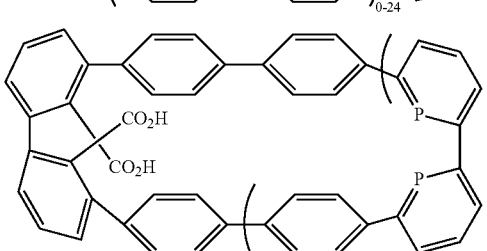
96
-continued
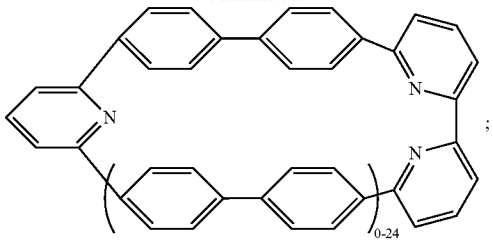
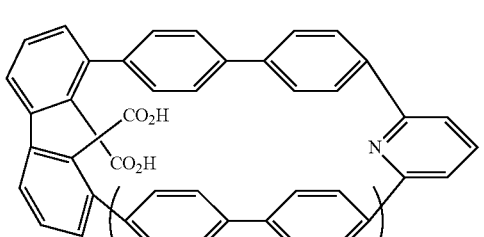
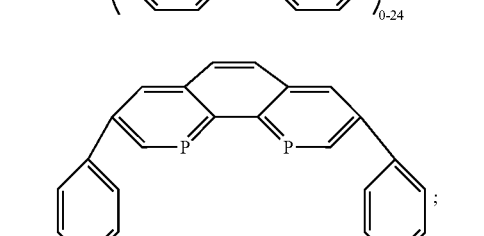
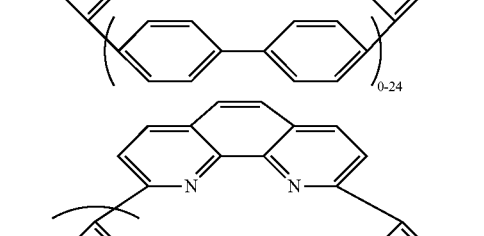
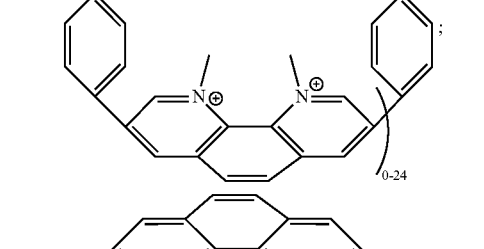
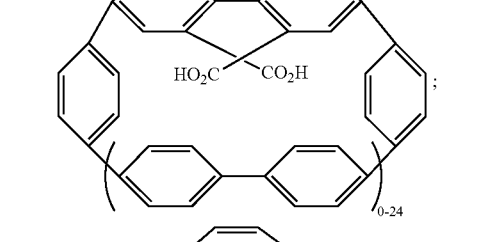
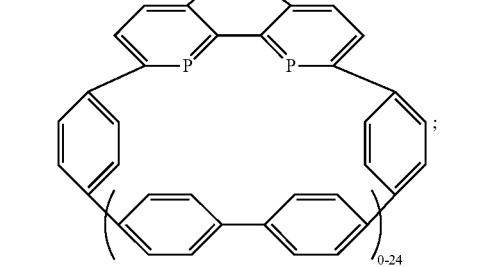

-continued
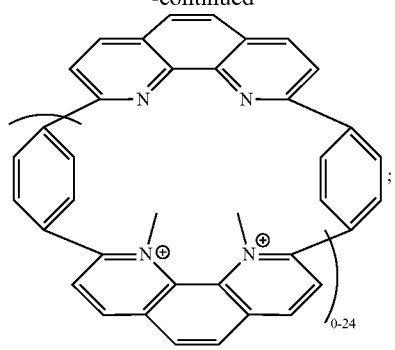
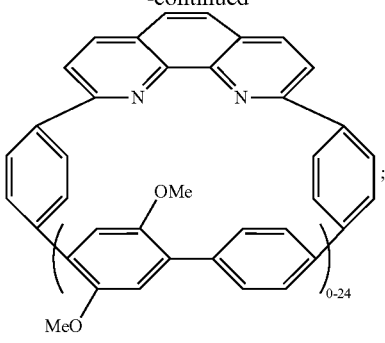
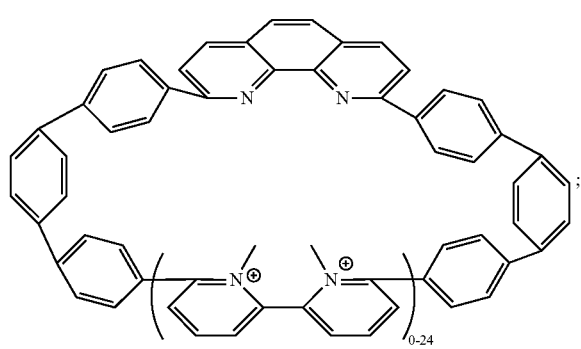
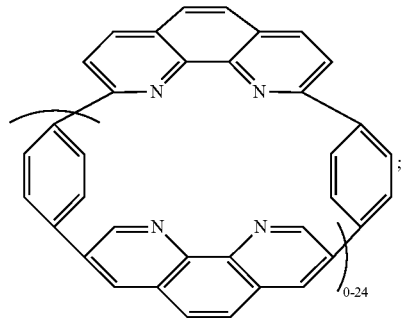
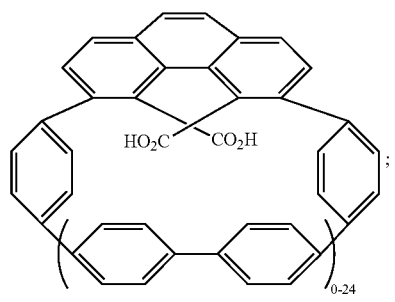
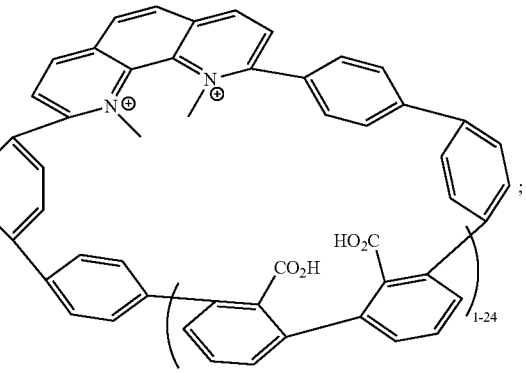
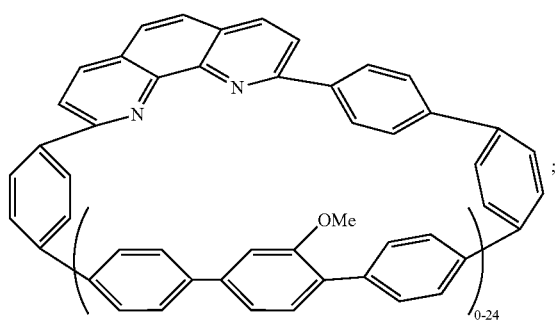
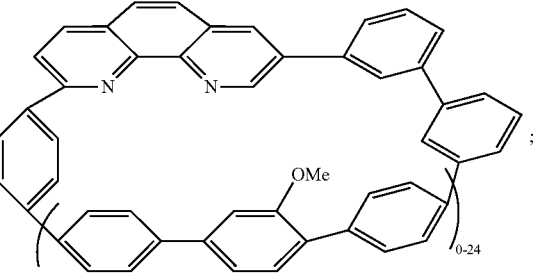
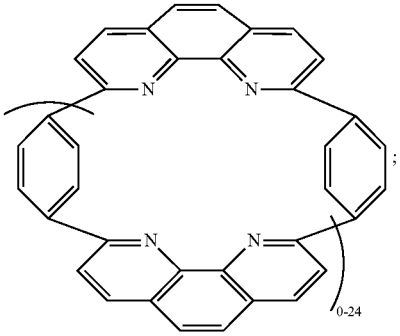
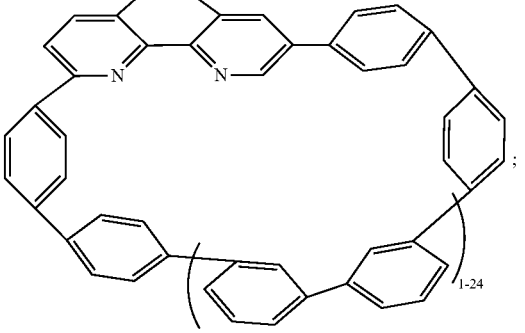

99
-continued
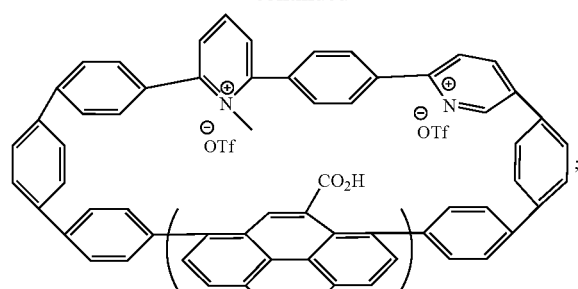
100
-continued
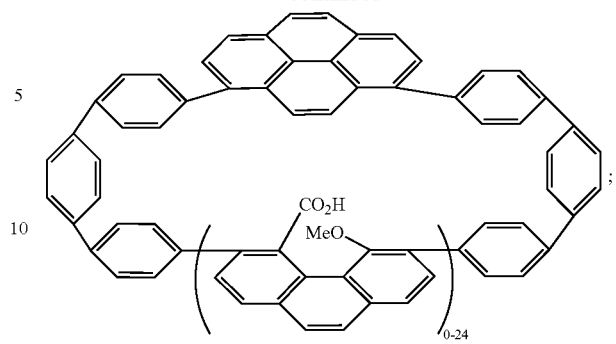
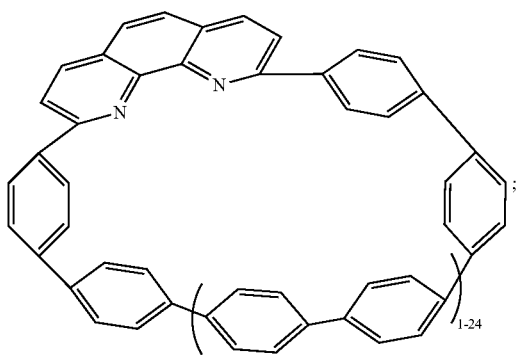
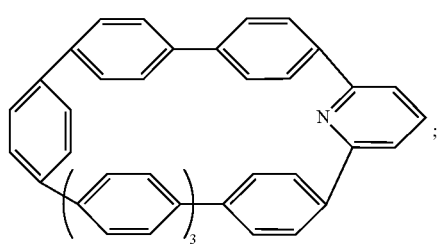
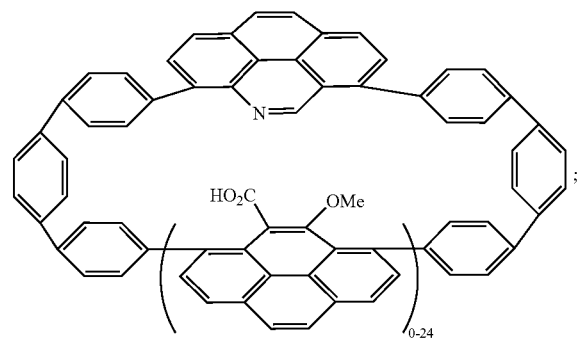
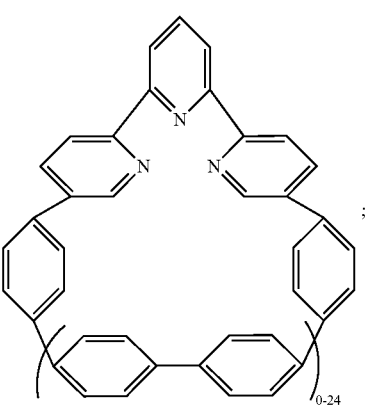

-continued
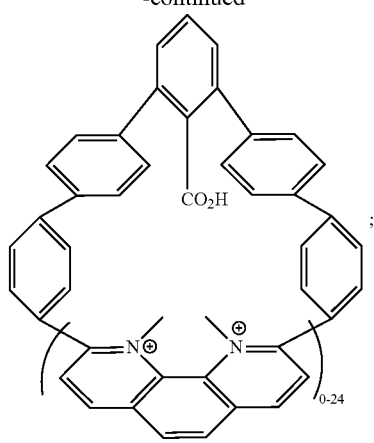
;
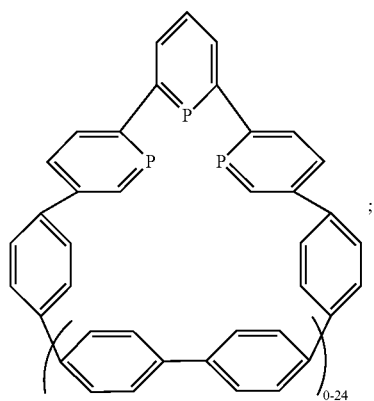
;
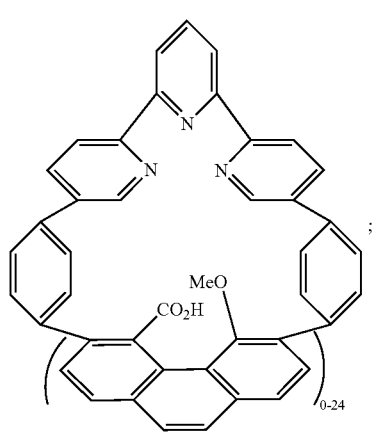
;
-continued
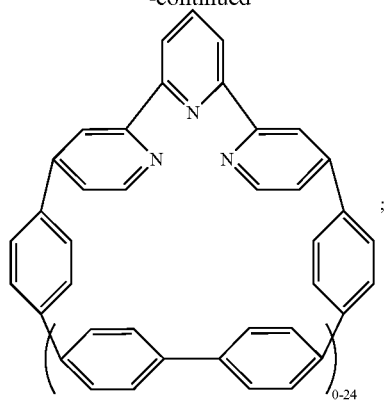
;
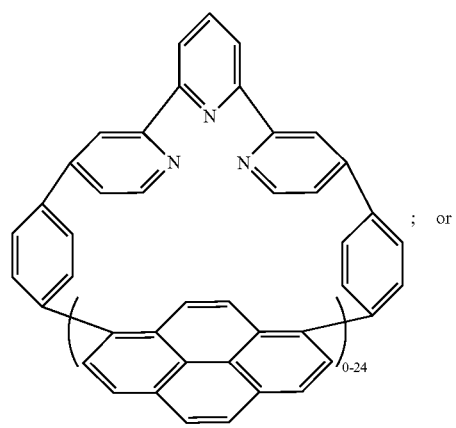
; or
.
12. The nanohoop compound of claim 1, further comprising an interlocked molecule that is confined by a cavity defined by the nanohoop compound.
13. The nanohoop compound of claim 12, wherein the interlocked molecule is a triazole-containing compound or an alkyne-containing compound.

14. The nanohoop compound of claim 12, wherein the nanohoop compound is selected from
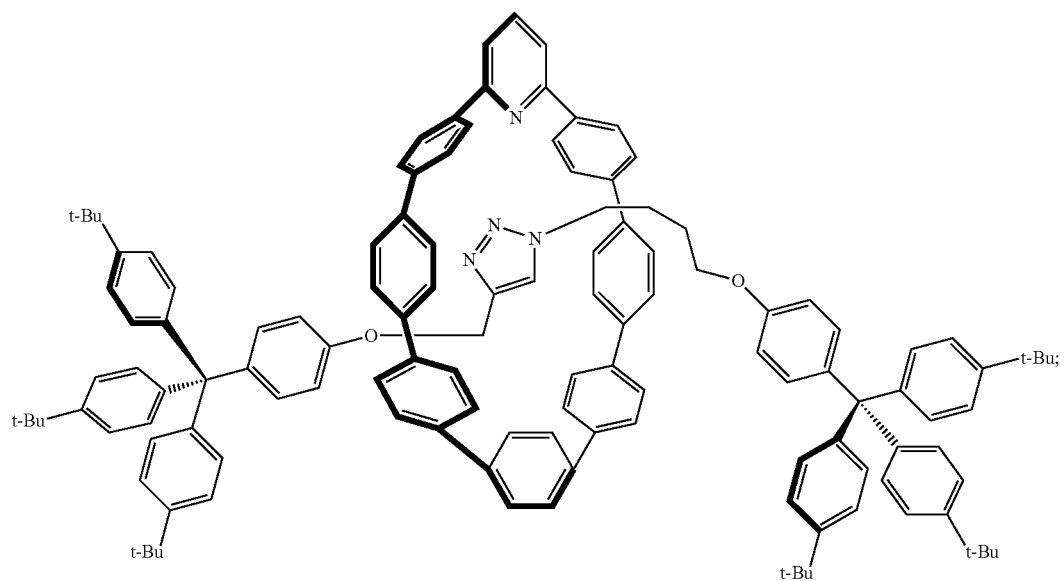
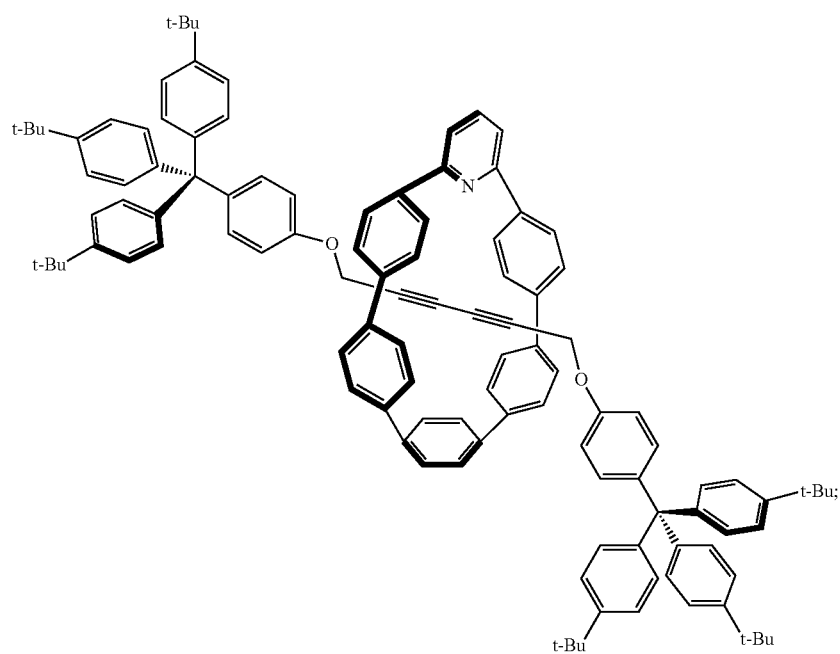

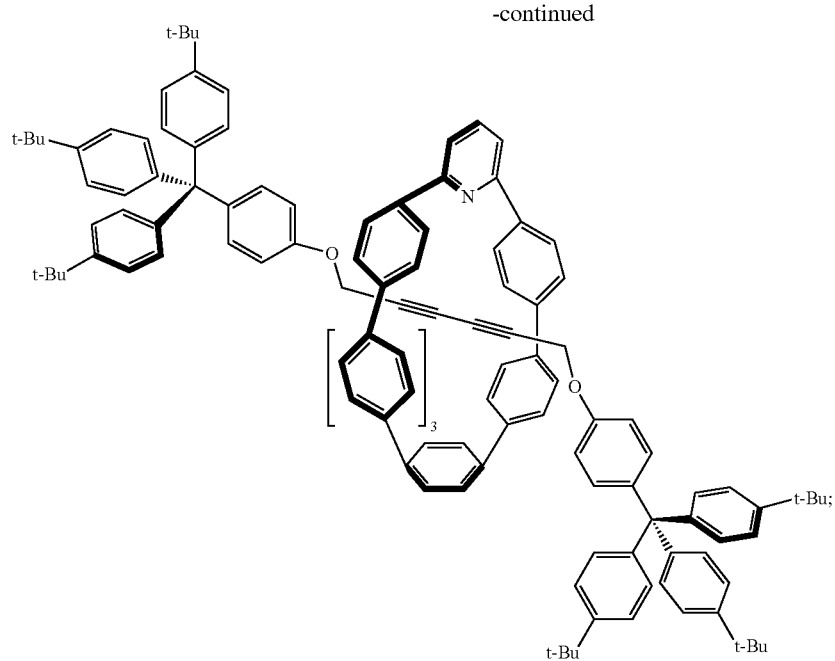
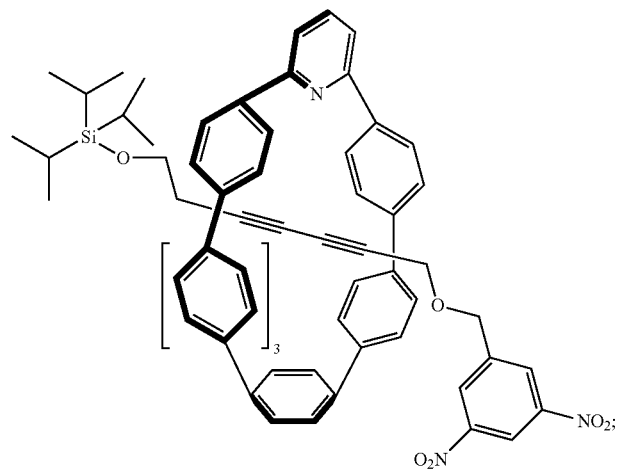
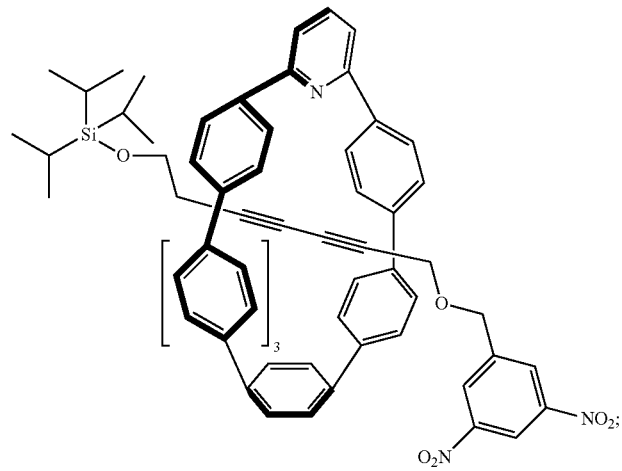

-continued
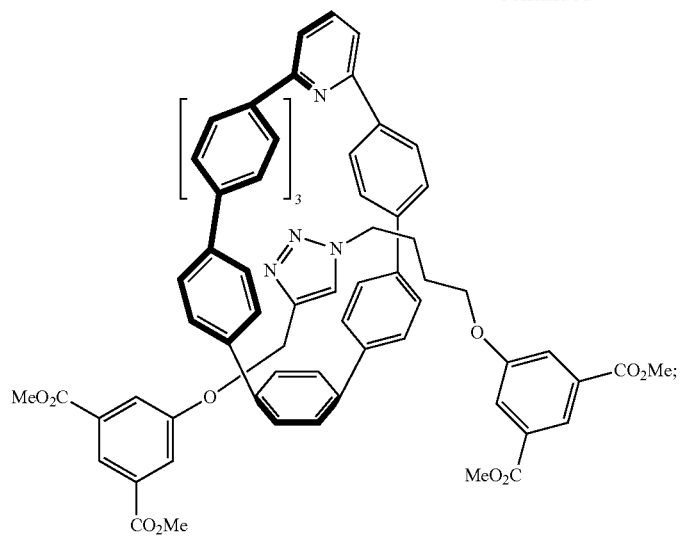
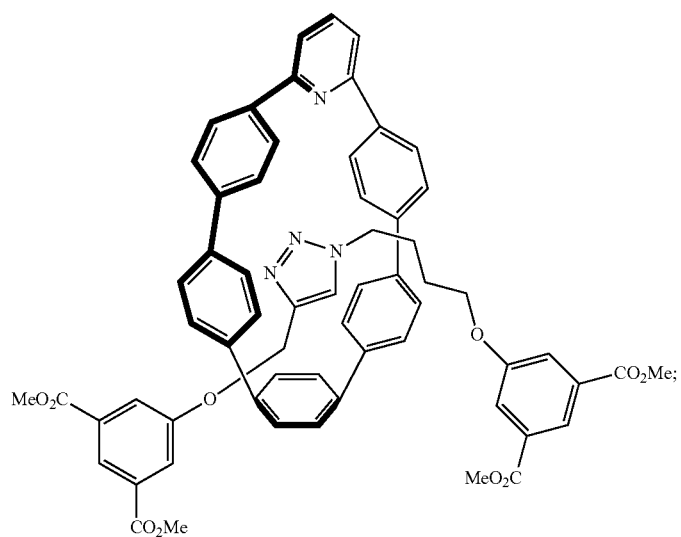
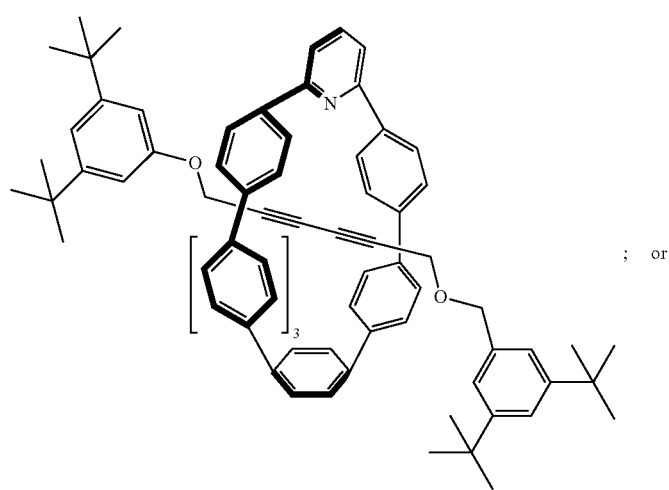
; or

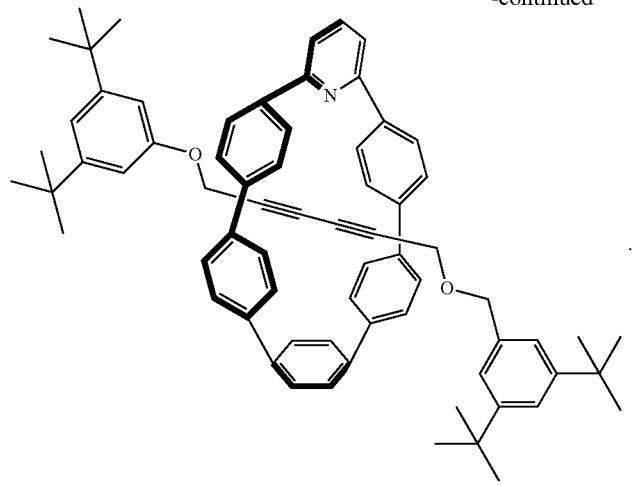
* * * * *